US011795510B2

(12) United States Patent
McDonald et al.

(10) Patent No.: US 11,795,510 B2
(45) Date of Patent: Oct. 24, 2023

(54) IDENTIFICATION OF EPIGENOMIC REPROGRAMMING IN CANCER AND USES THEREOF

(71) Applicants: The Johns Hopkins University, Baltimore, MD (US); Memorial Sloan Kettering Cancer Center, New York, NY (US); Vanderbilt University, Nashville, TN (US)

(72) Inventors: Oliver McDonald, Baltimore, MD (US); Xin Li, Baltimore, MD (US); Christine A. Iacobuzio-Donahue, Baltimore, MD (US); Andrew P. Feinberg, Baltimore, MD (US)

(73) Assignees: The Johns Hopkins University, Baltimore, MD (US); Memorial Sloan Kettering Cancer Center, New York, NY (US); Vanderbilt University, Nashville, TN (US)

( * ) Notice: Subject to any disclaimer, the term of this patent is extended or adjusted under 35 U.S.C. 154(b) by 0 days.

(21) Appl. No.: 16/340,069

(22) PCT Filed: Oct. 5, 2017

(86) PCT No.: PCT/US2017/055376
§ 371 (c)(1),
(2) Date: Apr. 5, 2019

(87) PCT Pub. No.: WO2018/067840
PCT Pub. Date: Apr. 12, 2018

(65) Prior Publication Data
US 2019/0233903 A1  Aug. 1, 2019

Related U.S. Application Data

(60) Provisional application No. 62/405,155, filed on Oct. 6, 2016.

(51) Int. Cl.
*C12Q 1/6886* (2018.01)
*G01N 33/574* (2006.01)
*A61P 43/00* (2006.01)
*A61P 35/04* (2006.01)

(52) U.S. Cl.
CPC ........... *C12Q 1/6886* (2013.01); *A61P 35/04* (2018.01); *A61P 43/00* (2018.01); *G01N 33/57484* (2013.01); *C12Q 2600/156* (2013.01); *C12Q 2600/158* (2013.01)

(58) Field of Classification Search
CPC ........... C12Q 1/6886; C12Q 2600/156; C12Q 2600/158; G01N 33/57484; G01N 2800/52
See application file for complete search history.

(56) References Cited

U.S. PATENT DOCUMENTS

| 7,153,691 B2 | 12/2006 | Ferguson |
| 9,763,956 B2 | 9/2017 | Bernstein et al. |
| 2011/0053882 A1* | 3/2011 | Yu ........................ A61K 31/519 435/325 |
| 2014/0128283 A1 | 5/2014 | Feinberg et al. |
| 2015/0174138 A1 | 6/2015 | Bernstein et al. |

FOREIGN PATENT DOCUMENTS

| JP | 2011-504462 A | 11/1997 |
| JP | 2006506610 | 2/2006 |
| JP | 2014519319 | 8/2014 |
| WO | WO 2013/152186 A1 | 10/2013 |
| WO | WO 2014/056627 A1 | 4/2014 |
| WO | WO 2016/144371 A1 | 9/2016 |
| WO | WO 2016/172332 A1 | 10/2016 |

OTHER PUBLICATIONS

McDonald et al. Nature Structural & Molecular Biology. 2011. 18(8):867-874 with Online Methods. (Year: 2011).*
European Search Report dated Jun. 9, 2020, regarding PCT/US/2017/055376.
Winston Timp et al: "Large hypomethylated blocks as a universal defining epigenetic alteration in human solid tumors", Genome Medicine, vol. 6, No. 8, Aug. 26, 2014, p. 61.
Kasper Daniel Hansen et al: "Increased methylation variation in epigenetic domains across cancer types", Nature Genetics, vol. 43, No. 8, Jun. 26, 2011 pp. 768-775.
George S. Karagiannis et al: "Signatures of breast cancer metastasis at a glance", Journal of Cell Science, vol. 129, No. 9, Apr. 15, 2016, pp. 1751-1758.
Hansen et al., Increased methylation variation in epigenetic domains across cancer types, Nature Genetics, Jun. 2011,43(8):768-775.
JP Office Action in Japanese Application No. 2019-518463, dated Aug. 24, 2021, 8 pages (with English translation).
Karagiannis et al., "Signatures of breast cancermetastasis at a glance", Journal of Cell Science, May 2016, 129(9):1751-1758.
McDonald et al., "Genome-scale epigenetic reprogramming during epithelial to mesenchymal transition", Nature Structural & Molecular Biology, Jul. 2011, 18(8):867-874.
Timp et al., "Large hypomethylates blocks as a universal defining epigenetic alteration in human solid tumors", Genome Medicine, Aug. 2014, 6(8):1-11.
JP Office Action in Japanese Application No. 2019-518463, dated May 10, 2022, 5 pages (with English translation).

* cited by examiner

*Primary Examiner* — Joseph G. Dauner
(74) *Attorney, Agent, or Firm* — DLA Piper LLP (US)

(57) ABSTRACT

The present invention relates to a method of identifying epigenetic reprogramming. Identifying epigenetic reprogramming comprises detecting large organized heterochromatin lysine (K)-9 modified domains (LOCKs) and large DNA hypomethylated blocks in a sample containing DNA from a subject having cancer, for example, PDAC.

11 Claims, 25 Drawing Sheets

Specification includes a Sequence Listing.

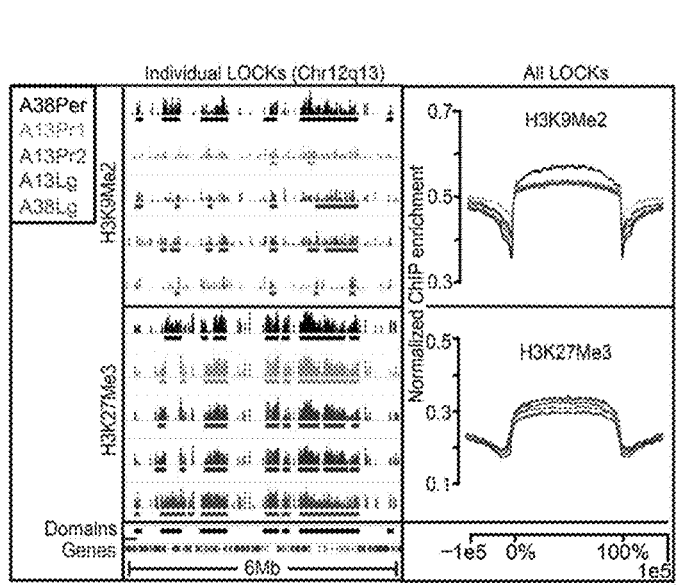
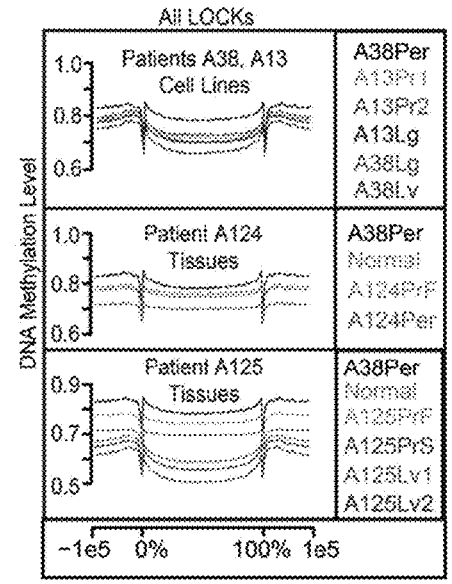
FIGURE 2A
FIGURE 2B
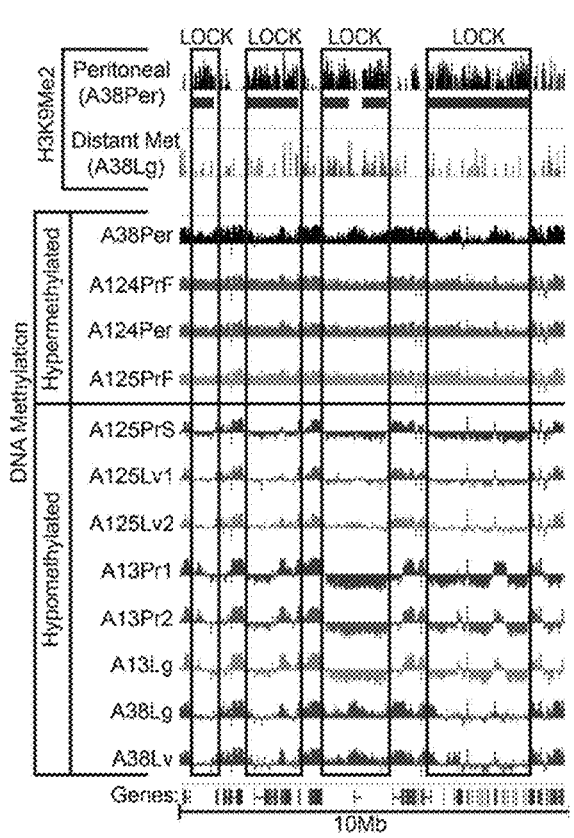
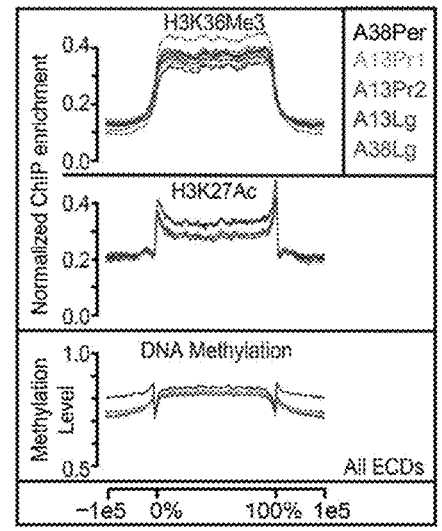
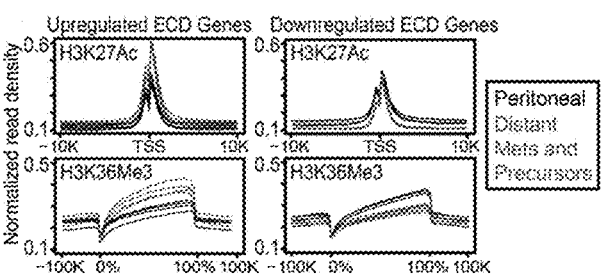
FIGURE 2C
FIGURE 2D
FIGURE 2E

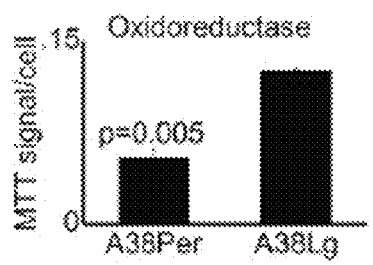
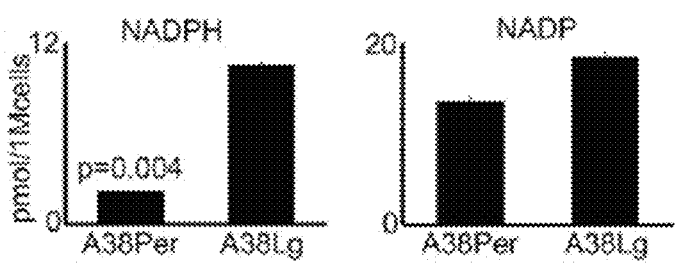
FIGURE 14A　　　　　　　　　FIGURE 14B
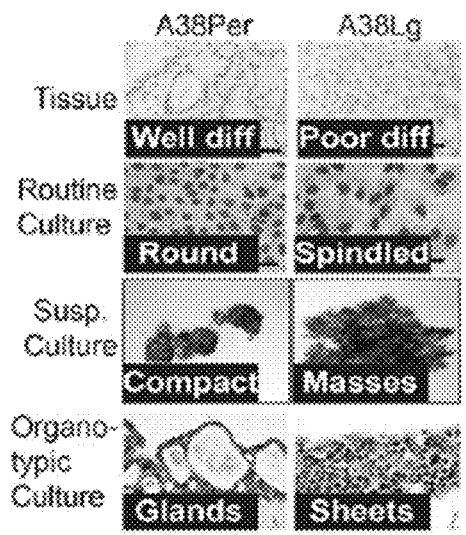
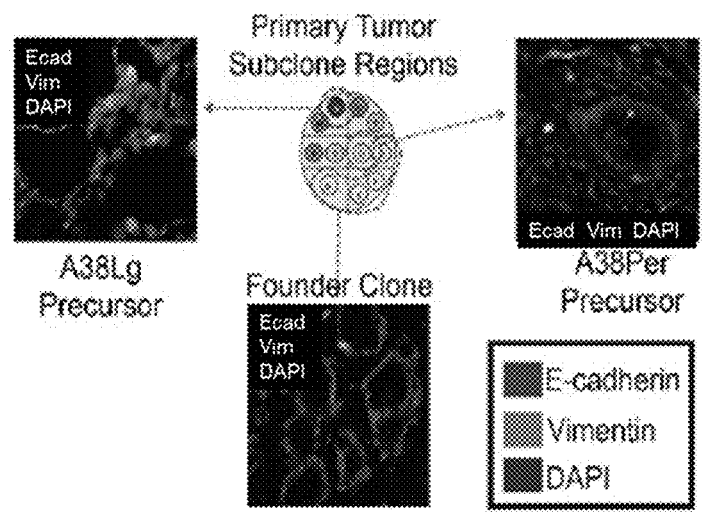
FIGURE 14C　　　　　　　　　FIGURE 14D
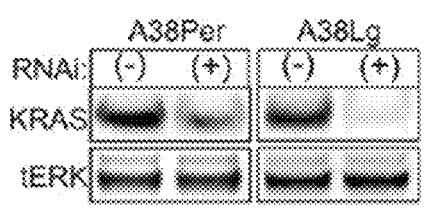
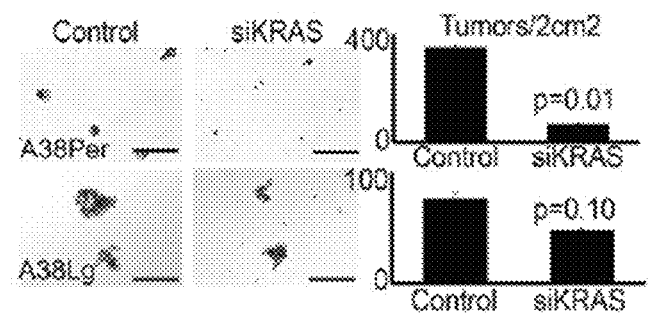
FIGURE 14E　　　　　　　　　FIGURE 14F

SEQUENCE LISTING

<160> NUMBER OF SEQ ID NOS: 33

<210> SEQ ID NO 1
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr18_24.258F

<400> SEQUENCE: 1
gctcagccct gtatcagcca gc                                        22

<210> SEQ ID NO 2
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr18_24.258R

<400> SEQUENCE: 2
gggttacagg tatgagccac tgc                                       23

<210> SEQ ID NO 3
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr18_24.506F

<400> SEQUENCE: 3
aatggagaag tcaggaatgt agtcc                                     25

<210> SEQ ID NO 4
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr18_24.506R

<400> SEQUENCE: 4
gtatttcatt tatcaagttg cagctcc                                   27

<210> SEQ ID NO 5
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr18_24.834F -continued

<400> SEQUENCE: 5
tttgcttctc actccaagtt catcc                               25

<210> SEQ ID NO 6
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr18_24.834R

<400> SEQUENCE: 6
caacctcagg aacaatgcat cagc                                24

<210> SEQ ID NO 7
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr18_24.834R

<400> SEQUENCE: 7
caacctcagg aacaatgcat cagc                                24

<210> SEQ ID NO 8
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr18_25.125.6F

<400> SEQUENCE: 8
cgaaacagtc cagctgctat gg                                  22

<210> SEQ ID NO 9
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr18_25.125.6R

<400> SEQUENCE: 9
cttggctatt gtgactggta ctgc                                24

<210> SEQ ID NO 10
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr18_25.428.000F

<400> SEQUENCE: 10
ccaatgcact aatttaatgt catgc                               25

```
<210> SEQ ID NO 11
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr18_25.428.000R

<400> SEQUENCE: 11
cgtgctaatt tctatggtac actgg                                              25

<210> SEQ ID NO 12
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Pri,er: Chr18_25.632F

<400> SEQUENCE: 12
cctaatccaa tatgcctggt gtcc                                               24

<210> SEQ ID NO 13
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr18_25.632R

<400> SEQUENCE: 13
ctggaagtct gagatcaagg tgc                                                23

<210> SEQ ID NO 14
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr18_25.778F

<400> SEQUENCE: 14
aataatcacg aagcacttct gtattgc                                            27

<210> SEQ ID NO 15
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr18_25.778R

<400> SEQUENCE: 15
tcaccagcag acatagtcat acttcc                                             26

<210> SEQ ID NO 16
<211> LENGTH: 24
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr18_25.808F

<400> SEQUENCE: 16
ccttggaggt ggagtctaca gagg                                           24

<210> SEQ ID NO 17
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr18_25.808R

<400> SEQUENCE: 17
ctgctagcgt agccatctga gatcg                                          25

<210> SEQ ID NO 18
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr3_25.398F

<400> SEQUENCE: 18
gccctgtctt cccagaatca ttgc                                           24

<210> SEQ ID NO 19
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr3_25.398R

<400> SEQUENCE: 19
catgaagcct atgaagatca ttatgg                                         26

<210> SEQ ID NO 20
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr3_25.540F

<400> SEQUENCE: 20
tttagccagc aagtattcta gcatgg                                         26

<210> SEQ ID NO 21
<211> LENGTH: 27
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<223> OTHER INFORMATION: Primer: Chr3_25.540R

<400> SEQUENCE: 21
gtcagtgtga ttcagtaaca atgatgg                                              27

<210> SEQ ID NO 22
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr3_25.622F

<400> SEQUENCE: 22
cctgctcaag gctgacatgt cacc                                                 24

<210> SEQ ID NO 23
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr3_25.622R

<400> SEQUENCE: 23
gtcggactcg atggtcagca ctgg                                                 24

<210> SEQ ID NO 24
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr3_25.733F

<400> SEQUENCE: 24
aacccgaaac tttcaatgca cttgg                                                25

<210> SEQ ID NO 25
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr3_25.733R

<400> SEQUENCE: 25
cttcctctat agtgaagacc ctagg                                                25

<210> SEQ ID NO 26
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr3_25.812F
<220> FEATURE:
```

<220> NAME/KEY: misc_feature
<223> OTHER INFORMATION: Primer: Chr3_25.733R

<400> SEQUENCE: 26
tatggccatt cttgcagcag taagg     25

<210> SEQ ID NO 27
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr3_25.812R

<400> SEQUENCE: 27
aaagttggct aaggacatga ataggc     26

<210> SEQ ID NO 28
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr3_25.973F

<400> SEQUENCE: 28
ggagattccc tcaggtgcct atacc     25

<210> SEQ ID NO 29
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: Chr3_25.973R

<400> SEQUENCE: 29
ctggtgttcc aggcaccact gagg     24

<210> SEQ ID NO 30
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: CDH2F

<400> SEQUENCE: 30
ttattactcc tggtgcgagt     20

<210> SEQ ID NO 31
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: CDH2R

<400> SEQUENCE: 31

```
gagctgatga caaatagcgg                                              20

<210> SEQ ID NO 32
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: TOP2BF

<400> SEQUENCE: 32
gttacaggtg gtcgtaatgg tt                                           22

<210> SEQ ID NO 33
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer: TOP2BR

<400> SEQUENCE: 33
ttggcttcag aagtcttcat ca                                           22
```

IDENTIFICATION OF EPIGENOMIC REPROGRAMMING IN CANCER AND USES THEREOF

CROSS-REFERENCE TO RELATED APPLICATIONS

This application is a 35 USC § 371 National Stage application of International Application No. PCT/US2017/055376 filed Oct. 5, 2017; which claims the benefit under 35 USC § 119(e) to U.S. Application Ser. No. 62/405,155 filed Oct. 6, 2016. The disclosure of each of the prior applications is considered part of and is incorporated by reference in the disclosure of this application.

STATEMENT REGARDING FEDERALLY SPONSORED RESEARCH OR DEVELOPMENT

This invention was made with government support under CA054358, CA140599, CA179991, CA180682 and CA095103 awarded by the National Institutes of Health. The government has certain rights in the invention.

INCORPORATION OF SEQUENCE LISTING

The material in the accompanying sequence listing is hereby incorporated by reference into this application. The accompanying sequence listing text file, name JHU4080_1WO_1WO_Sequence Listing, was created on Oct. 4, 2017, and is 9 kb. The file can be assessed using Microsoft Word on a computer that uses Windows OS.

BACKGROUND OF THE INVENTION

Field of the Invention

The invention relates generally to genetic analysis and more specifically to cancer and the epigenetic influence on progression and metastases of cancer.

Background Information

During the evolutionary progression of pancreatic ductal adenocarcinoma (PDAC), heterogeneous subclonal populations emerge that drive primary tumor growth, regional spread, distant metastasis, and patient death. However, the genetics of metastases largely reflects that of the primary tumor in untreated patients, and PDAC driver mutations are shared by all subclones. This raises the possibility that an epigenetic process might be operative during metastasis. Here we detected striking epigenetic reprogramming of global chromatin modifications during the natural evolutionary history of distant metastasis. Genome-wide mapping revealed that these global changes were targeted to thousands of large chromatin domains across the genome that collectively specified malignant traits, including euchromatin and large organized chromatin K9-modified (LOCK) heterochromatin. Parallel to these changes, distant metastases co-evolved a dependence on the oxidative branch of the pentose phosphate pathway (oxPPP), and oxPPP inhibition selectively reversed reprogrammed chromatin and blocked tumorigenic potential. Thus, divergent metabolic, epigenetic, and tumorigenic programs emerged during the evolution of pancreatic cancer progression.

Despite significant progress in survival rates for most human cancers, PDAC remains nearly universally lethal with survival rates of 8%. In fact, PDAC is projected to be the second-leading cause of cancer deaths in the western world by 2020. Primary PDACs have been shown to contain distinct subclonal populations. However, these subclones share identical driver mutations and the genetics of metastases largely reflects that of the primary tumor. Furthermore, subclones are defined genetically by their unique progressor mutations, the vast majority if not all of which are thought to be passenger events. This raises questions as to what mechanisms might drive progression and metastasis during the natural history of disease evolution.

One prometastatic candidate is epigenomic regulation. In particular, the inventors wished to investigate the role of large-scale epigenomic changes during PDAC subclonal evolution and distant metastasis, especially within heterochromatin domains including large organized heterochromatin lysine (K)-9 modified domains (LOCKs) and large DNA hypomethylated blocks. These regions could represent selectable targets for large-scale epigenetic reprogramming, since they occupy over half of the genome, partially overlap with one another, and are found in many human cancers including PDAC. It was therefore hypothesized that epigenomic dysregulation within these regions could be a major selective force for tumor progression, given the lack of any consistent metastasis-specific driver mutations.

SUMMARY OF THE INVENTION

The present invention relates to a method of identifying targets for epigenetic reprogramming comprising detecting large organized heterochromatin lysine (K)-9 modified domains (LOCKs) and large DNA hypomethylated blocks in a sample containing DNA from a subject having cancer. For example, the method applies to a subject that has or is at risk of having PDAC and/or metastasis thereof. In one aspect, the detection comprises analysis of H3K9Me2/3 and/or H4K20Me3. In another aspect, the detection comprises analysis of H3K27Ac and/or H3K9Ac.

In another embodiment, the invention provides for the use of differentially expressed genes to identify metastatic propensity in primary tumors, wherein the genes are selected from genes in the Tables herein, oxidative stress genes, EMT genes, immunological response genes, DNA repair genes, glucose metabolism genes, oxPPP genes, and PGD genes.

In another embodiment, the invention provides a method for identifying agents or compounds to affect epigenomic changes, including inhibition of oxPPP comprising analyzing a sample from a subject before and after contacting with the agent or compound and determining the effect of the agent or compound on the epigenomic changes.

BRIEF DESCRIPTION OF THE DRAWINGS

FIG. 1A is a series of immunohistochemical stains.
FIG. 1B is a series of immunohistochemical stains.
FIG. 1C is a series of immunohistochemical stains.
FIG. 1D is a series of immunohistochemical stains.
FIG. 1E is a series of immunohistochemical stains.
FIGS. 2A-2D relate to epigenomic reprogramming of chromatin domains during PDAC subclonal evolution.
FIG. 2A is a graphical representation of data.
FIG. 2b is a graphical representation of data.
FIG. 2C is a graphical representation of data.
FIG. 2D is a graphical representation of data.

FIG. 2E is a graphical representation of data.

FIG. 3A is a graphical representation of data.
FIG. 3B is a series of western blot images.
FIG. 3C is a graphical representation of data.
FIG. 3D is a series of western blot images.
FIG. 3E is a series of western blot images.
FIG. 3F is a graphical representation of data.
FIG. 3G is a series of images of tumor forming assays and related graphical plots.

FIG. 4A is a graphical representation of data.
FIG. 4B is a graphical representation of data.
FIG. 4C is a graphical representation of data.
FIG. 4D is a schematic diagram.
FIG. 4E is a series of graphical representations of data.
FIG. 4F is a graphical representation of data.

FIG. 5A is a series of western blot images.
FIG. 5B is a series of western blot images.
FIG. 5C is a series of images of tumor forming assays and related graphical plots.
FIG. 5D is a series of images of tumor forming assays and related graphical plots.

FIG. 6A is a series of graphical representations of data.
FIG. 6B is a series of graphical representations of data.
FIG. 6C is a series of images of tumor forming assays and related graphical plots.
FIG. 6D is a series of images and related graphical plots.
FIG. 6E is a series of graphical plots.
FIG. 6F is a series of images of tumor forming assays and related graphical plots.

FIG. 7A is a series of western blot images.
FIG. 7B is a series of western blot images.

FIG. 8A is a series of immunohistochemical stains.
FIG. 8B is a graphical representation of data.
FIG. 8C is a table.
FIG. 8D is a series of western blot images.
FIG. 8E is a series of western blot images.

FIG. 10A is a graphical representation of data.
FIG. 10B is a graphical representation of data.

FIG. 11B is a series of graphical representations of data.

FIG. 13A is a graphical representation of data.
FIG. 13B is a graphical representation of data.
FIG. 13C is a graphical representation of data.
FIG. 13D is a graphical representation of data.
FIG. 13E is a graphical representation of data.

FIGS. 14A-14F relate to malignant heterogeneity between A38 subclones.

FIG. 14A is a graphical representation of data.
FIG. 14B is a series of graphical representations of data.
FIG. 14C is a series of immunohistochemical stains.
FIG. 14D is a series of immunohistochemical stains.
FIG. 14E is a series of western blot images.
FIG. 14F is a series of images of tumor forming assays and related graphical plots.

FIG. 15A is a series of graphical representations of data.
FIG. 15B is a series of graphical representations of data.
FIG. 15C is a series of graphical representations of data.

FIG. 16A is a series of graphical representations of data.
FIG. 16B is a series of graphical representations of data.

FIG. 17A is a series of graphical representations of data.
FIG. 17B is a series of graphical representations of data.
FIG. 17C is a series of graphical representations of data.

FIG. 18A is a series of western blot images.
FIG. 18B is a series of western blot images.
FIG. 18C is a series of western blot images.

FIG. 19A is a series of graphical representations of data.
FIG. 19B is a series of graphical representations of data.
FIG. 19C is a series of graphical representations of data.
FIG. 19D is a series of graphical representations of data.

FIG. 20A is a series of images of tumor forming assays and related graphical plots.
FIG. 20B is a series of images of tumor forming assays and related graphical plots.
FIG. 20C is a series of images of tumor forming assays and related graphical plots.

FIG. 20A is a series of graphical representations of data.
FIG. 20B is a series of graphical representations of data.
FIG. 20C is a series of graphical representations of data.

FIG. 22 represents the data showing the loss of LOCKs over the gene in 38-5.

DETAILED DESCRIPTION OF THE INVENTION

Figure 1A:
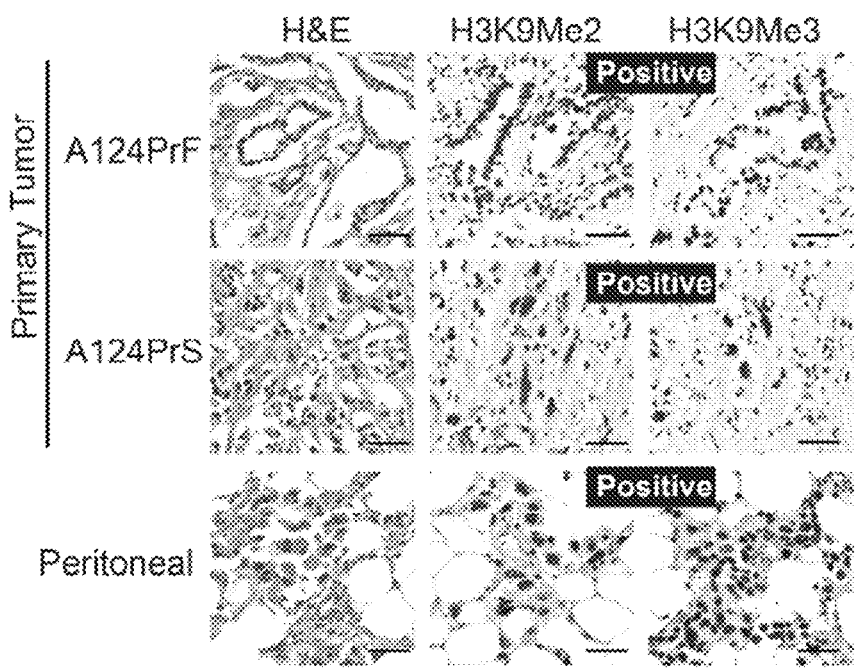
FIGS. 1A-1E relate to global epigenetic reprogramming during the evolution of distant metastasis.
Figure 1B:
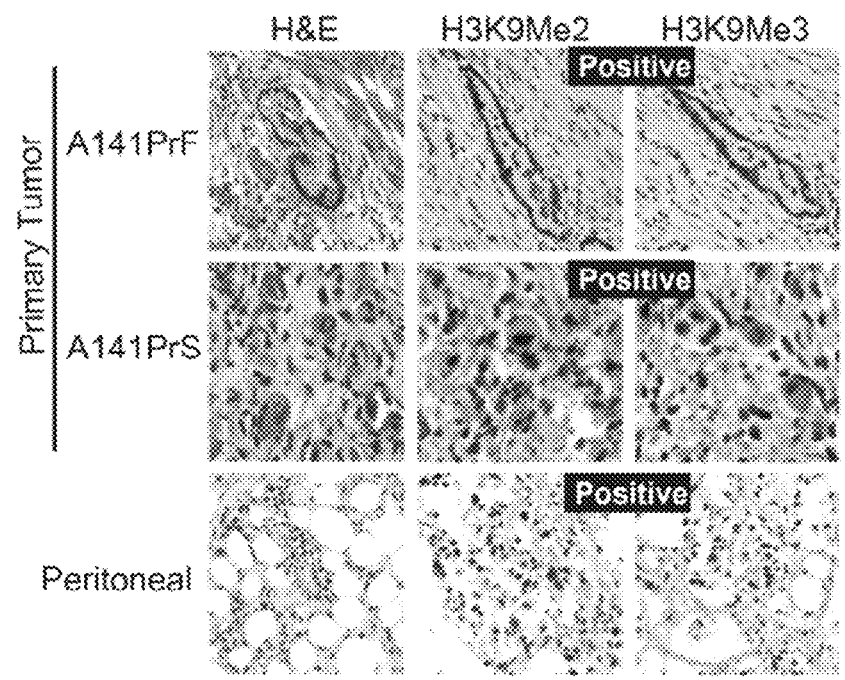

The present invention is based on the seminal discovery that a prometastatic candidate is epigenomic regulation. The invention is based on discovery of the role of large-scale epigenomic changes during PDAC subclonal evolution and distant metastasis, especially within heterochromatin domains including large organized heterochromatin lysine (K)-9 modified domains (LOCKs) and large DNA hypomethylated blocks. These regions represent selectable targets for large-scale epigenetic reprogramming, since they occupy over half of the genome, partially overlap with one another, and are found in many human cancers including PDAC. The inventors therefore hypothesized that epigenomic dysregulation within these regions could be a major selective force for tumor progression, given the lack of any consistent metastasis-specific driver mutations.

Before the present systems and methods are described, it is to be understood that this invention is not limited to particular systems, methods, and experimental conditions described, as such systems, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The present invention provides a method of identifying targets for epigenetic reprogramming comprising detecting large organized heterochromatin lysine (K)-9 modified domains (LOCKs) and large DNA hypomethylated blocks in a sample containing DNA from a subject having cancer. For example, the method applies to a subject that has or is at risk of having PDAC and/or metastasis thereof. In one aspect, the detection comprises analysis of H3K9Me2/3 and/or H4K20Me3.

As used herein, reprogramming, is intended to refer to a process that alters or reverses the differentiation status of a somatic cell that is either partially or terminally differentiated. Reprogramming of a somatic cell may be a partial or complete reversion of the differentiation status of the somatic cell. In an exemplary aspect, reprogramming is complete wherein a somatic cell is reprogrammed into an iPS cell. However, reprogramming may be partial, such as reversion into any less differentiated state. For example, reverting a terminally differentiated cell into a cell of a less differentiated state, such as a multipotent cell.

As used herein, pluripotent cells include cells that have the potential to divide in vitro for an extended period of time (greater than one year) and have the unique ability to differentiate into cells derived from all three embryonic germ layers, namely endoderm, mesoderm and ectoderm.

Somatic cells for use with the present invention may be primary cells or immortalized cells. Such cells may be primary cells (non-immortalized cells), such as those freshly isolated from an animal, or may be derived from a cell line (immortalized cells). In an exemplary aspect, the somatic cells are mammalian cells, such as, for example, human cells or mouse cells. They may be obtained by well-known methods, from different organs, such as, but not limited to skin, brain, lung, pancreas, liver, spleen, stomach, intestine, heart, reproductive organs, bladder, kidney, urethra and other urinary organs, or generally from any organ or tissue containing living somatic cells, or from blood cells. Mammalian somatic cells useful in the present invention include, by way of example, adult stem cells, sertoli cells, endothelial cells, granulosa epithelial cells, neurons, pancreatic islet cells, epidermal cells, epithelial cells, hepatocytes, hair follicle cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, other known muscle cells, and generally any live somatic cells. In particular embodiments, fibroblasts are used. The term somatic cell, as used herein, is also intended to include adult stem cells. An adult stem cell is a cell that is capable of giving rise to all cell types of a particular tissue. Exemplary adult stem cells include hematopoietic stem cells, neural stem cells, and mesenchymal stem cells.

As discussed herein, alterations in methylation patterns occur during differentiation or dedifferention of a cell which work to regulate gene expression of critical factors that are 'turned on' or 'turned off' at various stages of differentiation. As such, one of skill in the art would appreciate that many types of agents are capable of altering the methylation status of one or more nucleic acid sequences of a somatic cell to induce pluripotency that may be suitable for use with the present invention.

An agent, as used herein, is intended to include any agent capable of altering the methylation status of one or more nucleic acid sequences of a somatic cell. For example, an agent useful in any of the method of the invention may be any type of molecule, for example, a polynucleotide, a peptide, a peptidomimetic, peptoids such as vinylogous peptoids, chemical compounds, such as organic molecules or small organic molecules, or the like. In various aspects, the agent may be a polynucleotide, such as DNA molecule, an antisense oligonucleotide or RNA molecule, such as microRNA, dsRNA, siRNA, stRNA, and shRNA.

MicroRNA (miRNA) are single-stranded RNA molecules whose expression is known to be regulated by methylation to play a key role in regulation of gene expression during differentiation and dedifferentiation of cells. Thus an agent may be one that inhibits or induces expression of miRNA or may be a mimic miRNA. As used herein, "mimic" microRNAs which are intended to mean a microRNA exogenously introduced into a cell that have the same or substantially the same function as their endogenous counterpart.

In various aspects of the present invention, an agent that alters the methylation status of one or more nucleic acid sequences is a nuclear reprogramming factor. Nuclear reprogramming factors may be genes that induce pluripotency and utilized to reprogram differentiated or semi-differentiated cells to a phenotype that is more primitive than that of the initial cell, such as the phenotype of a pluripotent stem cell. Those skilled in the art would understand that such genes and agents are capable of generating a pluripotent stem cell from a somatic cell upon expression of one or more such genes having been integrated into the genome of the somatic cell or upon contact of the somatic cell with the agent or expression product of the gene. As used herein, a gene that induces pluripotency is intended to refer to a gene that is associated with pluripotency and capable of generating a less differentiated cell, such as a pluripotent stem cell from a somatic cell upon integration and expression of the gene. The expression of a pluripotency gene is typically restricted to pluripotent stem cells, and is crucial for the functional identity of pluripotent stem cells.

Several genes have been found to be associated with pluripotency and suitable for use with the present invention as reprogramming factors. Such genes are known in the art and include, by way of example, SOX family genes (SOX1, SOX2, SOX3, SOX15, SOX18), KLF family genes (KLF1, KLF2, KLF4, KLF5), MYC family genes (C-MYC, L-MYC, N-MYC), SALL4, OCT4, NANOG, LIN28, STELLA, NOBOX, POU5F1 or a STAT family gene. STAT family members may include for example STAT1, STAT2, STAT3, STAT4, STAT5 (STAT5A and STAT5B), and STAT6. While in some instances, use of only one gene to induce pluripotency may be possible, in general, expression of more than one gene is required to induce pluripotency. For example, two, three, four or more genes may be simultaneously integrated into the somatic cell genome as a polycistronic construct to allow simultaneous expression of such genes. In an exemplary aspect, four genes are utilized to induce pluripotency including OCT4, POU5F1, SOX2, KLF4 and C-MYC. Additional genes known as reprogramming factors suitable for use with the present invention are disclosed in U.S. patent application Ser. No. 10/997,146 and U.S. patent application Ser. No. 12/289,873, incorporated herein by reference.

All of these genes commonly exist in mammals, including human, and thus homologues from any mammals may be used in the present invention, such as genes derived from mammals including, but not limited to mouse, rat, bovine, ovine, horse, and ape. Further, in addition to wild-type gene products, mutant gene products including substitution, insertion, and/or deletion of several (e.g., 1 to 10, 1 to 6, 1 to 4, 1 to 3, and 1 or 2) amino acids and having similar function to that of the wild-type gene products can also be used. Furthermore, the combinations of factors are not limited to the use of wild-type genes or gene products. For example, Myc chimeras or other Myc variants can be used instead of wild-type Myc.

The present invention is not limited to any particular combination of nuclear reprogramming factors. As discussed herein a nuclear reprogramming factor may comprise one or more gene products. The nuclear reprogramming factor may also comprise a combination of gene products as discussed herein. Each nuclear reprogramming factor may be used alone or in combination with other nuclear reprogramming factors as disclosed herein. Further, nuclear reprogramming factors of the present invention can be identified by screening methods, for example, as discussed in U.S. patent application Ser. No. 10/997,146, incorporated herein by reference. Additionally, the nuclear reprogramming factor of the present invention may contain one or more factors relating to differentiation, development, proliferation or the like and factors having other physiological activities, as well as other gene products which can function as a nuclear reprogramming factor.

The nuclear reprogramming factor may include a protein or peptide. The protein may be produced from a gene as discussed herein, or alternatively, in the form of a fusion gene product of the protein with another protein, peptide or the like. The protein or peptide may be a fluorescent protein and/or a fusion protein. For example, a fusion protein with green fluorescence protein (GFP) or a fusion gene product with a peptide such as a histidine tag can also be used. Further, by preparing and using a fusion protein with the TAT peptide derived from the virus HIV, intracellular uptake of the nuclear reprogramming factor through cell membranes can be promoted, thereby enabling induction of reprogramming only by adding the fusion protein to a medium thus avoiding complicated operations such as gene transduction. Since preparation methods of such fusion gene products are well known to those skilled in the art, skilled artisans can easily design and prepare an appropriate fusion gene product depending on the purpose.

In certain embodiments, the agent alters the methylation status of one or more nucleic acid sequences, such as any gene listed in a Table set forth herein.

Expression profiling of reprogrammed somatic cells to assess their pluripotency characteristics may also be conducted. Expression of individual genes associated with pluripotency may also be examined. Additionally, expression of embryonic stem cell surface markers may be analyzed. As used herein, "expression" refers to the production of a material or substance as well as the level or amount of production of a material or substance. Thus, determining the expression of a specific marker refers to detecting either the relative or absolute amount of the marker that is expressed or simply detecting the presence or absence of the marker. As used herein, "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipd, a lipid, a lipoprotein or a small molecule.

Detection and analysis of a variety of genes known in the art to be associated with pluripotent stem cells may include analysis of genes such as, but not limited to OCT4, NANOG, SALL4, SSEA-1, SSEA-3, SSEA-4, TRA-1-60, TRA-1-81, or a combination thereof. iPS cells may express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; β-III-tubulin; γ-smooth muscle actin (γ-SMA); fibroblast growth factor 4 (Fgf4), Cripto, Dax1; zinc finger protein 296 (Zfp296); N-acetyltransferase-1 (Nat1); ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fth117; Sal14; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tell); DPPA3/Stella; DPPA4; as well as other general markers for pluripotency, for example any genes used during induction to reprogram the cell. iPS cells can also be characterized by the down-regulation of markers characteristic of the differentiated cell from which the iPS cell is induced.

As used herein, "differentiation" refers to a change that occurs in cells to cause those cells to assume certain specialized functions and to lose the ability to change into certain other specialized functional units. Cells capable of differentiation may be any of totipotent, pluripotent or multipotent cells. Differentiation may be partial or complete with respect to mature adult cells.

"Differentiated cell" refers to a non-embryonic, non-parthenogenetic or non-pluripotent cell that possesses a particular differentiated, i.e., non-embryonic, state. The three earliest differentiated cell types are endoderm, mesoderm, and ectoderm.

Pluripotency can also be confirmed by injecting the cells into a suitable animal, e.g., a SCID mouse, and observing the production of differentiated cells and tissues. Still another method of confirming pluripotency is using the subject pluripotent cells to generate chimeric animals and observing the contribution of the introduced cells to different cell types. Methods for producing chimeric animals are well known in the art and are described in U.S. Pat. No. 6,642,433, incorporated by reference herein.

Yet another method of confirming pluripotency is to observe cell differentiation into embryoid bodies and other differentiated cell types when cultured under conditions that favor differentiation (e.g., removal of fibroblast feeder layers).

In various aspects of the invention, methylation status is converted to an M value. As used herein an M value, can be a log ratio of intensities from total (Cy3) and McrBC-fractionated DNA (Cy5): positive and negative M values are quantitatively associated with methylated and unmethylated sites, respectively.

In various aspects of the invention large hypomethylated blocks are identified. Hypomethylation is present when there is a measurable decrease in methylation. In some embodiments, a DNA block is hypomethylated when less than 50% of the methylation sites analyzed are not methylated. Methods for determining methylation states are provided herein and are known in the art. In some embodiments methylation status is converted to an M value. As used herein an M value, can be a log ratio of intensities from total (Cy3) and McrBC-fractionated DNA (Cy5): positive and negative M values are quantitatively associated with methylated and unmethylated sites, respectively. M values are calculated as described in the Examples. In some embodiments, M values which range from $-0.5$ to $0.5$ represent unmethylated sites as defined by the control probes, and values from $0.5$ to $1.5$ represent baseline levels of methylation.

Numerous methods for analyzing methylation status of a gene are known in the art and can be used in the methods of the present invention to identify either hypomethylation or hypermethylation of the one or more DMRs. In various embodiments, the determining of methylation status in the methods of the invention is performed by one or more techniques selected from the group consisting of a nucleic acid amplification, polymerase chain reaction (PCR), methylation specific PCR, bisulfite pyrosequenceing, single-strand conformation polymorphism (SSCP) analysis, restriction analysis, microarray technology, and proteomics. As illustrated in the Examples herein, analysis of methylation can be performed by bisulfite genomic sequencing. Bisulfite treatment modifies DNA converting unmethylated, but not methylated, cytosines to uracil. Bisulfite treatment can be carried out using the METHYLEASY bisulfite modification kit (Human Genetic Signatures).

In some embodiments, bisulfite pyrosequencing, which is a sequencing-based analysis of DNA methylation that quantitatively measures multiple, consecutive CpG sites individually with high accuracy and reproducibility, may be used.

It will be recognized that depending on the site bound by the primer and the direction of extension from a primer, that the primers listed above can be used in different pairs. Furthermore, it will be recognized that additional primers can be identified within the hypomethylated blocks, especially primers that allow analysis of the same methylation sites as those analyzed with primers that correspond to the primers disclosed herein.

Altered methylation can be identified by identifying a detectable difference in methylation. For example, hypomethylation can be determined by identifying whether after bisulfite treatment a uracil or a cytosine is present a particular location. If uracil is present after bisulfite treatment, then the residue is unmethylated. Hypomethylation is present when there is a measurable decrease in methylation.

In an alternative embodiment, the method for analyzing methylation of a hypomethylated block can include amplification using a primer pair specific for methylated residues within a DMR. In these embodiments, selective hybridization or binding of at least one of the primers is dependent on the methylation state of the target DNA sequence (Herman et al., *Proc. Natl. Acad. Sci. USA*, 93:9821 (1996)). For example, the amplification reaction can be preceded by bisulfite treatment, and the primers can selectively hybridize to target sequences in a manner that is dependent on bisulfite treatment. For example, one primer can selectively bind to a target sequence only when one or more base of the target sequence is altered by bisulfate treatment, thereby being specific for a methylated target sequence.

Other methods are known in the art for determining methylation status of a hypomethylated block, including, but not limited to, array-based methylation analysis and Southern blot analysis.

Methods using an amplification reaction, for example methods above for detecting hypomethylation or hyprmethylation of one or more hypomethylated blocks, can utilize a real-time detection amplification procedure. For example, the method can utilize molecular beacon technology (Tyagi et al., *Nature Biotechnology*, 14: 303 (1996)) or Taqman™ technology (Holland et al., *Proc. Natl. Acad. Sci. USA*, 88:7276 (1991)).

Also methyl light (Trinh et al., *Methods* 25(4):456-62 (2001), incorporated herein in its entirety by reference), Methyl Heavy (Epigenomics, Berlin, Germany), or SNuPE (single nucleotide primer extension) (see e.g., Watson et al., *Genet Res.* 75(3):269-74 (2000)) Can be used in the methods of the present invention related to identifying altered methylation of DMRs.

As used herein, the term "selective hybridization" or "selectively hybridize" refers to hybridization under moderately stringent or highly stringent physiological conditions, which can distinguish related nucleotide sequences from unrelated nucleotide sequences.

As known in the art, in nucleic acid hybridization reactions, the conditions used to achieve a particular level of stringency will vary, depending on the nature of the nucleic acids being hybridized. For example, the length, degree of complementarity, nucleotide sequence composition (for example, relative GC:AT content), and nucleic acid type, for example, whether the oligonucleotide or the target nucleic acid sequence is DNA or RNA, can be considered in selecting hybridization conditions. An additional consideration is whether one of the nucleic acids is immobilized, for example, on a filter. Methods for selecting appropriate stringency conditions can be determined empirically or estimated using various formulas, and are well known in the art (see, e.g., Sambrook et al., supra, 1989).

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, for example, high stringency conditions, or each of the conditions can be used, for example, for 10 to 15 minutes each, in the order listed above, repeating any or all of the steps listed.

The degree of methylation in the DNA associated with the DMRs being assessed, may be measured by fluorescent in situ hybridization (FISH) by means of probes which identify and differentiate between genomic DNAs, associated with the DMRs being assessed, which exhibit different degrees of DNA methylation. FISH is described, for example, in de Capoa et al. (*Cytometry.* 31:85-92, 1998) which is incorporated herein by reference. In this case, the biological sample will typically be any which contains sufficient whole cells or nuclei to perform short term culture. Usually, the sample will be a sample that contains 10 to 10,000, or, for example, 100 to 10,000, whole cells.

Additionally, as mentioned above, methyl light, methyl heavy, and array-based methylation analysis can be performed, by using bisulfite treated DNA that is then PCR-amplified, against microarrays of oligonucleotide target sequences with the various forms corresponding to unmethylated and methylated DNA.

The term "nucleic acid molecule" is used broadly herein to mean a sequence of deoxyribonucleotides or ribonucleotides that are linked together by a phosphodiester bond. As such, the term "nucleic acid molecule" is meant to include DNA and RNA, which can be single stranded or double stranded, as well as DNA/RNA hybrids. Furthermore, the term "nucleic acid molecule" as used herein includes naturally occurring nucleic acid molecules, which can be isolated from a cell, as well as synthetic molecules, which can be prepared, for example, by methods of chemical synthesis or by enzymatic methods such as by the polymerase chain reaction (PCR), and, in various embodiments, can contain nucleotide analogs or a backbone bond other than a phosphodiester bond.

The terms "polynucleotide" and "oligonucleotide" also are used herein to refer to nucleic acid molecules. Although no specific distinction from each other or from "nucleic acid molecule" is intended by the use of these terms, the term "polynucleotide" is used generally in reference to a nucleic acid molecule that encodes a polypeptide, or a peptide portion thereof, whereas the term "oligonucleotide" is used generally in reference to a nucleotide sequence useful as a probe, a PCR primer, an antisense molecule, or the like. Of course, it will be recognized that an "oligonucleotide" also can encode a peptide. As such, the different terms are used primarily for convenience of discussion.

A polynucleotide or oligonucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template.

In another aspect, the present invention includes kits that are useful for carrying out the methods of the present invention. The components contained in the kit depend on a number of factors, including: the particular analytical technique used to detect methylation or measure the degree of methylation or a change in methylation, and the one or more hypomethylated blocks being assayed for.

Accordingly, the present invention provides a kit for determining a methylation status of one or more hypomethylated blocks of the invention.

To examine DNA methylation (DNAm) on a genome-wide scale, comprehensive high-throughput array-based relative methylation (CHARM) analysis, which is a microarray-based method agnostic to preconceptions about DNAm, including location relative to genes and CpG content was carried out. The resulting quantitative measurements of DNAm, denoted with M, are log ratios of intensities from total (Cy3) and McrBC-fractionated DNA (Cy5): positive and negative M values are quantitatively associated with methylated and unmethylated sites, respectively. For each sample, ~4.6 million CpG sites across the genome of iPS cells, parental somatic cells and ES cells were analyzed using a custom-designed NimbleGen HD2 microarray, including all of the classically defined CpG islands as well as all nonrepetitive lower CpG density genomic regions of the genome. 4,500 control probes were included to standardize these M values so that unmethylated regions were associated, on average, with values of 0. CHARM is 100% specific at 90% sensitivity for known methylation marks identified by other methods (for example, in promoters) and includes the approximately half of the genome not identified by conventional region preselection. The CHARM results were also extensively corroborated by quantitative bisulfite pyrosequencing analysis.

In one aspect of the invention, methylation density is determined for a region of nucleic acid. Density may be used as an indication of a hypomethylated block region of DNA, for example. A density of about 0.2 to 0.7, about 0.3 to 0.7, 0.3 to 0.6 or 0.3 to 0.4, or 0.3, may be indicative of a hypomethylated block (the calculated DNA methylation density is the number of methylated CpGs divided by the total number of CpGs sequenced for each sample). Methods for determining methylation density are well known in the art. For example, a method for determining methylation density of target CpG islands has been established by Luo et al. Analytical Biochemistry, Vol. 387:2 2009, pp. 143-149. In the method, DNA microarray was prepared by spotting a set of PCR products amplified from bisulfite-converted sample DNAs. This method not only allows the quantitative analysis of regional methylation density of a set of given genes but also could provide information of methylation density for a large amount of clinical samples as well as use in the methods of the invention regarding iPS cell generation and detection. Other methods are well known in the art (e.g., Holemon et al., BioTechniques, 43:5, 2007, pp. 683-693).

The present invention is described partly in terms of functional components and various processing steps. Such functional components and processing steps may be realized by any number of components, operations and techniques configured to perform the specified functions and achieve the various results. For example, the present invention may employ various biological samples, biomarkers, elements, materials, computers, data sources, storage systems and media, information gathering techniques and processes, data processing criteria, statistical analyses, regression analyses and the like, which may carry out a variety of functions. In addition, although the invention is described in the medical diagnosis context, the present invention may be practiced in conjunction with any number of applications, environments and data analyses; the systems described herein are merely exemplary applications for the invention.

Methods for analysis according to various aspects of the present invention may be implemented in any suitable manner, for example using a computer program operating on the computer system. An exemplary analysis system, according to various aspects of the present invention, may be implemented in conjunction with a computer system, for example a conventional computer system comprising a processor and a random access memory, such as a remotely-accessible application server, network server, personal computer or workstation. The computer system also suitably includes additional memory devices or information storage systems, such as a mass storage system and a user interface, for example a conventional monitor, keyboard and tracking device. The computer system may, however, comprise any suitable computer system and associated equipment and may be configured in any suitable manner. In one embodiment, the computer system comprises a stand-alone system. In another embodiment, the computer system is part of a network of computers including a server and a database.

The software required for receiving, processing, and analyzing biomarker information may be implemented in a single device or implemented in a plurality of devices. The software may be accessible via a network such that storage and processing of information takes place remotely with respect to users. The analysis system according to various aspects of the present invention and its various elements provide functions and operations to facilitate biomarker analysis, such as data gathering, processing, analysis, reporting and/or diagnosis. The present analysis system maintains information relating to methylation and samples and facilitates analysis and/or diagnosis, For example, in the present embodiment, the computer system executes the computer program, which may receive, store, search, analyze, and report information relating to the epigenome. The computer program may comprise multiple modules performing various functions or operations, such as a processing module for processing raw data and generating supplemental data and an analysis module for analyzing raw data and supplemental data to generate a disease status model and/or diagnosis information.

The procedures performed by the analysis system may comprise any suitable processes to facilitate analysis and/or disease diagnosis. In one embodiment, the analysis system is configured to establish a disease status model and/or determine disease status in a patient. Determining or identifying disease status may comprise generating any useful information regarding the condition of the patient relative to the disease, such as performing a diagnosis, providing information helpful to a diagnosis, assessing the stage or progress of a disease, identifying a condition that may indicate a susceptibility to the disease, identify whether further tests may be recommended, predicting and/or assessing the efficacy of one or more treatment programs, or otherwise assessing the disease status, likelihood of disease, or other health aspect of the patient.

The analysis system may also provide various additional modules and/or individual functions. For example, the analysis system may also include a reporting function, for example to provide information relating to the processing and analysis functions. The analysis system may also provide various administrative and management functions, such as controlling access and performing other administrative functions.

The analysis system suitably generates a disease status model and/or provides a diagnosis for a patient based on raw biomarker data and/or additional subject data relating to the subjects. The data may be acquired from any suitable biological samples.

The following examples are provided to further illustrate the advantages and features of the present invention, but are not intended to limit the scope of the invention. While they are typical of those that might be used, other procedures, methodologies, or techniques known to those skilled in the art may alternatively be used.

Example 1

Large-Scale Epigenomic Reprogramming Links Anabolic Glucose Metabolism to Distant Metastasis During the Evolution of Pancreatic Cancer Progression Background and Hypothesis As discussed previously, one prometastatic candidate is epigenomic regulation. In particular, we wished to investigate the role of large-scale epigenomic changes during PDAC subclonal evolution and distant metastasis, especially within heterochromatin domains including large organized heterochromatin lysine (K)-9 modified domains (LOCKs) and large DNA hypomethylated blocks. These regions could represent selectable targets for large-scale epigenetic reprogramming, since they occupy over half of the genome, partially overlap with one another, and are found in many human cancers including PDAC. The inventors therefore hypothesized that epigenomic dysregulation within these regions could be a major selective force for tumor progression, given the lack of any consistent metastasis-specific driver mutations.

Results

Reprogramming of Global Epigenetic State During the Evolution of Distant Metastasis To test this hypothesis, we first determined whether large-scale changes in epigenetic modifications could be detected during PDAC evolution in patient samples in vivo. We previously collected matched primary and metastatic PDAC lesions from individual patients by rapid autopsy, and reported the genetic progression of subclonal evolution by whole exome and sanger sequencing for mutations, paired-end sequencing for rearrangements, and whole genome sequencing in a subset of these samples. These samples represent a unique resource especially suited to study tumor evolution, since they were collected from matched primary and metastatic tumors from the same patient(s), each has been deep sequenced, individual subclones have been identified, and no metastasis-specific driver mutations are present. From these patients, we selected a large panel of diverse PDAC samples to test for global epigenomic reprogramming during subclonal evolution. As summarized in Table 1, these samples were chosen because they represented the diversity of PDAC evolution (different regions of primary tumor paired to peritoneal and distant metastases), each sample represented a sequence-verified (sub)clonal population, patients were both treated and untreated, driver mutations were shared by all subclones in each patient in the absence of metastasis-specific drivers, formalin-fixed tissue was available for immunoassays, frozen tissue was available for whole-genome bisulfite sequencing, and cell lines were available for all other experiments.

TABLE 1

PDAC sample characteristics with LOCK epigenetic changes

| Sample (Clonal Relation[a]) | Disease Present. | Source | Driver Genes (in primary and mets) | Chemo | Assays[b] IHC, Western Blots, ChIP-seq, WGBS | Results[b] LOCK Methylation Change |
|---|---|---|---|---|---|---|
| A124PrF (Founder Clone) | Local-regional | Tissue: Primary Tumor | KRAS CDKN2A SMAD4 ATM | Untreated | K9Me2/3 IHC: | Diffusely Positive |
| A124PrS (Subclone) | Local-regional | Tissue: Primary Tumor | KRAS CDKN2A SMAD4 ATM | Untreated | K9Me2/3 IHC: WGBS: | Diffusely Positive High (75%, control) |
| A124Per (Metastasis) | Local-regional | Tissue: Peritoneum | KRAS CDKN2A SMAD4 ATM | Untreated | K9Me2/3 IHC: WGBS: | Diffusely Positive High (74%) |
| A141PrF (Founder Clone) | Local-regional | Tissue: Primary Tumor | KRAS CDKN2A TP53 MLL3 ARID1B | Untreated | K9Me2/3 IHC: | Diffusely Positive |
| A141PrS (Subclone) | Local-regional | Tissue: Primary Tumor | KRAS CDKN2A TP53 MLL3 ARID1B | Untreated | K9Me2/3 IHC: | Diffusely Positive |
| A141Per (Metastasis) | Local-regional | Tissue: Peritoneum | KRAS CDKN2A TP53 MLL3 ARID1B | Untreated | K9Me2/3 IHC: | Diffusely Positive |
| A125PrF (Founder Clone) | Distant metastases | Tissue: Primary Tumor | KRAS CDKN2A TP53 ARID1A | Untreated | K9Me2/3 IHC: WGBS: | Diffusely Positive High (74%) |
| A125PrS (Subclone) | Distant metastases | Tissue: Primary Tumor | KRAS CDKN2A TP53 ARID1A | Untreated | K9Me2/3 IHC: WGBS: | Positive + Negative Reduced (51%) |
| A125Lv1 (Metastasis) | Distant metastases | Tissue: Liver | KRAS CDKN2A TP53 ARID1A | Untreated | K9Me2/3 IHC: WGBS: | Diffusely Negative Reduced (57%) |
| A125Lv2 (Metastasis) | Distant metastases | Tissue: Liver | KRAS CDKN2A TP53 ARID1A | Untreated | K9Me2/3 IHC: WGBS: | Diffusely Negative Reduced (59%) |
| A132PrF (Founder Clone) | Distant metastases | Tissue: Primary Tumor | KRAS CDKN2A TP53 ATM | Untreated | K9Me2/3 IHC: | Diffusely Positive |
| A132PrS (Subclone) | Distant metastases | Tissue: Primary Tumor | KRAS CDKN2A TP53 ATM | Untreated | K9Me2/3 IHC: | Positive + Negative |
| A132Lv (Metastasis) | Distant metastases | Tissue: Liver | KRAS CDKN2A TP53 ATM | Untreated | K9Me2/3 IHC: | Positive + Negative |
| A38PrF (Founder Clone) | Local-regional + Distant metastases | Tissue: Primary Tumor | KRAS TP53 SMAD4 | Gem. Bev. | K9Me2/3 IHC: | Diffusely Positive |
| A38PrS1 (Peritoneal Precursor Subclone) | Local-regional + Distant metastases | Tissue: Primary Tumor | KRAS TP53 SMAD4 | Gem. Bev. | K9Me2/3 IHC: | Diffusely Positive |
| A38PrS2 (Liver/Lung Precursor Subclone) | Local-regional + Distant metastases | Tissue: Primary Tumor | KRAS TP53 SMAD4 SMARCA2[c] | Gem. Bev. | K9Me2/3 IHC: | Positive + Negative |
| A38Lg1 (Metastasis) | Local-regional + Distant metastases | Tissue: Lung | KRAS TP53 SMAD4 | Gem. Bev. | K9Me2/3 IHC: | Diffusely Negative |

TABLE 1-continued

PDAC sample characteristics with LOCK epigenetic changes

| Sample (Clonal Relation[a]) | Disease Present. | Source | Driver Genes (in primary and mets) | Chemo | Assays[b] IHC, Western Blots, ChIP-seq, WGBS | Results[b] LOCK Methylation Change |
|---|---|---|---|---|---|---|
| A38Per (Metastasis) | Local-regional + Distant metastases | Cell Line: Peritoneum | KRAS TP53 SMAD4 | Gem. Bev. | K9Me2 Western Blot: K9Me2 ChIP-seq: WGBS: | High (100%, cont.) High (100%, cont.) High (79%, cont.) |
| AsPC1[d] (N/A) | Local-regional | Cell Line: Ascites | KRAS CDKN2A TP53 SMAD4 | Gem. | K9Me2 Western Blot: | High (102%) |
| HPAFII[d] (N/A) | Local-regional | Cell Line: Ascites | KRAS TP53 | Gem. | K9Me2 Western Blot: | High (94%) |
| Capan2[d] (N/A) | Local-regional | Cell Line: Primary Tumor | KRAS CDKN2A TP53 | Gem. | K9Me2 Western Blot: | High (93%) |
| A2Lg (Metastasis) | Local-regional + Distant metastases | Cell Line: Lung | KRAS TP53 | Taxoprex. Gem. | K9Me2 Western Blot: | Reduced (40%) |
| A2Lv (Metastasis) | Local-regional + Distant metastases | Cell Line: Liver | KRAS TP53 | Taxoprex. Gem. | K9Me2 Western Blot: | Reduced (50%) |
| A6Lv (Metastasis) | Local-regional + Distant metastases | Cell Line: Liver | KRAS TP53 MLL3 | Gem. Trox. | K9Me2 Western Blot: | Reduced (47%) |
| A10Lv (Metastasis) | Distant metastases | Cell Line: Liver | KRAS TP53 MLL3 | Untreated | K9Me2 Western Blot: | Reduced (61%) |
| A13Pr1 (Subclone) | Distant metastases | Cell Line: Primary Tumor | KRAS CDKN2A MYC TP53 | Untreated | K9Me2 Western Blot: K9Me2 ChIP-seq: WGBS: | Reduced (64%) Reduced (25%) Reduced (72%) |
| A13Pr2 (Subclone) | Distant metastases | Cell Line: Primary Tumor | KRAS CDKN2A MYC TP53 | Untreated | K9Me2 Western Blot: K9Me2 ChIP-seq: WGBS: | Reduced (51%) Reduced (81%) Reduced (73%) |
| A13Lg (Metastasis) | Distant metastases | Cell Line: Lung | KRAS CDKN2A MYC TP53 | Untreated | K9Me2/3 Western Blot: K9Me2 ChIP-seq: WGBS: | Reduced (53%) Reduced (86%) Reduced (71%) |
| A32O (Metastasis) | Local-regional + Distant metastases | Cell Line: Omentum[e] | KRAS TP53 | 5-FU | K9Me2 Western Blot: | Reduced (58%) |
| A38Lv (Metastasis) | Local-regional + Distant metastases | Cell Line: Liver | KRAS TP53 SMAD4 | Gem. Bev. | K9Me2 Western Blot: WGBS: | Reduced (47%) Reduced (67%) |

TABLE 1-continued

PDAC sample characteristics with LOCK epigenetic changes

| Sample (Clonal Relation[a]) | Disease Present. | Source | Driver Genes (in primary and mets) | Chemo | Assays[b] IHC, Western Blots, ChIP-seq, WGBS | Results[b] LOCK Methylation Change |
|---|---|---|---|---|---|---|
| A38Lg (Metastasis) | Local-regional + Distant metastases | Cell Line: Lung | KRAS TP53 SMAD4 | Gem. Bev. | K9Me2 Western Blot: K9Me2 ChIP-seq: WGBS: | Reduced (58%) Reduced (48%) Reduced (72%) |

Figure 1C:
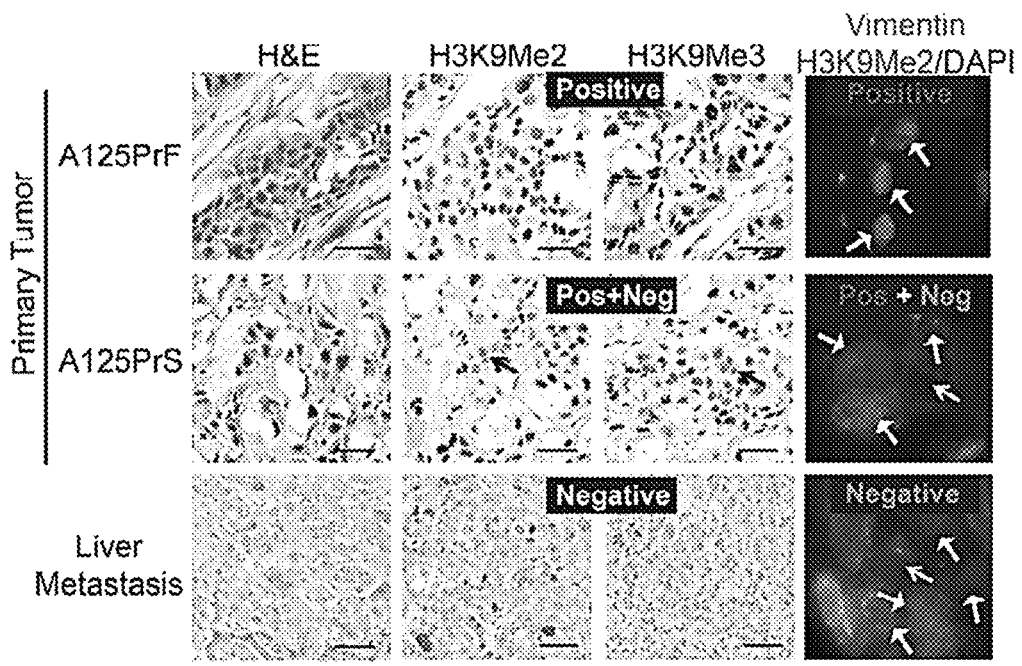
Figure 1D:
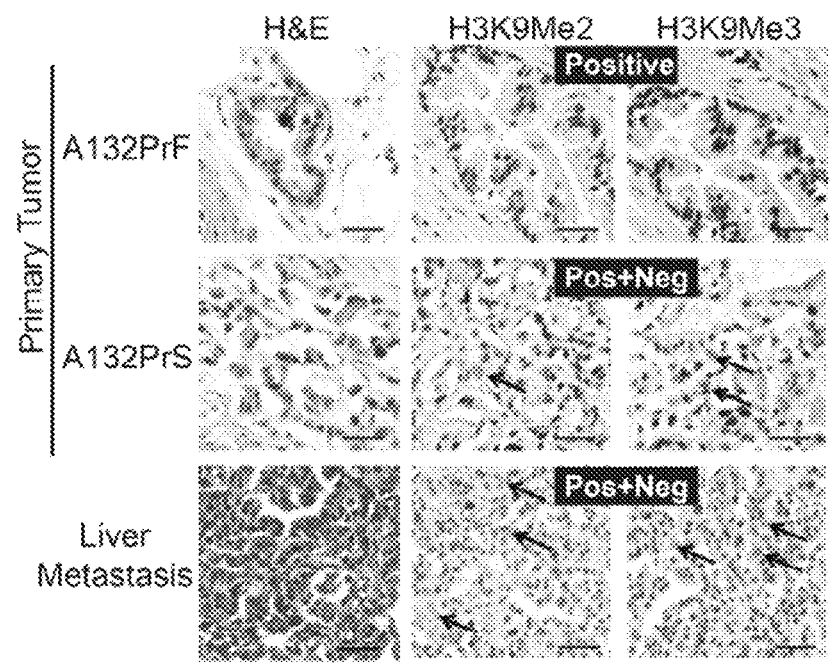
Figure 1E:
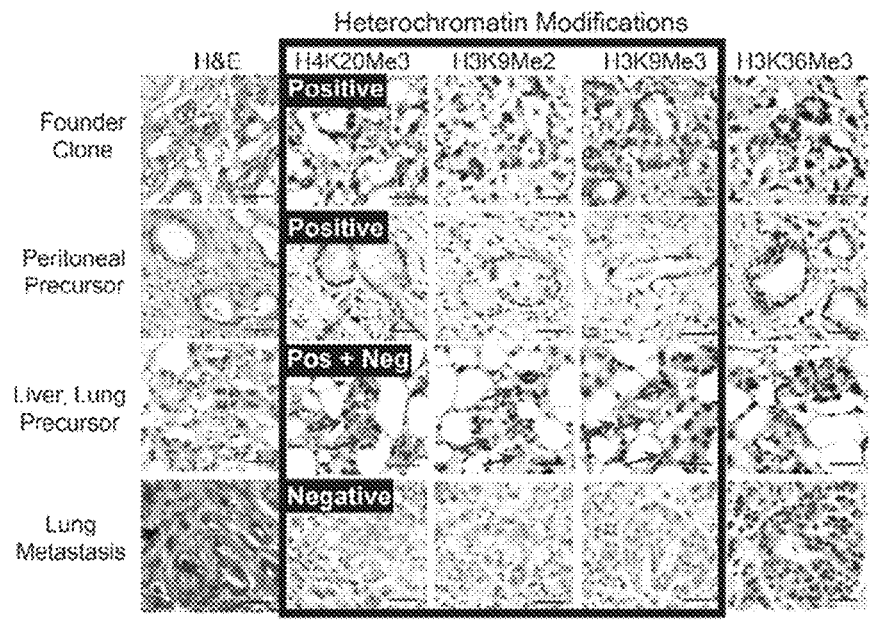
Figure 1F:
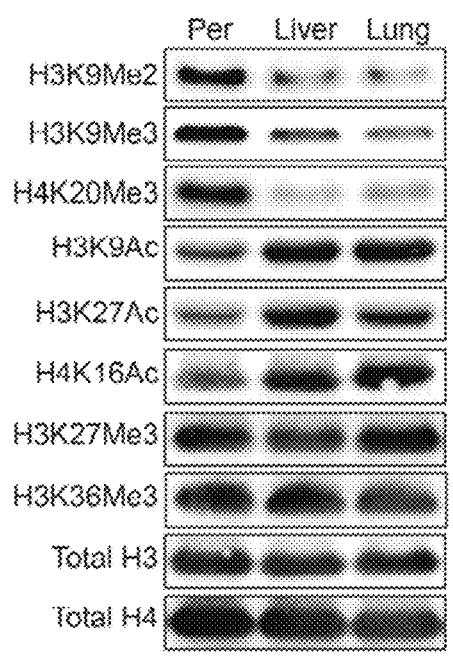
FIG. 1F is a series of western blot images.
Figure 1G:
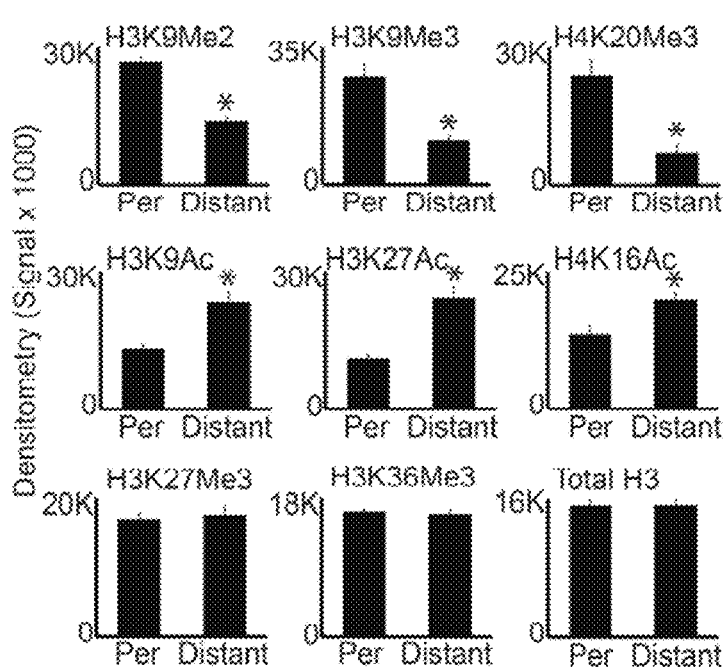
FIG. 1G is a series of graphical representations data.

Table 1: Summary of H3K9 and DNA methylation changes across tissue and cell line samples. Samples from patients with local-regional spread (peritoneal/ascites) showed relatively high global H3K9/DNA methylation as indicated by multiple assays (right two columns), while samples from patients with distant metastases showed reduced methylation across all assays, which initiated in primary tumors as indicated.
Abbreviations:
Gem. (Gemcitabine), Bev. (Bevacizumab), Taxoprex. (Taxoprexin), Trox. (Troxacitabine).
Superscript Notes
[a]Clonal origins represent phylogenetic estimates from previously published (ref. 1) and other unpublished (text footnote 1) whole-genome sequencing data.
[b]Western blot data reflect densitometry percentages of H3K9Me2 signals relative to A38Per controls (cont.). Western blots are shown in Supplementary FIG. 1 and the absolute densitometry values are shown in FIG. 1g with p-values included in the figure legend. ChIP-seq data reflect percent of LOCK Mb with reduced H3K9Me2 relative to A38Per controls (cont.), as detailed with Mb and RPKM values in Supplementary Data File 2. WGBS data reflect percent of DNA methylation within LOCKs relative to A124Pr controls (tissues) and A38Per controls (cell lines), as detailed in Supplementary FIGS. 1 and 2.
[c]This metastasis from a chemotherapy-treated patient had a missense mutation in SMARCA2 of unclear significance.
[d]These cell lines were not from the rapid autopsy cohort and rely on previously published genotyping data which may underestimate the driver mutations.
[e]The A32O cell line was isolated from an omental mass lesion in a patient with very aggressive disease including widespread lung metastases, and showed findings similar to the other distant (lung/liver) metastatic subclones.

We began our analysis with the formalin-fixed tissue samples (totaling 16 uniquely matched, sequence-verified tumor sections, Table 1). We performed immunostains against heterochromatin modifications (e.g. H3K9Me2/3) in order to detect global changes from heterochromatin domains (including LOCKs as defined in Wen et al. (Large histone H3 lysine 9 dimethylated chromatin blocks distinguish differentiated from embryonic stem cells. Nat Genet 41, 246-50 (2009)), and McDonald et al. (Genome-scale epigenetic reprogramming during epithelial-to-mesenchymal transition. Nat Struct Mol Biol 18, 867-74 (2011))) that might be selectable targets during subclonal evolution. Immunostains revealed diffusely positive (>80%) H3K9Me2/3 staining of PDAC cell nuclei across both primary tumor and peritoneal metastatic subclones from patients who presented with peritoneal carcinomatosis (FIG. 1a, b and Table 1). In contrast, samples from patients who presented with distant metastatic disease displayed progressive loss of H3K9Me2/3 during subclonal evolution. This manifested as heterogeneous (mixtures of positive+negative PDAC nuclei) staining in primary tumors followed by either diffusely negative (<20%) staining or retention of heterogeneous staining in the paired metastases (FIG. 1c, d and Table 1). We also observed similar results during subclonal evolution from a patient for which sequence-verified primary tumor subclones that seeded both peritoneal and distant metastases were available. The peritoneal precursor retained diffusely strong staining of heterochromatin modifications as seen in the clone that founded the neoplasm (FIG. 1e, top two panels). In contrast, cell-to-cell heterogeneity of staining patterns emerged in the primary tumor subclone that seeded distant metastasis, followed by diffuse loss of staining at the distant metastatic site (FIG. 1e, bottom two panels). The collective findings across samples from patients with distant metastatic disease thus suggested that reprogramming initiated during subclonal evolution in the primary tumor, and that these changes were inherited or even accentuated in subclones that formed tumors at the distant metastatic sites themselves.

To expand our analysis to more patient samples and test the generality of our findings, we employed twelve low-passaged cell lines collected from eight patients (Table 1), including a subset that corresponded to the patient tissues above. Cell lines were isolated from nine distant metastatic subclones, a peritoneal metastasis with paired liver and lung metastases that corresponded to the patient presented in FIG. 1e, and two (non-founder) primary tumor subclones matched to a lung metastasis collected from the same patient. Importantly, six of the nine distant metastatic cell lines were previously whole exome sequenced, and mutations present in the cell lines were also present in the corresponding patient tissues as detected by sanger sequencing. Because rapid autopsy cell lines were largely isolated from patients who presented with distant metastases, additional PDAC samples from other sources of regional disease were also included: malignant ascites fluid from two patients with peritoneal carcinomatosis (AsPC1, HPAFII), and a primary tumor from a long-term survivor without distant metastases (Capan2).

Figures 7A, 7B, 7C:
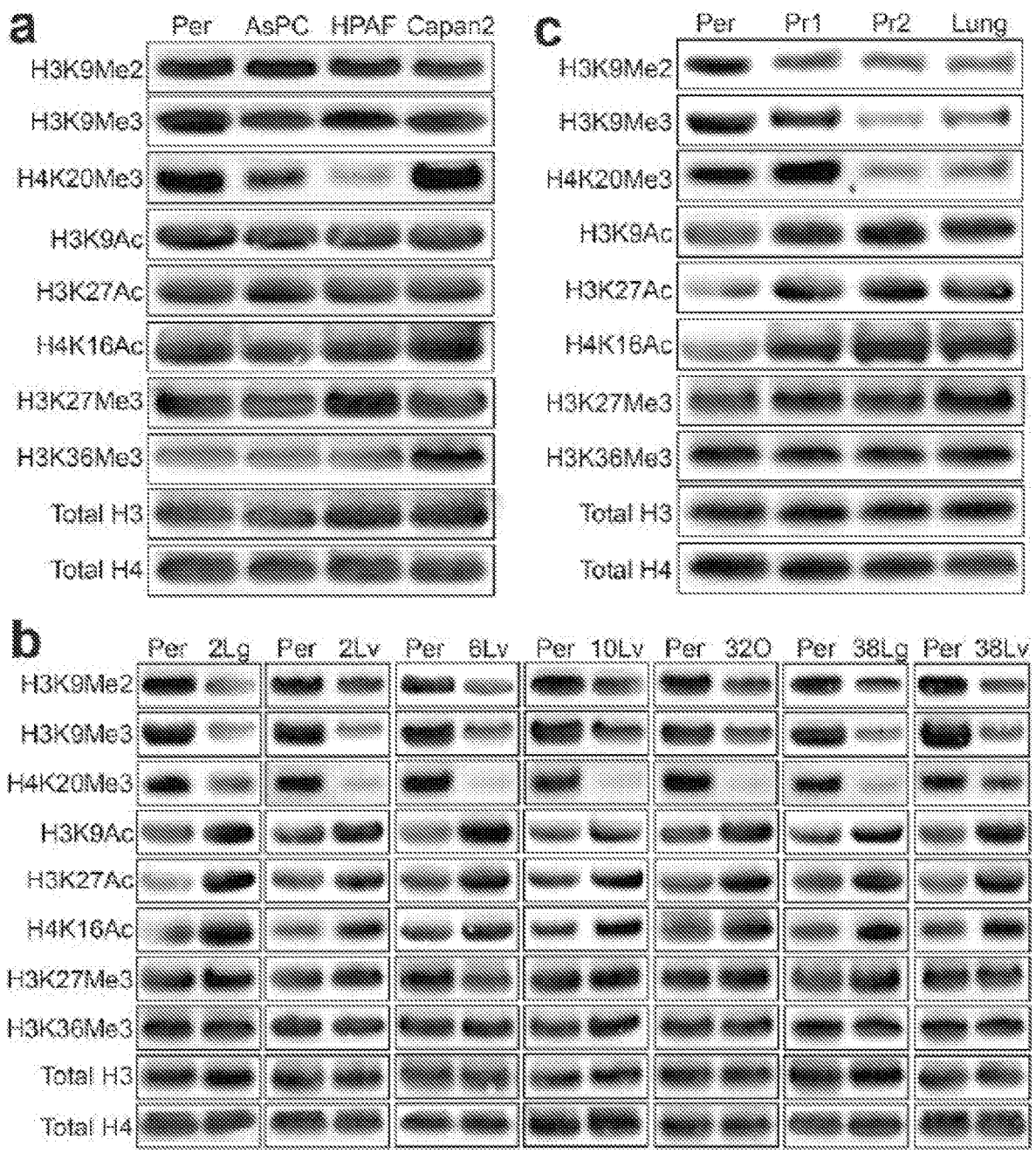
FIGS. 7A-7B relate to reprogrammed chromatin across distant metastatic subclones.
FIG. 7C is a series of western blot images.
Figures 8A, 8B, 8C, 8D, 8E:
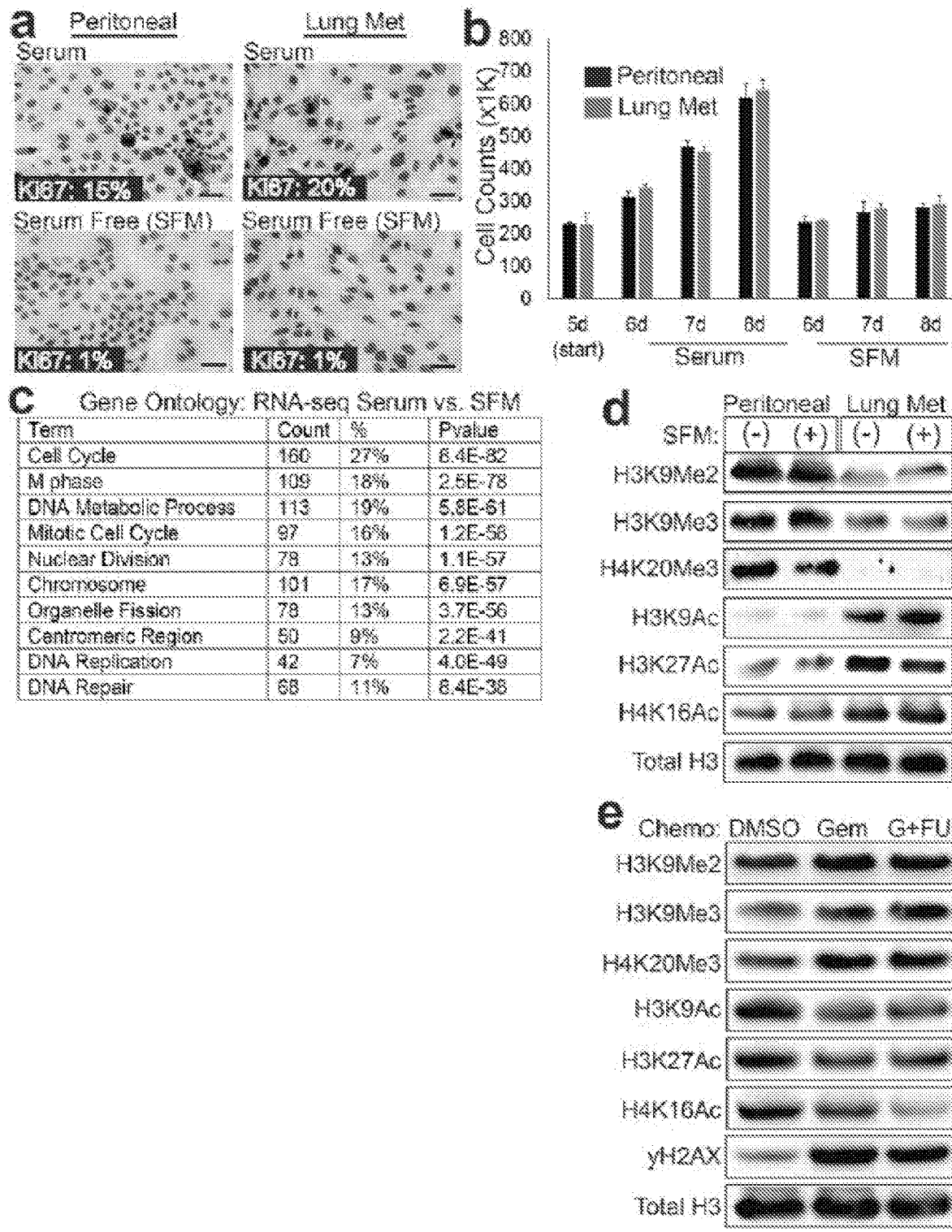
FIGS. 8A-8E relate to specificity of reprogrammed histone modifications.

We then examined whether global changes in chromatin as seen in the patient tissues were maintained in cell lines, which could reflect genome-wide reprogramming events. We began by performing western blots for eight histone modifications with well-understood functions. Comparison of local-regional PDAC samples (A38Per, AsPC1, HPAFII, Capan2) by western blots showed minimal or non-recurrent global changes across all histone modifications tested (FIG. 7a), similar to the evolution of peritoneal carcinomatosis observed in patient tissues. In contrast, distant metastases displayed striking reprogramming of methylation and acetylation that was targeted to specific histone residues (FIG. 7b), including between the paired peritoneal (A38Per) and distant metastatic (A38Lv, A38Lg) subclones that corresponded to the patient presented in FIG. 1e (FIG. 1f). This manifested as recurrent reductions in H3K9Me2/3 and H4K20Me3 that was coupled to hyper-acetylation of H3K9Ac and H3K27Ac in distant metastases (summarized in FIG. 1g and Table 1, shown in FIG. 7b). H3K9 methylation is critical for encoding heterochromatic epigenetic states over large genomic regions including LOCKs, and H3K27Ac encodes gene regulatory elements. Reprogramming appeared specific, as we observed no consistent/ recurrent changes in H3K27Me3 or H3K36Me3 across samples (FIG. 1g, FIG. 7) and the reprogrammed modifications themselves were not dependent on proliferation rates and could not be induced by PDAC chemotherapy (FIG. 8). Finally, western blots on cell lines isolated from matched primary tumor (A13Pr1, A13Pr2) and distant metastatic (A13Lg) subclones collected from a patient who presented with widespread distant metastases in the absence of regional (peritoneal) spread also showed reductions in H3K9Me3 and H4K20Me3 between the primary tumor subclones, which was retained in the distant metastasis (FIG. 7c), further suggesting that reprogramming initiated in the primary tumor during the evolution of distant metastasis. Thus, in vivo tissue and in vitro cell culture findings across the collective 30 patient samples strongly suggested that global epigenetic state was reprogrammed during the evolution of distant metastasis.

The Epigenomic Landscape of PDAC Subclonal Evolution

We next wished to map the locations of reprogrammed chromatin modifications across the PDAC genome. To this end, we comprehensively mapped the epigenetic landscape of PDAC evolution with chromatin immunoprecipitation followed by high-throughput sequencing (ChIP-seq) for histone modifications with well-understood functions (heterochromatin: H3K9Me2, H3K9Me3, H3K27Me3; euchromatin: H3K27Ac, H3K36Me3). To capture the diversity of subclonal evolution and malignant progression, ChIP-seq was performed on sequence-verified cell lines isolated from matched subclones, including a peritoneal metastasis (A38Per) matched to a lung metastasis (A38Lg) from the same patient, and two primary tumor subclones (A13Pr1, A13Pr2) that were also matched to a lung metastasis (A13Lg) from the same patient. For each patient, all subclones shared identical driver gene mutations without acquisition of new metastasis-specific drivers (Table 1). We also performed RNA-seq in parallel to identify matched gene expression changes. Finally, we complemented these datasets with whole genome bisulfite sequencing (WGBS) across these cell lines and frozen tumor tissues that corresponded to a subset of the formalin-fixed tumor sections presented in FIG. 1. In all, we generated 183 datasets with $19.3 \times 10^9$ uniquely aligned sequencing reads, including $>15.0 \times 10^6$ (median: $32.3 \times 10^6$) uniquely aligned reads for each ChIP experiment as recommended by ENCODE guidelines (Supplementary Data 1). Experiments were performed as biological replicates, with good correlation between replicates (median correlation coefficient: 0.956; range: 0.746-0.997, Supplementary Data 1). To our knowledge, this represents the first comprehensive genome-wide analysis of epigenetic reprogramming during the evolutionary progression of a human cancer.

Because global chromatin modifications were stably inherited during the evolution of peritoneal carcinomatosis whereas reprogramming emerged during distant metastasis, we began by comparing the peritoneal subclone against the distant metastatic subclones and their matched primary tumor subclones. This analysis revealed a striking and unexpected degree of genome-wide epigenetic reprogramming that was targeted to thousands of chromatin domains covering >95% of the PDAC genome. These included heterochromatin regions corresponding to large organized chromatin lysine (K)-modified domains (LOCKs) that occupied approximately half the genome, gene-rich euchromatin domains (ECDs), and a smaller subset of very large LOCK domains that were uniquely reprogrammed compared to other heterochromatin regions. The collective domain characteristics are detailed in Supplementary Data 2, and comprehensive statistical analyses across experiments are presented in Supplementary Data 3.

Figure 9:
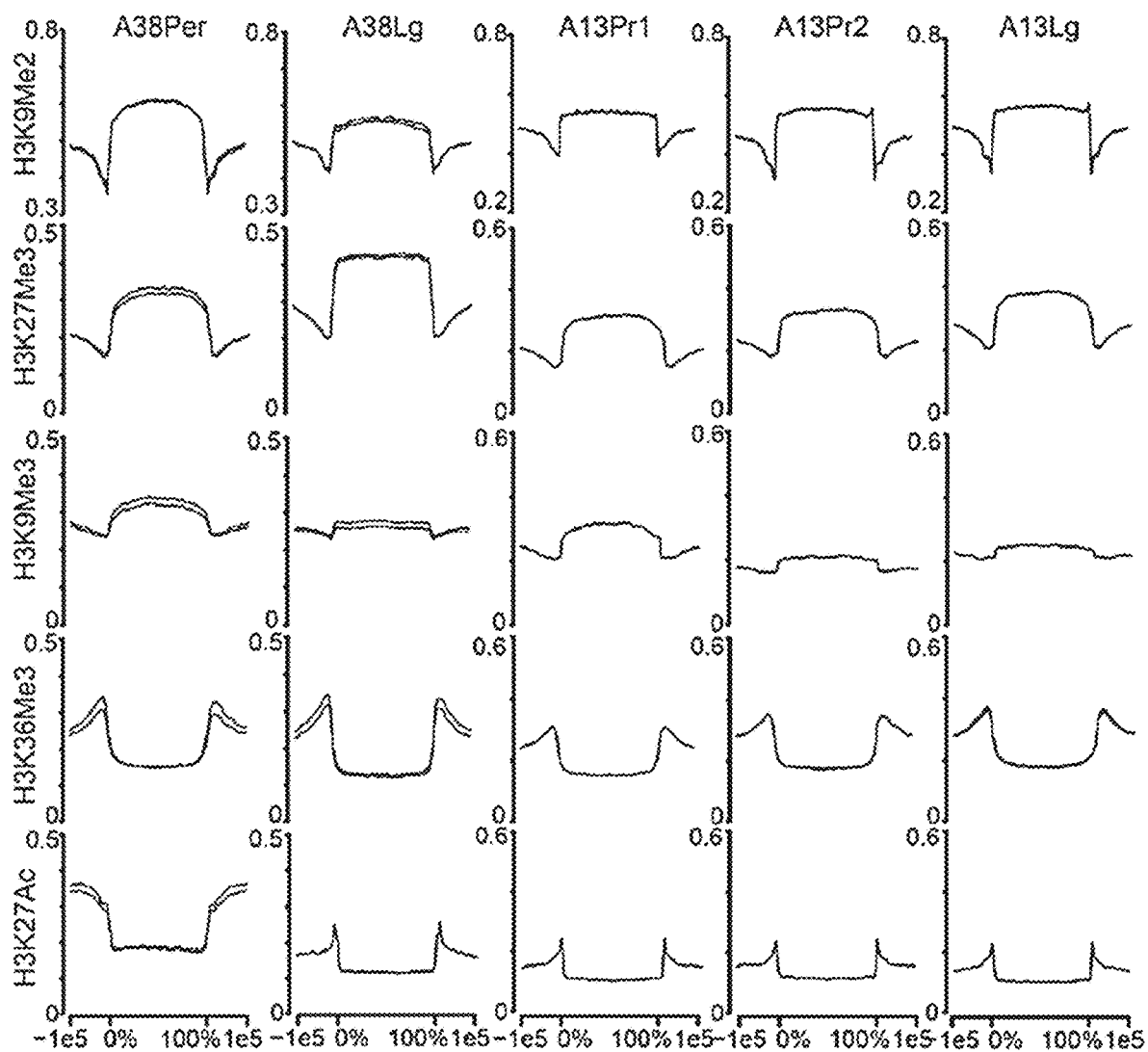
FIG. 9 is a series of graphical plots relating to enrichment of heterochromatin modifications within LOCKs.
Figure 10A:
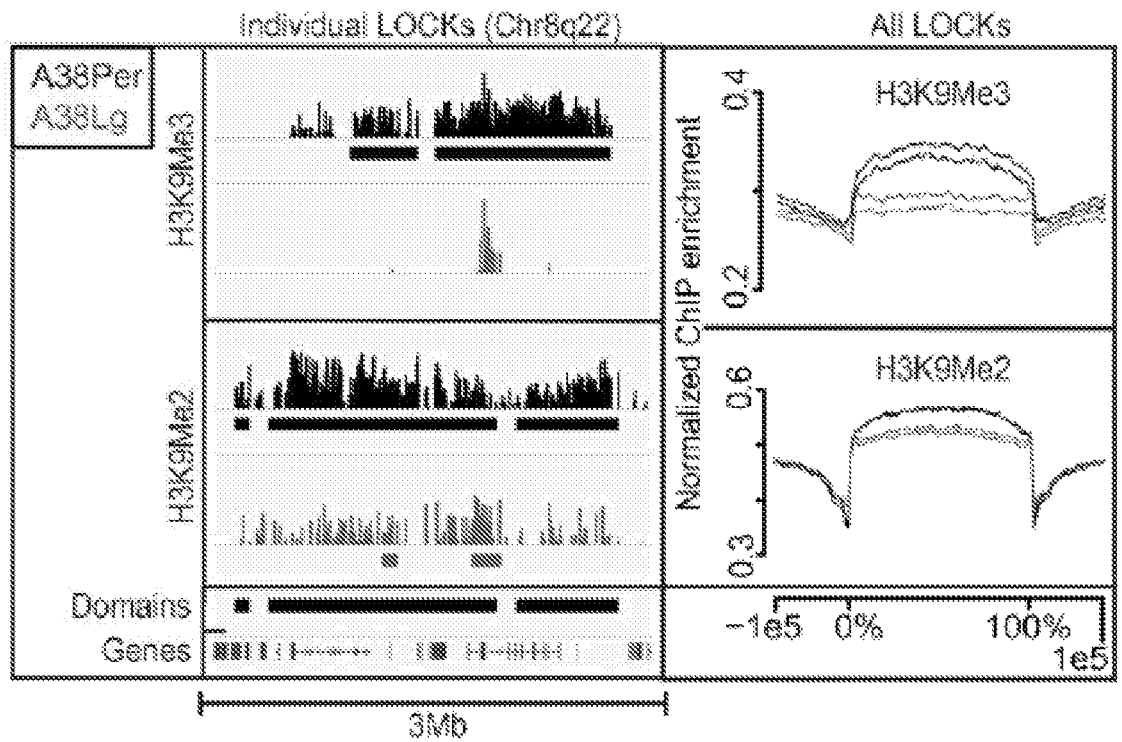
FIGS. 10A-10B relate to reprogramming of H3K9Me3 in LOCKs during PDAC subclonal evolution.
Figure 10B:
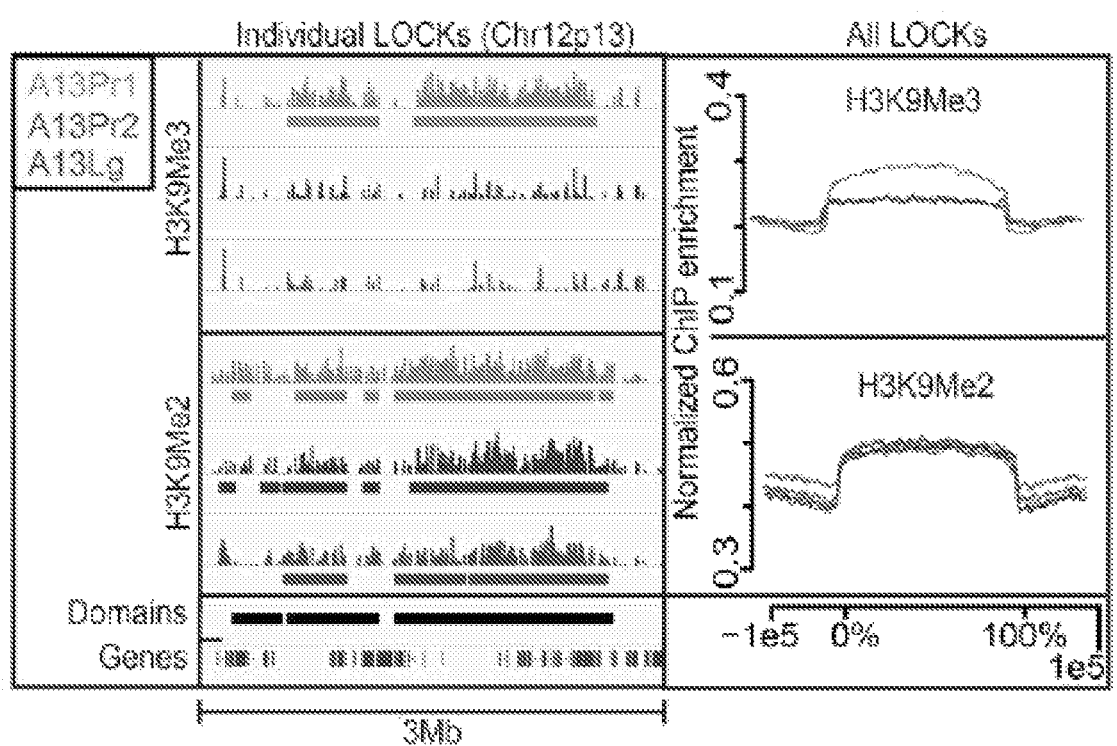

We first analyzed heterochromatin domains defined by strong, broad enrichments of H3K9Me2 and H3K27Me3 with depletion of euchromatin modifications (FIG. 2a, FIG. 9, and Supplementary methods). Thousands of heterochromatin domains were detected in each sample (range: 2,008-3,166) and were organized into large block-like segments (median lengths: 232 Kb-311 Kb) that occupied more than half of the genome in each subclone (average: 61.7% of the genome, range: 54.1-71.7%, Supplementary Data 2). The domain calls were robust as determined by sensitivity analyses across multiple thresholds (Supplementary Data 3), and the called heterochromatin regions themselves overlapped significantly with previously reported LOCK heterochromatin domains (avg: 76.7+/−16.9% overlap; p<0.01 by permutation testing), suggesting that heterochromatin largely corresponded to LOCKs. Similar to immunostain (FIG. 1a-d) and western blot data (FIG. 1e, f), we detected strong H3K9Me2 enrichment across LOCKs in the peritoneal subclone, whereas these same regions displayed global reductions of H3K9Me2 in the distant metastases and their matched primary tumor subclones (FIG. 2a, average: 591 Mb/1,470 Mb; range: 204-1,110 Mb/1,470 Mb; p<2.2e-16 by chi square; Table 1 and Supplementary Data 3). In contrast, high global levels of H3K27Me3 were detected from these regions across all subclones (FIG. 2a), similar to the western blot findings (FIG. 1g). We also detected patient-specific patterns of global H3K9Me3 reprogramming in LOCKs (FIG. 10). In patient A38, H3K9Me3 was largely absent from A38Lg LOCKs relative to A38Per (loss of H3K9Me3 from 184/208 Mb, 88.5%, p<2.2e-16). Loss of LOCK-wide H3K9Me3 was also detected between the paired primary tumor subclones in patient A13 (106 Mb/118 Mb, 90.0% in A13Pr2 vs. A13Pr1, p<2.2e-16), and similar to western blot findings (Supplementary FIG. 1c) this change was inherited in the distant metastatic subclone (152 Mb/169 Mb, 90.2% in A13Lg vs. A13Pr1, p<2.2e-16). Finally, localized reprogramming events were also detected specifically within chromatin encoding differentially expressed (DE) genes in LOCKs (FIG. 11, Supplementary Data 3). This included reciprocal changes in H3K27Ac and H3K9Me2 over promoters coupled to similar reciprocal changes in H3K36Me3 and H3K27Me3 over gene bodies of LOCK genes that were up- and down-regulated. This suggested that DE genes from LOCKs were situated in specific sub-regions that possessed gene regulatory potential, consistent with hybrid LOCK-euchromatin islands (LOCK-EIs). Collectively, these findings indicated that heterochromatin domains (LOCKs) represented a major target for both global and local chromatin reprogramming events during the evolution of distant metastasis.

Because LOCKs correspond to a subset of block-like regions that are DNA hypomethylated in pancreatic and other human cancers, we also asked whether DNA methylation changes were targeted to LOCKs during PDAC subclonal evolution. For this analysis, we performed WGBS on all of the cell lines with ChIP-seq data reported above. Because frozen tissues corresponding to the cell lines had been exhausted during previous studies, we selected 7 other frozen tissue samples for in vivo WGBS that were uniquely matched to the same formalin-fixed tissues with IHC data presented in FIG. 1a (A124, local-regional spread) and FIG. 1c (A125, distant metastasis). Normal pancreas was included with frozen tissue samples as an internal control. All samples and results of WGBS with corresponding IHC, western blot, and ChIP-seq findings are summarized in Table 1, and quantified WGBS results with statistical analyses are presented in Tables 2 and 3. These experiments revealed significant reductions in LOCK-wide DNA methylation across cell lines isolated from distant metastases relative to peritoneal carcinomatosis (FIG. 2b, c, Table 3). These findings matched the reductions of H3K9Me2 in LOCKs detected by ChIP-seq on the same samples (FIG. 2a), revealing that reprogramming of DNA methylation in hypomethylated block regions is targeted to LOCKs with reprogrammed histone methylation (Table 1). Analysis of the same LOCK regions from the frozen tissue samples also revealed relatively high DNA methylation in LOCKs from patient A124 (peritoneal spread) and the founder clone from patient A125, while the primary tumor and distant metastatic subclone descendants displayed striking loss of DNA methylation that was even more pronounced than that seen in the cell lines (FIG. 2b, c, Table 1, and Table 2). We also detected strong, localized DNA hypomethylation from down-regulated DE genes in the hybrid LOCK-EI sub-regions, while up-regulated genes remained hypermethylated with sharp dips at the 5'-ends of genes, similar to H3K9Me2 (FIG. 11). Thus, DNA methylation was globally and locally reprogrammed across LOCKs from primary tumor and distant metastatic subclones, similar to histone modifications. Based on the collective immunostain (FIG. 1a-e), western blot (FIG. 1f, g), ChIP-seq (FIG. 2a), and WGBS (FIG. 2b, c) data (Summarized in Table 1), we conclude that a substantial fraction of global reprogramming events was targeted to heterochromatin domains (LOCKs) during the evolution of distant metastasis.

TABLE 2

Percent CpG Methylation levels across LOCK domains detected in frozen tissue samples by WGBS. DNA methylation levels were relatively high in both primary tumor and metastatic tumors from patient A124, who presented with peritoneal carcinomatosis. Similar high levels of DNA methylation were also detected in the founder clone from patient A125, which were significantly reduced in the primary tumor subclone that seeded distant metastases and in the liver metastases themselves. P-values were calculated with paired wilcox tests using a 3% threshold.

| Samples<br>Sample name<br>Sample source | Global LOCK Methylation<br>% CpG Methylation in<br>LOCKs by WGBS | Significant Difference<br>p-value vs. A124Pr |
| --- | --- | --- |
| A124PrF<br>Primary Tumor | 75.37% | N/A<br>(Highest Methylation) |
| A124Per<br>Peritoneal Met | 74.17% | 1 |
| A125PrF<br>Primary Tumor #1<br>(Founder Clone) | 73.65% | 1 |
| A125PrS<br>Primary Tumor #2<br>(Subclone) | 51.12% | 2.20E−16 |
| A125Lv1<br>Liver Met #1 | 56.95% | 2.20E−16 |
| A125Lv2<br>Liver Met #2 | 59.47% | 2.20E−16 |
| Normal Pancreas | 67.75% | 2.20E−16 |

TABLE 3

Percent CpG Methylation levels across LOCK domains detected in cell lines by WGBS. DNA methylation levels were highest for the peritoneal subclone A38Per across cell lines. Methylation was significantly reduced in distant metastases from the same patient (A38Lv, A38Lg) and in primary tumor precursors (A13Pr1/2) and the matched lung metastasis from patient A13. P-values were calculated with paired wilcox tests using a 3% threshold.

| Samples<br>Name<br>Source | Global LOCK<br>Methylation<br>% CpG Methylation in<br>LOCKs by WGBS | Significant Difference<br>p-value vs. A38Per |
| --- | --- | --- |
| A38Per<br>Peritoneal Met | 78.58% | N/A (Highest Methylation) |
| A38Lv<br>Liver Met | 67.39% | 2.20E−16 |
| A38Lg<br>Lung Met | 71.67% | 2.20E−16 |
| A13Pr1<br>Primary Tumor 1<br>Subclone | 72.46% | 2.18E−07 |
| A13Pr2<br>Primary Tumor 2<br>Subclone | 73.48% | 2.14E−06 |
| A13Lg<br>Lung Met | 71.30% | 2.20E−16 |

Figure 12:
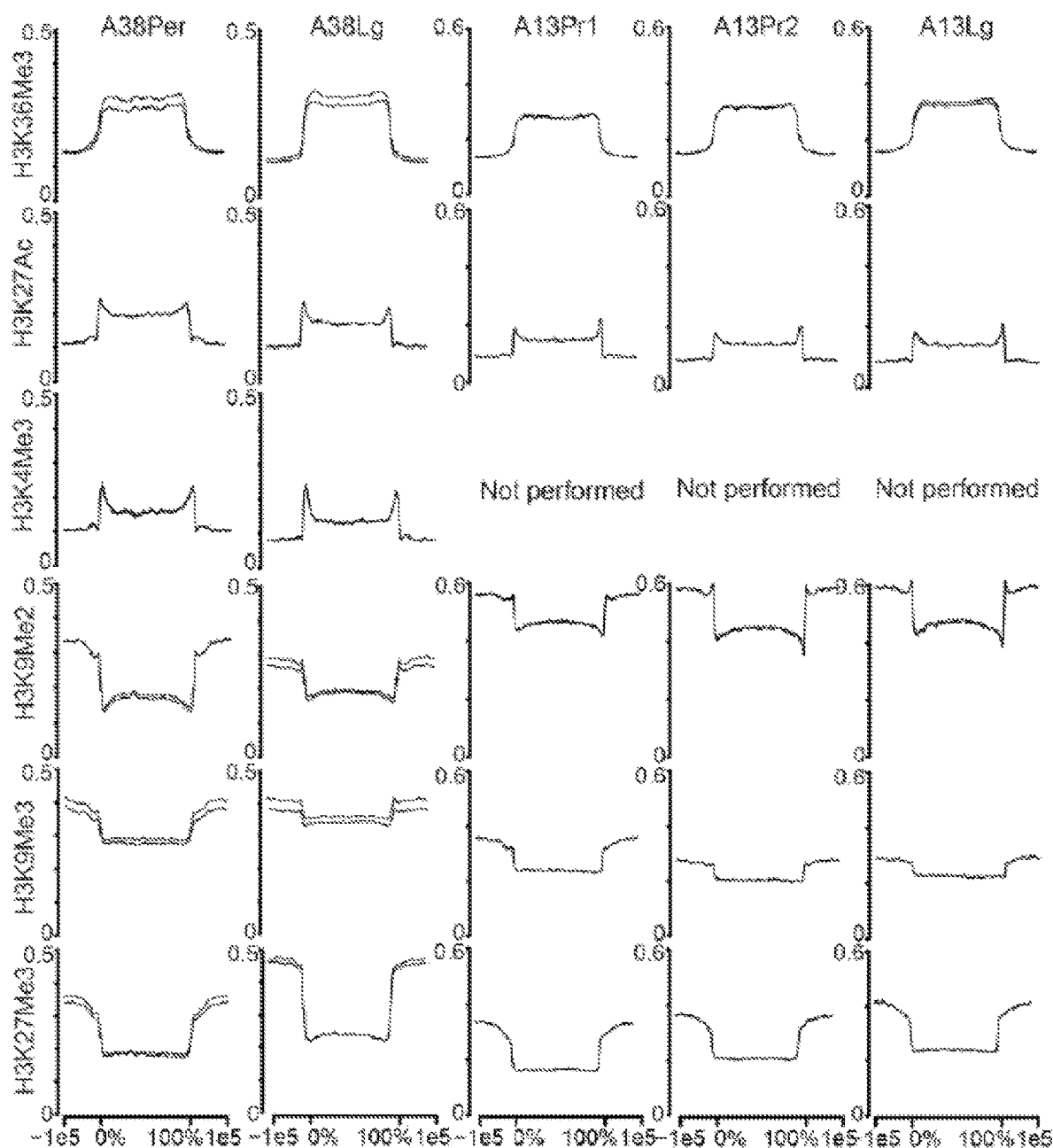
FIG. 12 is a series of graphical plots relating to enrichment of euchromatin modifications within ECDs.

We next analyzed reprogramming within ECDs, which were defined by enrichments for global euchromatin modifications H3K27Ac and H3K36Me3 with depletion of heterochromatin modifications (FIG. 12). Similar to heterochromatin, thousands of these domains (range: 1,935-2,318) were partitioned into large, block-like segments (median lengths: 207 Kb-277 Kb) that occupied similar lengths of the genome across subclones (average: 29% of the genome; range: 23.5%-32.0%, Supplementary Data 2). All subclones displayed similar global patterns of modifications within ECDs, including broad H3K36Me3 signals over gene bodies that were flanked by sharp peaks of H3K27Ac and dips in DNA methylation at gene regulatory elements, consistent with actively transcribed euchromatin (FIG. 2d). However, mapping DE genes from RNA-seq data to ECDs (Supplementary Data 3) identified clear patterns of local reprogramming events within chromatin encoding these genes (FIG. 2e, Supplementary Data 3). Genes up-regulated from ECDs acquired increased levels of both H3K36Me3 and H3K27Ac, which could reflect a permissive chromatin state or hyperactive transcription. In contrast, down-regulated genes displayed greatly reduced H3K36Me3 with relatively minor reductions of H3K27Ac, which could reflect an inactive yet poised chromatin state or direct transcriptional repression. Unlike LOCKs, DNA methylation remained stable around DE genes in ECDs (data not shown). Thus, reprogramming in ECDs was largely localized and targeted to H3K27Ac and H3K36Me3 in chromatin encoding DE genes.

Figures 13A, 13B, 13C, 13D, 13E:
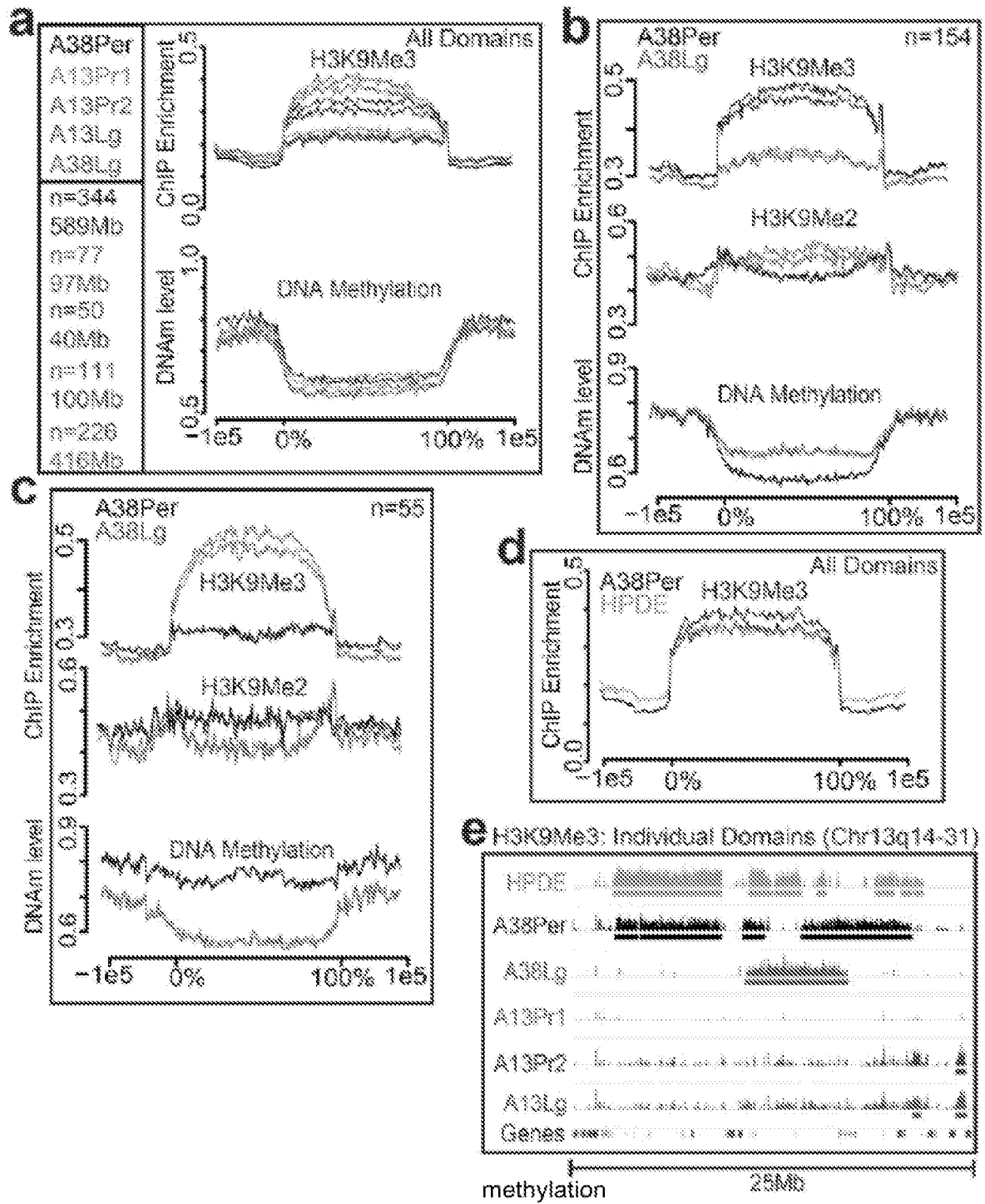
FIGS. 13A-13E relate to reprogramming of large LOCKs during PDAC evolution.

Finally, we also detected patient-specific reprogramming targeted to a unique subset of very large LOCK domains. Although these regions were situated within DNA hypomethylated blocks similar to other LOCKs, they differed in several other respects. First, these domains were substantially larger (median lengths: 730 Kb-1,340 Kb vs. 232-311 Kb for other LOCKs, Supplementary Data 2). Second, they were strongly enriched with H3K9Me3 yet depleted of H3K9Me2/H3K27Me3 (FIG. 13 and Supplementary Data 2). Third, their abundance was patient-specific: subclones from patient A13 possessed very few of these domains (range: 50-111 domains covering 1.4-3.5% of the genome) while they occupied a much higher fraction of the A38 genome (range: 226-344 domains covering 14.5-20.6% of the genome, FIG. 13a and Supplementary Data 2). Finally, unlike reprogramming changes detected in other LOCKs (loss of H3K9Me2/3 and DNA methylation), reprogramming in these LOCKs was characterized by loss of H3K9Me3 coupled to increased H3K9Me2 and DNA methylation (FIG. 13b-e). Although the functional significance of these findings is uncertain, they could hold implications for patterns of genome instability that emerged during subclonal evolution, as outlined below.

Reprogrammed Chromatin Domains Specify Malignant Heterogeneity

Subclonal evolution may generate significant phenotypic heterogeneity within an individual patient, and we have hypothesized that such diversity could be encoded by large-scale epigenetic changes similar to those detected above. We therefore wished to investigate in-depth whether reprogrammed chromatin domains might encode heterogeneous malignant properties between PDAC subclones from the same patient. To this end, we selected matched peritoneal and lung metastasis subclones from the same patient (A38Per and A38Lg), performed gene ontology (GO) analyses on reprogrammed LOCK and ECD genes that were differentially expressed between the subclones (Tables 4-7, derived from reprogrammed genes as shown in FIG. 2e and FIG. 11), and then tested whether GO results matched actual phenotypic differences measured by experimental assays. This analysis revealed that reprogrammed LOCKs and ECDs encoded substantial phenotypic differences that emerged during subclonal evolution, as described below.

TABLE 4

GO analysis of DE genes that were up-regulated from reprogrammed LOCKs in A38Lg, relative to A38Per. Genes involved in redox balance (oxidation-reduction, NADP) and EMT (cell adhesion, migration) were up-regulated from reprogrammed DE genes in LOCKs (Detailed in Supplementary Data 3).

| GO Terms | # of Genes | % of Genes | P-value |
|---|---|---|---|
| Oxidation-reduction | 64 | 6.0 | 3.9e−6 |
| Oxidoreductase | 56 | 5.2 | 4.7e−6 |
| EGF-like domain | 28 | 2.6 | 6.4e−5 |
| Transferase | 105 | 9.8 | 1.0e−4 |
| NADP | 21 | 2.0 | 1.7e−4 |
| Cell Adhesion | 41 | 3.8 | 1.8e−4 |
| Cell Migration | 31 | 2.9 | 2.7e−4 |
| Cell Morphogenesis | 29 | 2.7 | 3.8e−4 |
| Mitochondrion | 67 | 6.3 | 4.0e−4 |
| Acetylation | 174 | 16.3 | 5.0e−4 |

TABLE 5

GO analysis of DE genes that were down-regulated from reprogrammed LOCKs in A38Lg, relative to A38Per. Genes involved in differentiation state (cell adhesion, development, epithelial genes), immune regulation (immune response, cytokines, inflammation), and response to environmental cues (transmembrane signaling, extracellular matrix, secretion, locomotion) were down-regulated from reprogrammed LOCKs (Detailed in Supplementary Data 3).

| GO Terms | # of Genes | % of Genes | P-value |
|---|---|---|---|
| Signal | 399 | 32.4 | 1.5e−31 |
| Glycoprotein | 488 | 40.0 | 1.0e−30 |
| Disulfide Bond | 352 | 28.5 | 1.0e−25 |
| Secreted | 217 | 17.6 | 1.5e−18 |
| Membrane | 582 | 47.2 | 1.7e−15 |
| Polymorphism | 951 | 77.1 | 1.5e−13 |
| Immune Response | 106 | 8.6 | 1.6e−13 |

TABLE 5-continued

GO analysis of DE genes that were down-regulated from reprogrammed LOCKs in A38Lg, relative to A38Per. Genes involved in differentiation state (cell adhesion, development, epithelial genes), immune regulation (immune response, cytokines, inflammation), and response to environmental cues (transmembrane signaling, extracellular matrix, secretion, locomotion) were down-regulated from reprogrammed LOCKs (Detailed in Supplementary Data 3).

| GO Terms | # of Genes | % of Genes | P-value |
|---|---|---|---|
| Immunoglobin Domain | 75 | 6.1 | 8.5e−11 |
| Cytokine-Cytokine Receptor Interaction | 54 | 4.4 | 2.3e−10 |
| Ion Channel | 55 | 4.5 | 2.1e−9 |
| Inflammatory Response | 55 | 4.5 | 7.6e−9 |
| Cell Adhesion | 93 | 7.5 | 1.4e−8 |
| Developmental Protein | 98 | 7.9 | 4.4e−8 |
| Cell Motion | 69 | 5.6 | 4.7e−8 |
| Transmembrane Protein | 82 | 6.7 | 3.4e−7 |
| Protease Inhibitor | 25 | 2.0 | 3.9e−7 |
| Response to Wounding | 71 | 5.8 | 7.0e−7 |
| Extracellular Matrix | 40 | 3.2 | 1.2e−6 |
| Epithelial Cell Differentiation | 28 | 2.3 | 1.6e−6 |

TABLE 6

GO analysis of DE genes that were up-regulated from reprogrammed ECDs in A38Lg, relative to A38Per. Genes involved in post-translational modifications, cell cycle control, DNA repair, response to stress, and DNA/RNA/protein biosynthesis were up-regulated from reprogrammed ECDs (Detailed in Supplementary Data 3).

| GO Terms | # of Genes | % of Genes | P-value |
|---|---|---|---|
| Acetylation | 622 | 21.7 | 1.1e−59 |
| Phosphoprotein | 1290 | 45.0 | 5.1e−53 |
| Cell Cycle | 154 | 5.4 | 3.4e−30 |
| Mitotic Cell Cycle | 137 | 4.8 | 4.9e−30 |
| Organelle Fission | 95 | 3.3 | 3.7e−25 |
| DNA Metabolic Process | 157 | 5.5 | 9.4e−25 |
| DNA Repair | 95 | 3.3 | 1.4e−17 |
| Response to DNA Damage Stimulus | 113 | 3.9 | 3.8e−17 |
| DNA Replication | 68 | 2.4 | 2.7e−14 |
| Cellular Response to Stress | 144 | 5.0 | 3.1e−14 |
| Protein Biosynthesis | 62 | 2.1 | 2.8e−12 |
| ATP Binding | 256 | 8.9 | 1.3e−11 |
| Ribonucleoprotein | 78 | 2.7 | 4.1e−11 |
| Nucleotide Binding | 309 | 10.7 | 4.3e−11 |
| Translation | 86 | 3.0 | 2.5e−9 |
| ncRNA Metabolic Process | 66 | 2.3 | 3.5e−9 |
| Mitochondrion | 167 | 5.8 | 4.3e−9 |
| DNA Recombination | 39 | 1.4 | 4.6e−9 |
| Microtubule-based Process | 70 | 2.4 | 5.9e−9 |

TABLE 7

GO analysis of DE genes that were down-regulated from reprogrammed ECDs in A38Lg, relative to A38Per. Genes involved in oncogenic signal transduction cascades (Sh3 domains, transmembrane proteins, kinases, Ras signaling), cell motion (wounding, migration, locomotion), and cell death control (apoptosis) were down-regulated from reprogrammed ECDs (Detailed in Supplementary Data 3).

| GO Terms | # of Genes | % of Genes | P-value |
|---|---|---|---|
| Alternative Splicing | 1195 | 49.0 | 1.5e−16 |
| Sh3 Domain | 65 | 2.7 | 6.8e−10 |
| Phosphoprotein | 1112 | 45.0 | 1.3e−9 |
| Membrane | 964 | 39.4 | 1.4e−9 |
| Response to Wounding | 117 | 4.8 | 9.0e−8 |
| Pleckstrin Homology | 71 | 2.9 | 2.8e−7 |
| Cell Migration | 49 | 2.0 | 3.4e−7 |
| Small GTPase Signal Transduction | 65 | 2.7 | 3.9e−7 |

TABLE 7-continued

GO analysis of DE genes that were down-regulated from reprogrammed ECDs in A38Lg, relative to A38Per. Genes involved in oncogenic signal transduction cascades (Sh3 domains, transmembrane proteins, kinases, Ras signaling), cell motion (wounding, migration, locomotion), and cell death control (apoptosis) were down-regulated from reprogrammed ECDs (Detailed in Supplementary Data 3).

| GO Terms | # of Genes | % of Genes | P-value |
|---|---|---|---|
| Locomotion | 52 | 2.1 | 1.4e−6 |
| Intracellular Signaling Cascade | 227 | 9.3 | 3.5e−6 |
| Tyrosine Protein Kinase | 34 | 1.4 | 5.4e−6 |
| Regulation of Apoptosis | 153 | 6.2 | 1.1e−5 |
| Protein Kinase Cascade | 81 | 3.3 | 1.4e−5 |
| Protein Amino Acid Phosphorylation | 130 | 5.3 | 1.8e−5 |
| Ankyrin Repeat | 56 | 2.3 | 3.7e−5 |
| Ras Protein Signal Transduction | 51 | 2.1 | 4.6e−5 |

Figure 3A:
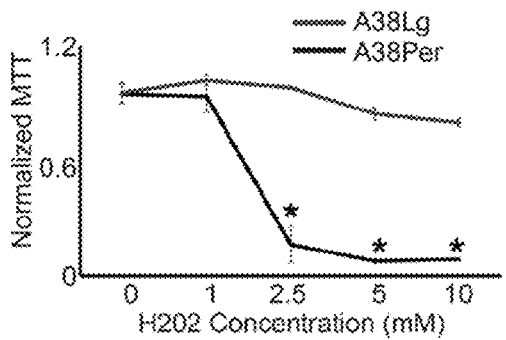
FIGS. 3A-3G relate to reprogrammed chromatin domains encoding divergent malignant properties.
Figure 3B:
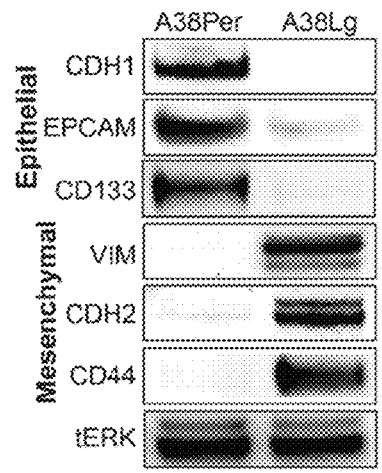
Figure 3C:
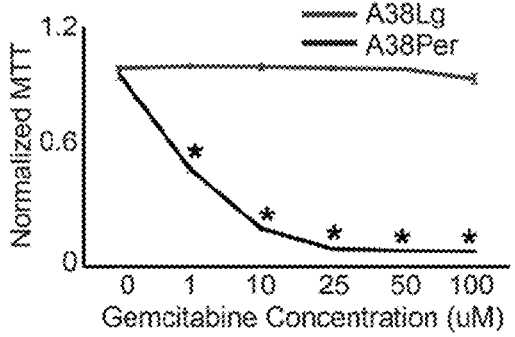
Figure 3D:
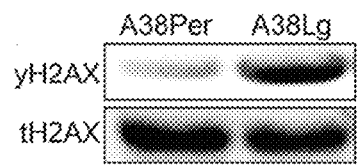
Figure 3E:
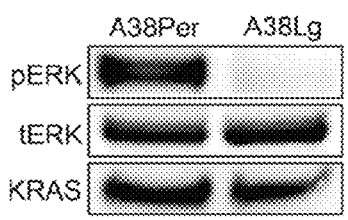
Figure 3F:
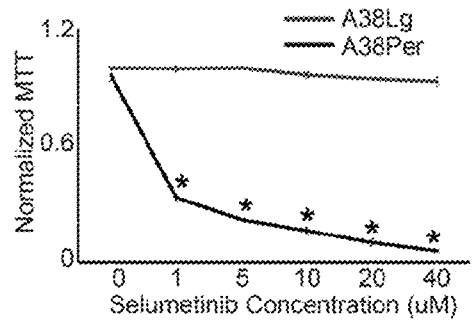
Figure 3G:
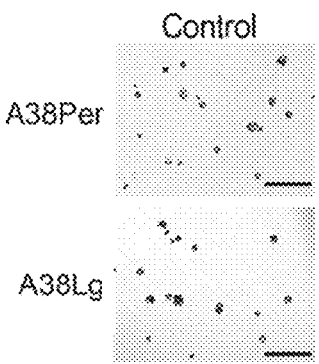
Figures 15A, 15B, 15C:
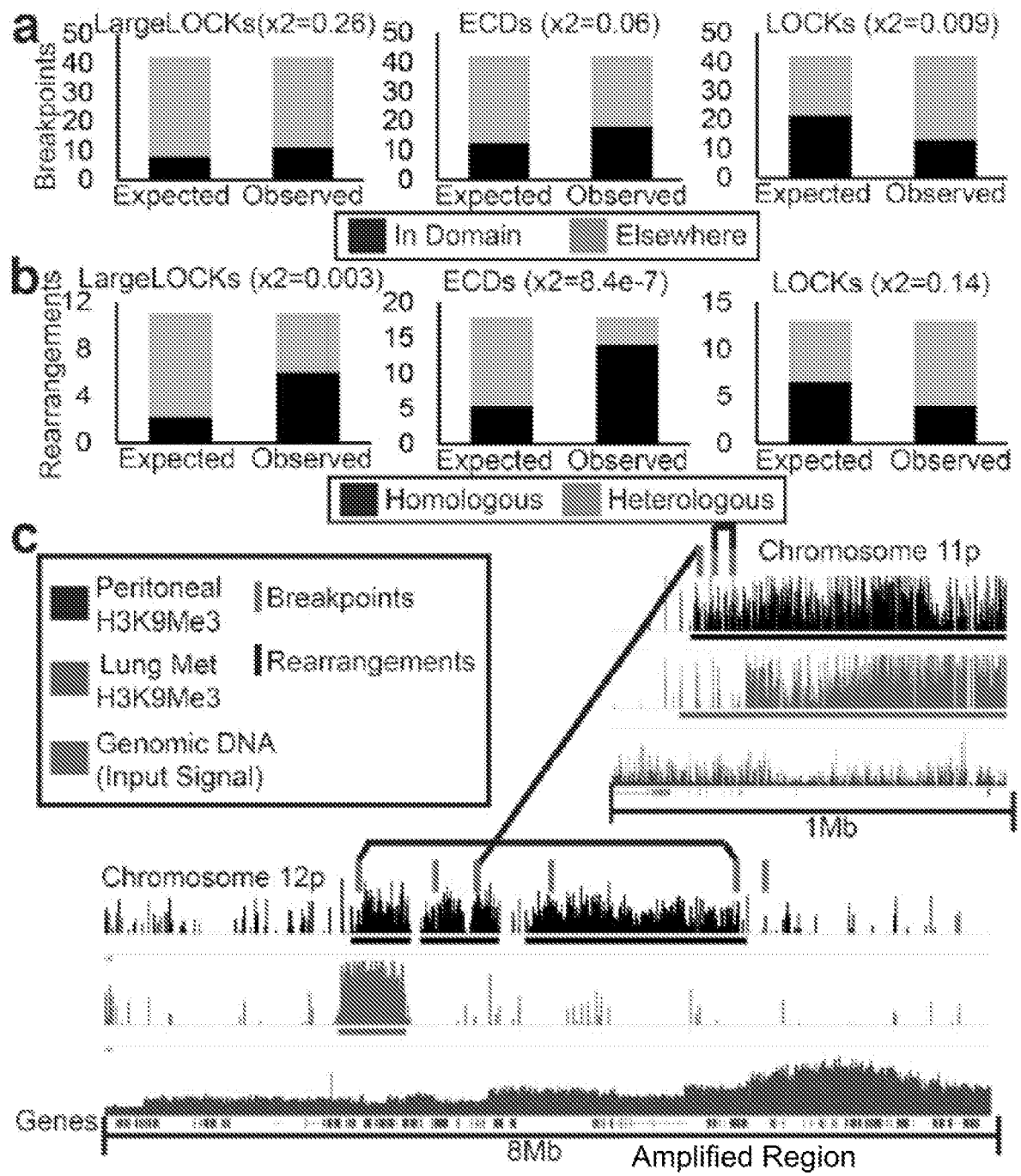
FIGS. 15A-15C relate to rearrangements targeted to Large LOCKs and ECDs.

First, a large number of DE genes involved in redox (oxidation-reduction) balance were up-regulated from reprogrammed LOCKs in A38Lg (Table 4, Supplementary Data 3). This subclone was accordingly highly resistant to $H_2O_2$-mediated oxidative stress (FIG. 3a), and possessed higher oxidoreductase activity and NADPH levels than A38Per (FIG. 14a, b). Second, genes encoding differentiation state (epithelial vs. EMT) were reciprocally expressed from A38Per and A38Lg LOCKs (Table 5, Supplementary Data 3), and we confirmed several well-known epithelial and EMT expression changes (e.g. CDH1/E-cadherin, CDH2/N-cadherin) at the protein level by western blots (FIG. 3b). Further consistent with GO results, A38Per maintained well-differentiated (epithelial) morphology while A38Lg was poorly differentiated (EMT-like) across multiple in vitro culture conditions (FIG. 14c), and immunofluorescence experiments showed that EMT emerged in the primary tumor subclone that seeded the A38Lg metastasis in vivo (FIG. 14d). We also note that immune-related genes were differentially expressed from reprogrammed LOCKs (Table 5), which could hold implications for PDAC immunotherapy. Third, genes involved in DNA repair and cell stress responses were significantly up-regulated in ECDs from A38Lg, including genes crucial for maintenance of genome integrity (Fanconi anemia complex, non-homologous end joining, and the TOP2B/OGG1/KDM1A complex, among others, Table 6, Supplementary Data 3). This subclone was accordingly highly resistant to PDAC chemotherapy (gemcitabine) compared to A38Per (FIG. 3c), and western blots showed hyper-phosphorylation of histone H2AX S139 (γH2AX, a signature of activated DNA repair pathways, FIG. 3d). Fourth, genes involved in oncogenic signal transduction cascades were down-regulated in ECDs from A38Lg, especially KRAS/ERK-related genes (Table 7, Supplementary Data 3). Indeed, A38Lg showed loss of phosphorylated ERK (FIG. 3e), resistance to ERK inhibition (FIG. 3f), and minimal response to knockdown of oncogenic KRAS in 3D tumor forming assays (FIG. 3g, FIG. 14e, f), despite possessing identical $KRAS^{G12V}$ mutations as A38Per. Finally, mapping previously reported rearrangements from this patient to chromatin domains revealed that rearrangements were preferentially targeted to ECDs and the small subset of uniquely reprogrammed large LOCK domains, whereas other LOCKs were strongly depleted (FIG. 15).

Thus, reprogrammed chromatin domains collectively specified malignant gene expression programs, divergent phenotypic properties, and patterns of genome instability that emerged during subclonal evolution in patient A38. This patient was unusual in having received chemotherapy prior to tissue harvesting and had a missense mutation in SMARCA2 of unclear significance (CID, unpublished observations), and thus in this case epigenetic selection may have occurred downstream of a genetic driver. Although the nature and extent of such findings will certainly vary among patients, they imply that PDAC is capable of acquiring substantial epigenetic and malignant diversity during subclonal evolution, even in the same cancer from the same patient.

Anabolic Glucose Metabolism Controls Epigenetic State and Tumorigenicity

We next asked whether a recurrent, metastasis-intrinsic pathway might have been selected for during subclonal evolution to exert upstream control over global epigenetic state and tumorigenic potential. Several recent studies have linked nutrient status and metabolic activity to global levels of histone modifications. Because distant metastases in the rapid autopsy cohort were largely isolated from organs (liver, lung) that provide a rich supply of glucose, we asked whether reprogrammed chromatin and tumorigenicity in these subclones might have evolved a dependence on specific aspects of glucose metabolism.

Figures 4A, 4B, 4C, 4D, 4E, 4F:
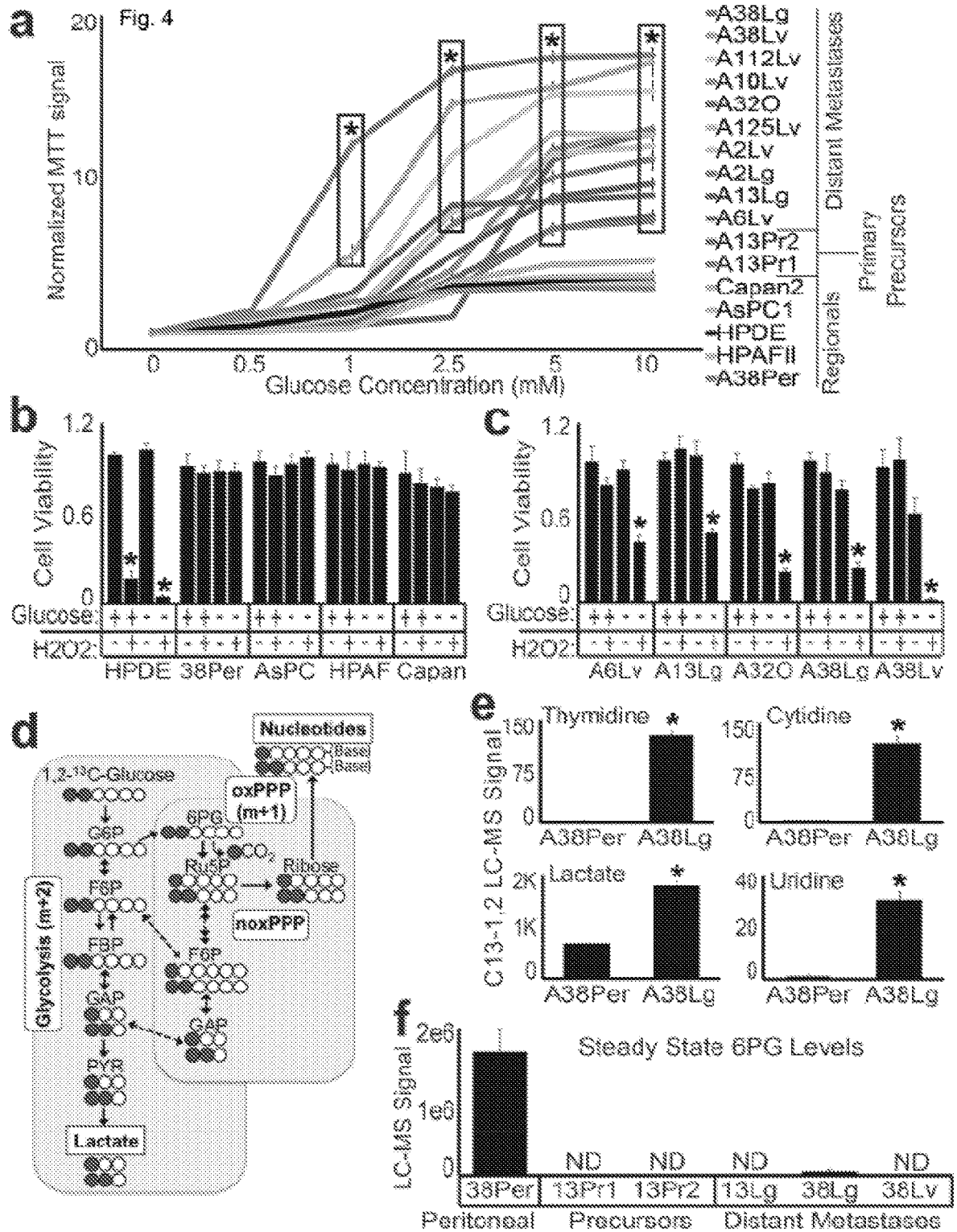
FIGS. 4A-4F relate to hyperactive glucose metabolism and 6PG depletion in distant metastatic subclones.
Figures 16A, 16B:
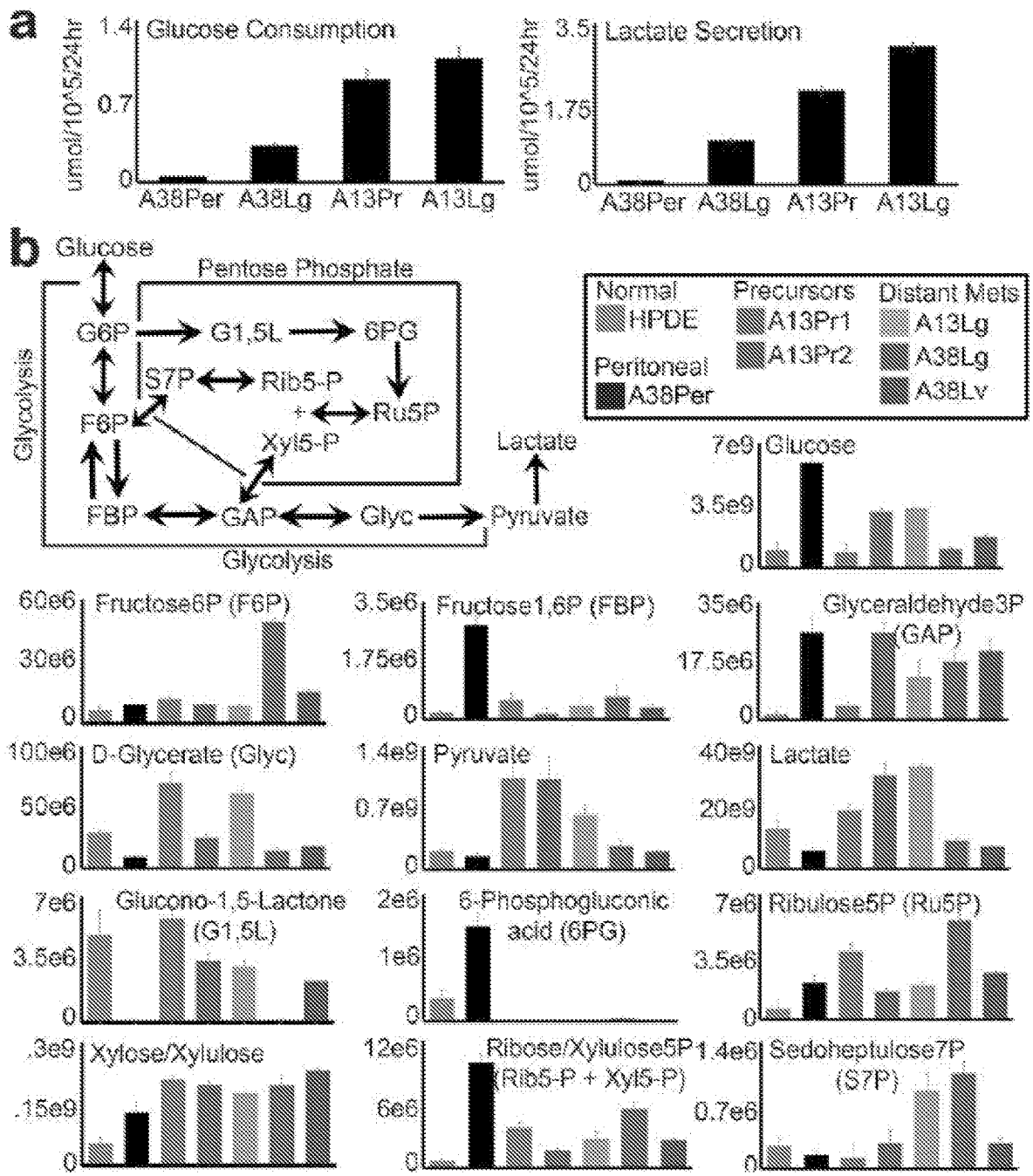
FIGS. 16A-16B relate to enhanced glucose metabolism with depleted 6PG levels across distant metastases.

Altered glucose metabolism (i.e. Warburg effect) is a well-known property of neoplastic and highly proliferative cells. Although most of our metastatic subclones actually displayed modest proliferative rates in culture (e.g. FIG. 8) and in vivo, we nonetheless asked whether distant metastases might have acquired further adaptations in glucose metabolism. Surprisingly, relative to proliferative (immortalized) normal HPDE cells and local-regional PDAC samples, glucose strongly stimulated metabolic (oxidoreductase) activity across distant metastatic subclones (FIG. 4a), and glucose was accordingly required for these subclones to withstand oxidative stress (FIG. 4b, c). Distant metastases also hyper-consumed glucose, as we detected elevated glucose uptake and lactate secretion in distant metastases and their precursors relative to peritoneal carcinomatosis (FIG. 16a). To determine if excess glucose uptake was specifically incorporated into downstream metabolic pathways, we selected paired peritoneal and distant metastatic subclones from the same patient, incubated them with $^{13}C[1-2]$-labeled glucose, and measured glucose incorporation into metabolic products with liquid chromatography followed by high resolution mass spectrometry (LC-HRMS). These experiments revealed elevated incorporation of both C1- and C1,2-labeled glucose into lactate and nucleotides in the distant metastasis (FIG. 4d,e), consistent with enhanced glucose entry into both glycolysis and the pentose phosphate pathway (PPP).

We next asked whether distant metastases might have evolved a dependence on specific enzymatic steps in either of these glucose-driven pathways, which we hypothesized would manifest as severe depletion of metabolite substrate secondary to hyper-consumption. To test this, we surveyed glycolytic and PPP metabolite profiles across a diverse panel of samples including HPDE cells, peritoneal carcinomatosis, distant metastases, and primary tumor precursor subclones. Analysis of all detected glycolytic and pentose phosphate metabolites (FIG. 16b) revealed a striking, recurrent depletion of 6-phosphogluconic acid (6PG) across distant metastases and their precursors (FIG. 4f). 6PG is the substrate for 6-phosphogluconate dehydrogenase (PGD), an enzyme involved in anabolic glucose metabolism that operates within the oxidative branch of the PPP.

Figures 5A, 5B, 5C, 5D:
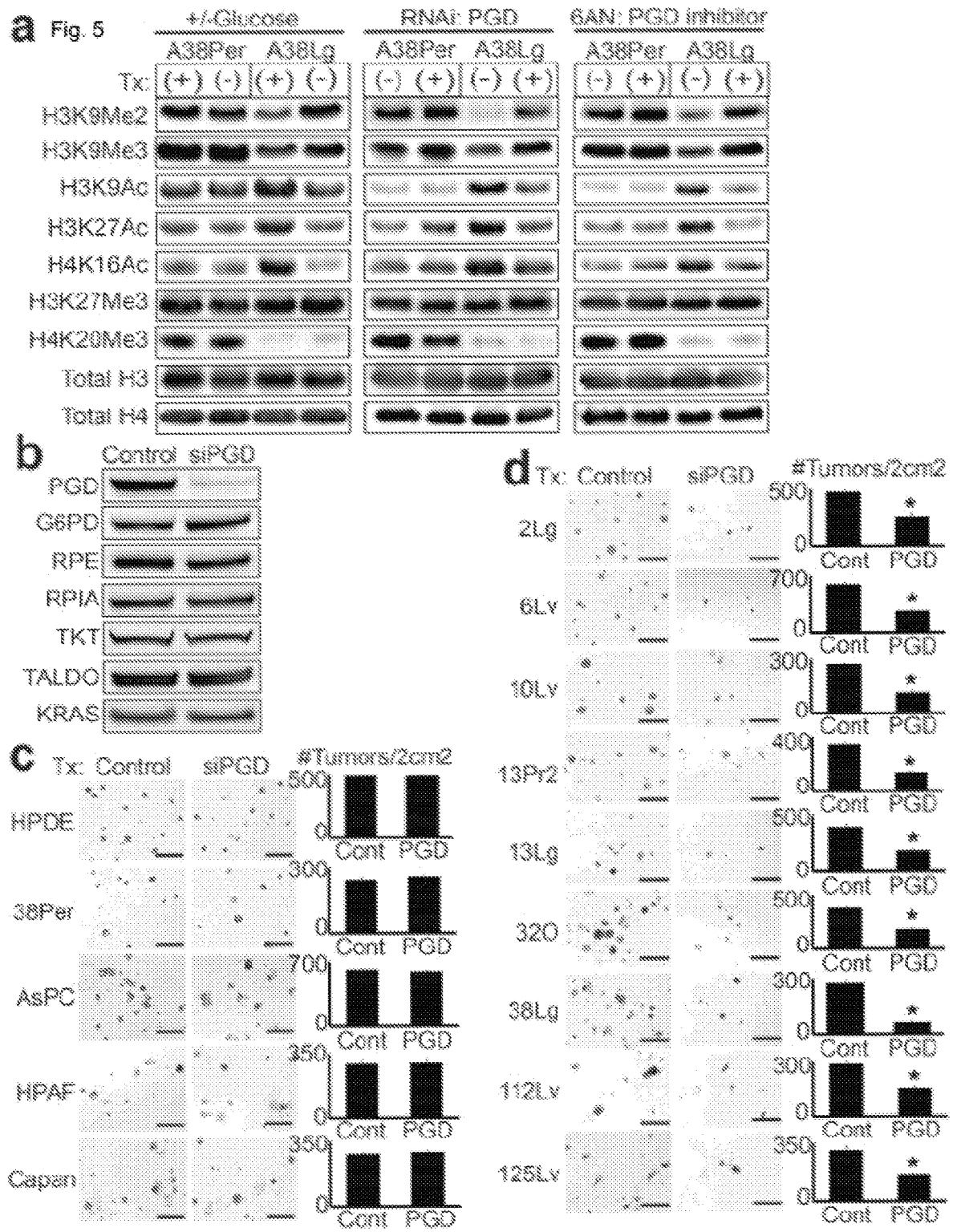
FIGS. 5A-5D relate to PGD-dependence in distant metastatic subclones.

Glucose may enter the PPP via the oxidative (oxPPP) or the non-oxidative (noxPPP) branch of the pathway, which are thought to be uncoupled. Although some studies in other cancers have suggested that PGD is an important oncogene, it is KRAS-mediated noxPPP activation that drives primary tumor growth in mouse models of PDAC. Because KRAS and other driver mutations are acquired early in PDAC progression and shared by all subclones that evolve thereafter, we hypothesized that PGD dependence might have been selected for specifically during the evolution of distant metastasis to maintain reprogrammed chromatin and tumorigenicity. Glucose deprivation, RNAi against PGD, and 6-aminonicotinamide (6AN, a nicotinamide antimetabolite prodrug reported to preferentially inhibit PGD) had no effect on global chromatin modifications in the peritoneal subclone, while all treatments reversed the reprogrammed chromatin state of the paired lung metastasis from the same patient (FIG. 5a). PGD loss-of-function appeared specific, as PGD knockdown did not alter expression of KRAS or other PPP components (FIG. 5b).

We next asked whether PGD knockdown might affect intrinsic tumor forming capacity across a larger panel of subclones. Despite their aggressive behavior in patients, distant metastatic subclones were unable to effectively form metastatic tumors in immunodeficient mice, and PGD RNAi was not toxic to any subclones grown in routine 2-D cultures (data not shown). To bypass these limitations, we treated cells with RNAi and used 3-D matrigel tumor-forming assays to measure the effects of PGD knockdown on intrinsic tumor-forming capacity. PGD RNAi had minimal effect on the ability of HPDE cells to form spheres or local-regional PDACs to form tumors by these assays (FIG. 5c). Remarkably, PGD RNAi universally interfered with the ability of distant metastatic subclones to form tumors (FIG. 5d). These findings suggested that PGD might represent a therapeutic target with selectivity for PDAC distant metastasis. Because 6AN could represent a lead compound for future design of PGD targeted therapies, we stringently tested it for activity against distant metastases with metabolomics, western blots, multiple 3D tumorigenic assays, RNA-seq, and ChIP experiments.

Figures 17A, 17B, 17C:
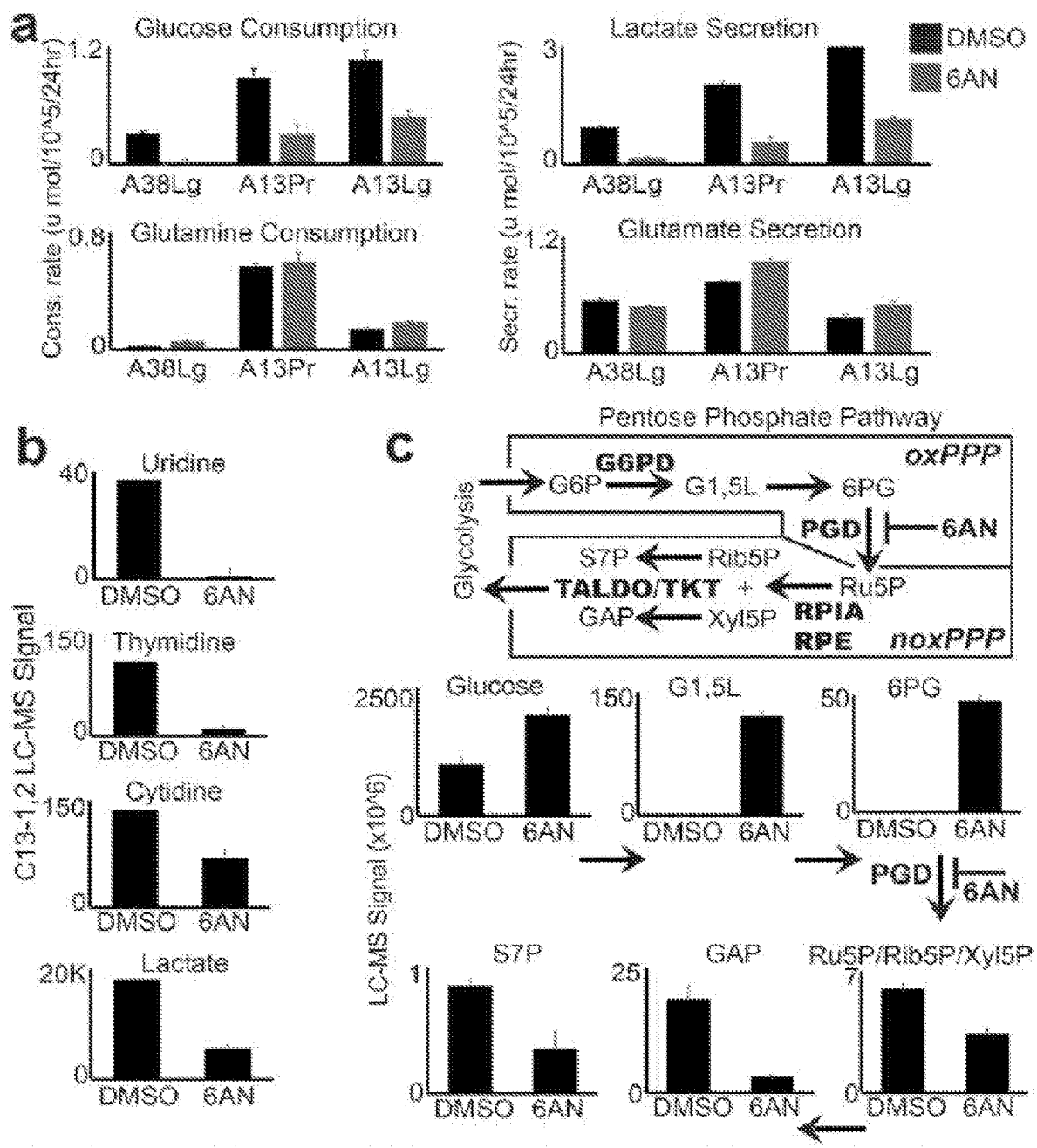
FIGS. 17A-17C relate to 6AN targeting of glucose metabolism and the PGD step of the PPP.

6AN treatments slowed rates of glucose consumption and lactate secretion with no effect on glutamine consumption or glutamate secretion in distant metastatic and precursor subclones (FIG. 17a), and 6AN reversed the previously detected high incorporation of glucose into lactate and nucleotides (FIG. 117). Furthermore, steady state levels of glucose and metabolites directly upstream of the PGD reaction were dramatically elevated in response to 6AN with corresponding reductions in downstream metabolites (FIG. 17c), which is consistent with strong PGD inhibition as previously reported by others.

Figures 18A, 18B, 18C:
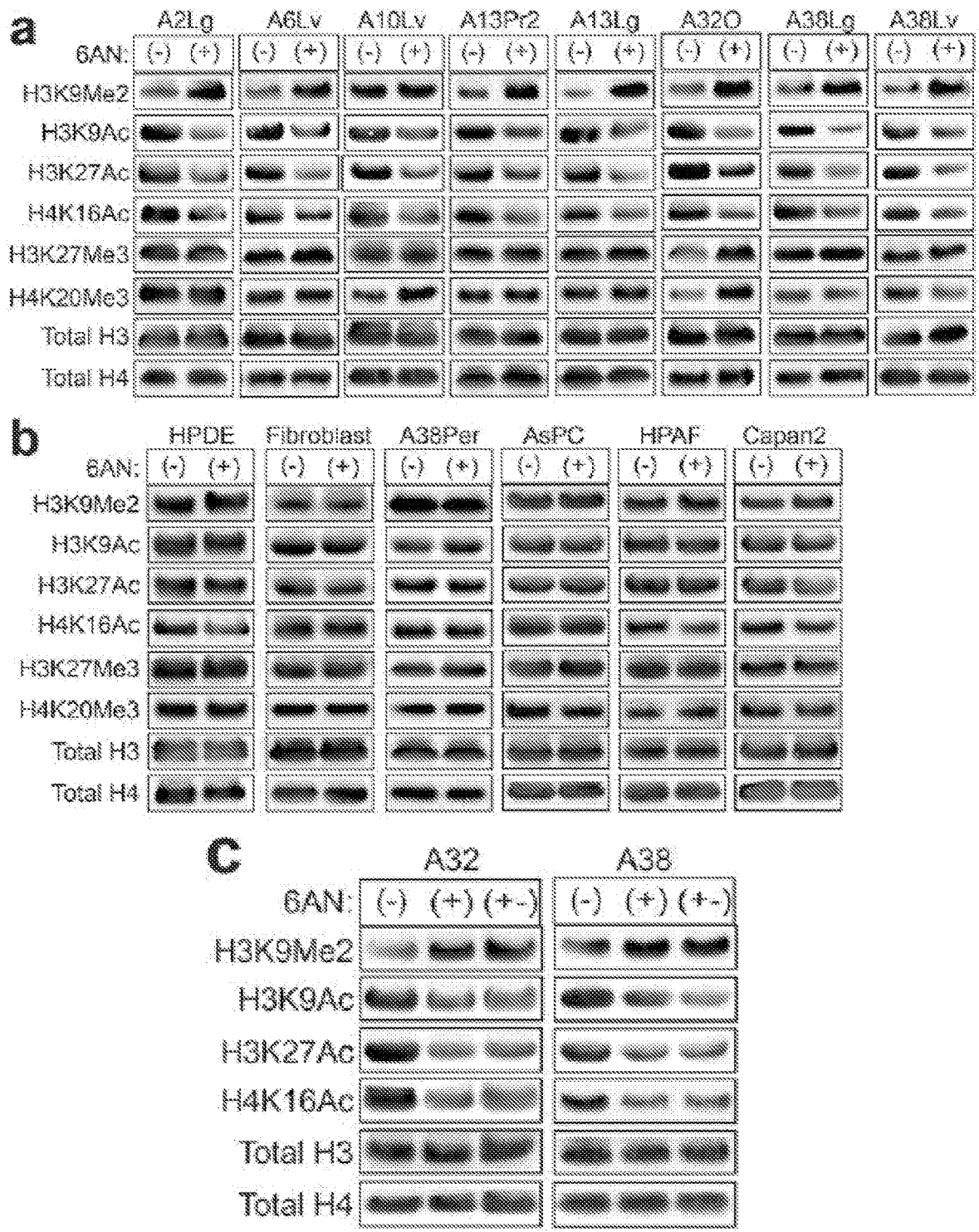
FIGS. 18A-18C relate to 6AN selectively modulation of the reprogrammed chromatin state of distant metastatic subclones.
Figures 19A, 19B, 19C, 19D:
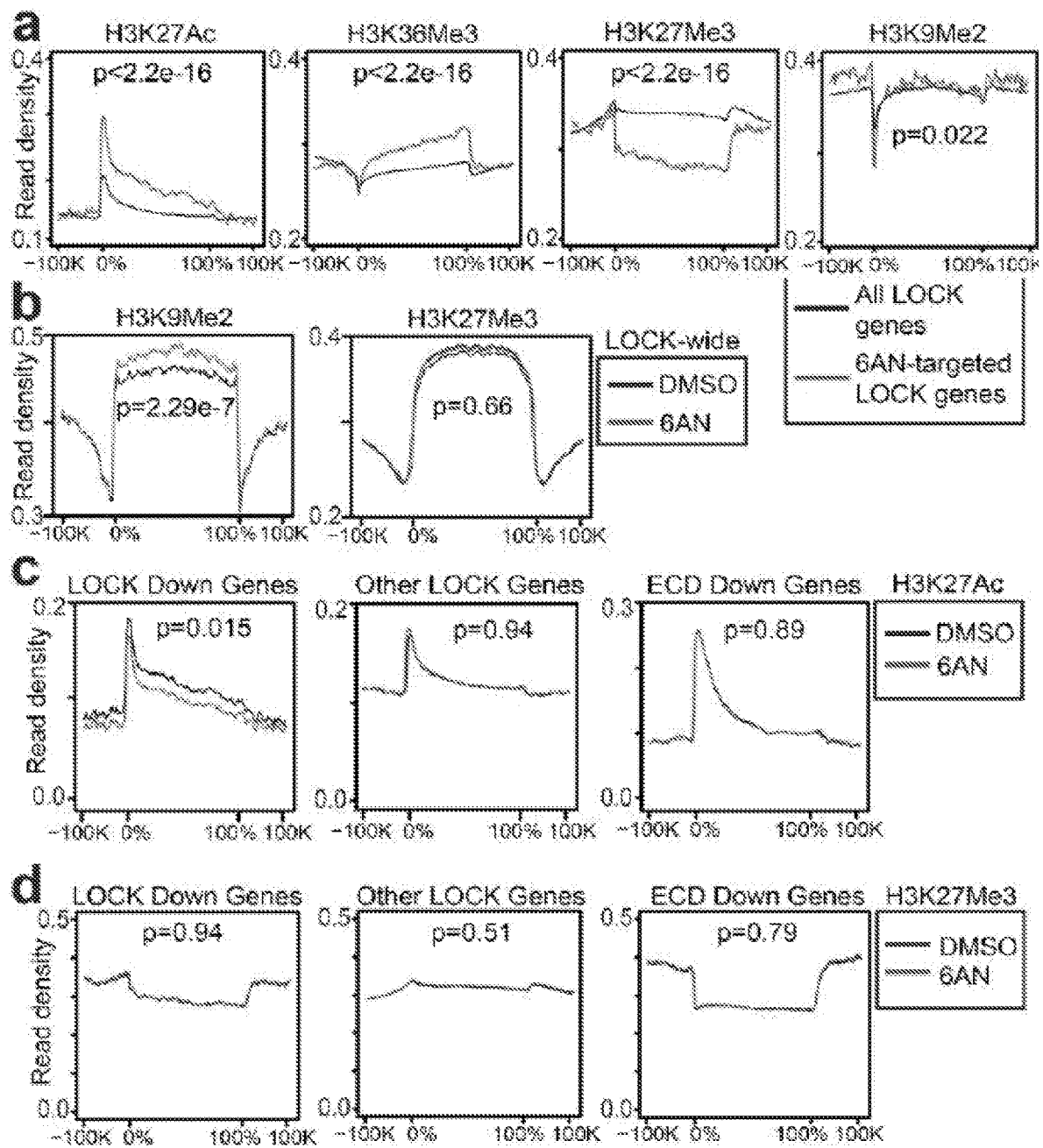
FIGS. 19A-19D relate to 6AN regulated gene expression in LOCK-EI regions.

We next tested the effects of 6AN on epigenetic state. Strikingly, 6AN treatments quantitatively reversed several reprogrammed chromatin modifications across distant metastatic subclones with minimal effect on normal cells or local-regional PDACs (FIG. 18a, b; summarized in FIG. 6a, b), and this effect persisted upon removal of 6AN from the media (FIG. 18c). Because these changes mirrored aspects of LOCK reprogramming, we examined the chromatin state of LOCK DE genes regulated by 6AN, as identified by RNA-seq (Supplementary Data 3, 4). This revealed that DE genes were located within the reprogrammed hybrid LOCK-EI regions that possessed strong H3K27Ac and H3K36Me3, low H3K27Me3, and sharp 5'-depletion (dips) of H3K9Me2 (FIG. 19a, Supplementary Data 3). ChIP-seq experiments on control and 6AN-treated A38Lg cells further showed that the quantitative increase of global H3K9Me2 was targeted to LOCK regions that were reprogrammed in A38Lg vs. A38Per (FIG. 19b), while the reduced H3K27Ac was specifically targeted to genes repressed from LOCKs with no effect on other LOCK genes or ECD-regulated genes (FIG. 19c). Levels of H3K27Me3 remained stable across all regions in response to 6AN (FIG. 19b, d), similar to western blot findings. Collectively, these experiments demonstrated that 6AN selectively and quantitatively targeted several chromatin changes within LOCKs that emerged during the evolution of distant metastasis.

Figures 6A, 6B, 6C, 6D:
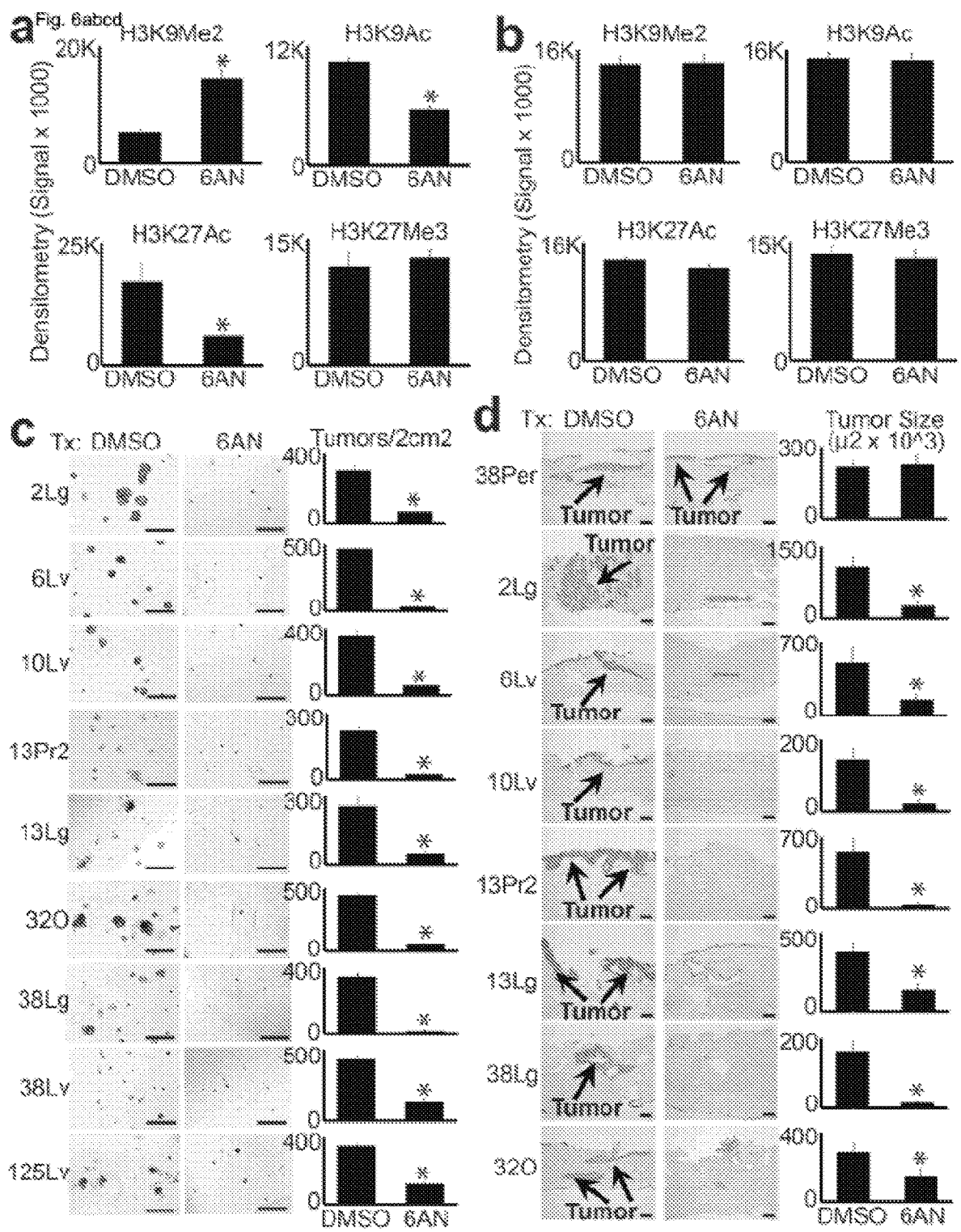
FIGS. 6A-6F relate to reversal of reprogrammed chromatin, tumorigenicity, and malignant gene expression programs by 6AN.

Because 6AN modulated the global epigenetic state, we hypothesized that it might also selectively block tumorigenic potential in distant metastatic subclones, similar to PGD knockdown experiments. Strikingly, 6AN selectively and strongly blocked tumor formation in distant metastatic and primary tumor precursor subclones but not local-regional PDACs across multiple 3D tumorigenic experimental platforms, including suspension tumorsphere assays (Supplementary FIG. 20), matrigel tumor forming assays (FIG. 6b), and injection of PDAC cells into organotypic stroma that recapitulates aspects of in vivo patient tumors (FIG. 6c). Thus, like PGD knockdown, chemical inhibition of PGD by 6AN selectively blocked the tumorigenic potential of distant metastatic subclones.

We next examined our RNA-seq datasets to explore whether the above findings might be linked to regulation of malignant gene expression programs. Remarkably, over half (952/1832, 52%, Supplementary Data 4) of 6AN down-regulated genes from A38Lg corresponded to genes that were over-expressed in this subclone (compared to the peritoneal subclone from the same patient). In addition, a large fraction of 6AN up-regulated genes also matched DE genes that were repressed (914/2122, 42%, Supplementary Data 4). Even more striking, nearly one-third (255/891, 29%, Supplementary Data 4) of recurrently over-expressed genes across distant metastatic subclones were down-regulated by 6AN. Comparative GO analyses on these gene subsets produced overlapping results that were strongly enriched for cancer-related functions, including mitotic cell cycle control, acetylation, chromosome stability, DNA repair, cell stress responses, and anabolic/biosynthetic activities (Tables 8-10).

TABLE 8

GO analysis of genes that were both recurrently over-expressed in distant metastases and down-regulated by 6AN, detected by RNA-seq (detailed in Supplementary Data 3).

| Go Terms | # of Genes | % of Genes | P-value |
| --- | --- | --- | --- |
| Nucleus | 112 | 40.0 | 1.4e−19 |
| Phosphoprotein | 150 | 53.6 | 1.3e−18 |
| Acetylation | 80 | 28.6 | 2.7e−16 |
| DNA Metabolic Process | 36 | 12.9 | 1.2e−15 |
| Cell Cycle | 39 | 13.9 | 3.4e−12 |
| M-phase | 29 | 8.9 | 1.8e−11 |
| DNA Repair | 22 | 7.9 | 2.8e−10 |
| DNA Replication | 18 | 6.4 | 8.5e−10 |
| Cellular Response to Stress | 27 | 9.6 | 5.0e−8 |
| Ribonucleotide Biogenesis | 13 | 4.6 | 6.3e−6 |

TABLE 9

GO analysis of recurrently over-expressed genes detected by RNA-seq in distant metastatic subclones and primary tumor precursors, relative to peritoneal carcinomatosis (detailed in Supplementary Data 3).

| GO Terms | # of Genes | % of Genes | P-value |
| --- | --- | --- | --- |
| Acetylation | 217 | 20.7 | 8.0e−28 |
| Phosphoprotein | 428 | 40.0 | 5.3e−24 |

TABLE 9-continued

GO analysis of recurrently over-expressed genes detected by RNA-seq in distant metastatic subclones and primary tumor precursors, relative to peritoneal carcinomatosis (detailed in Supplementary Data 3).

| GO Terms | # of Genes | % of Genes | P-value |
| --- | --- | --- | --- |
| Protein Biosynthesis | 36 | 3.4 | 1.4e−14 |
| Nucleus | 256 | 24.4 | 1.8e−13 |
| Ribonucleoprotein | 41 | 3.9 | 1.4e−12 |
| Translation | 47 | 4.5 | 1.5e−12 |
| DNA Metabolic Process | 53 | 5.1 | 4.5e−9 |
| Cell Cycle | 65 | 6.2 | 3.4e−7 |
| Mitochondria | 64 | 6.1 | 5.4e−7 |
| DNA Repair | 31 | 3.0 | 5.2e−6 |
| Nitrogen Compound Biosynthesis | 33 | 3.1 | 1.1e−5 |
| Nucleotide Binding | 102 | 9.7 | 1.4e−6 |
| M-phase | 33 | 3.1 | 1.4e−5 |
| Cellular Response to Stress | 47 | 4.5 | 2.5e−5 |
| Transit Peptide | 39 | 3.7 | 3.3e−5 |
| Nucleotide Biosynthetic Process | 22 | 2.1 | 5.1e−5 |
| ATP Binding | 82 | 7.8 | 5.3e−5 |
| DNA Replication | 22 | 2.1 | 7.0e−5 |
| WD40 Repeat | 24 | 2.3 | 1.4e−4 |

TABLE 10

GO analysis of DE genes detected by RNA-seq that were down-regulated in response to 6AN, compared to DMSO control cells (A38Lg subclone, detailed in Supplementary Data 3).

| GO Terms | # of Genes | % of Genes | P-value |
| --- | --- | --- | --- |
| Cell Cycle | 226 | 12.2 | 2.5e−57 |
| Acetylation | 465 | 25.2 | 5.6e−57 |
| Phosphoprotein | 935 | 50.6 | 2.5e−55 |
| M-phase | 135 | 7.3 | 1.2e−52 |
| DNA Metabolic Process | 153 | 13.2 | 2.6e−40 |
| Nucleus | 582 | 31.5 | 1.4e−34 |
| DNA Replication | 82 | 4.4 | 1.0e−33 |
| Chromosome Segregation | 45 | 2.4 | 3.1e−24 |
| DNA Repair | 88 | 4.5 | 5.6e−24 |
| Cytoplasm | 444 | 24.0 | 3.5e−23 |
| ATP Binding | 221 | 12.0 | 4.1e−22 |
| Cellular Response to Stress | 125 | 6.8 | 1.6e−19 |
| Chromosome Organization | 107 | 5.8 | 9.3e−17 |
| Microtubule-based Process | 70 | 3.8 | 3.6e−16 |
| Nucleotide Binding | 244 | 13.2 | 4.2e−16 |
| Cytoskeleton | 113 | 6.1 | 3.2e−15 |
| Ubl Conjugation | 103 | 5.6 | 9.5e−12 |
| DNA Recombination | 36 | 1.9 | 1.6e−11 |
| Macromolecular Complex Assembly | 115 | 6.2 | 3.0e−10 |

Figures 6E, 6F:
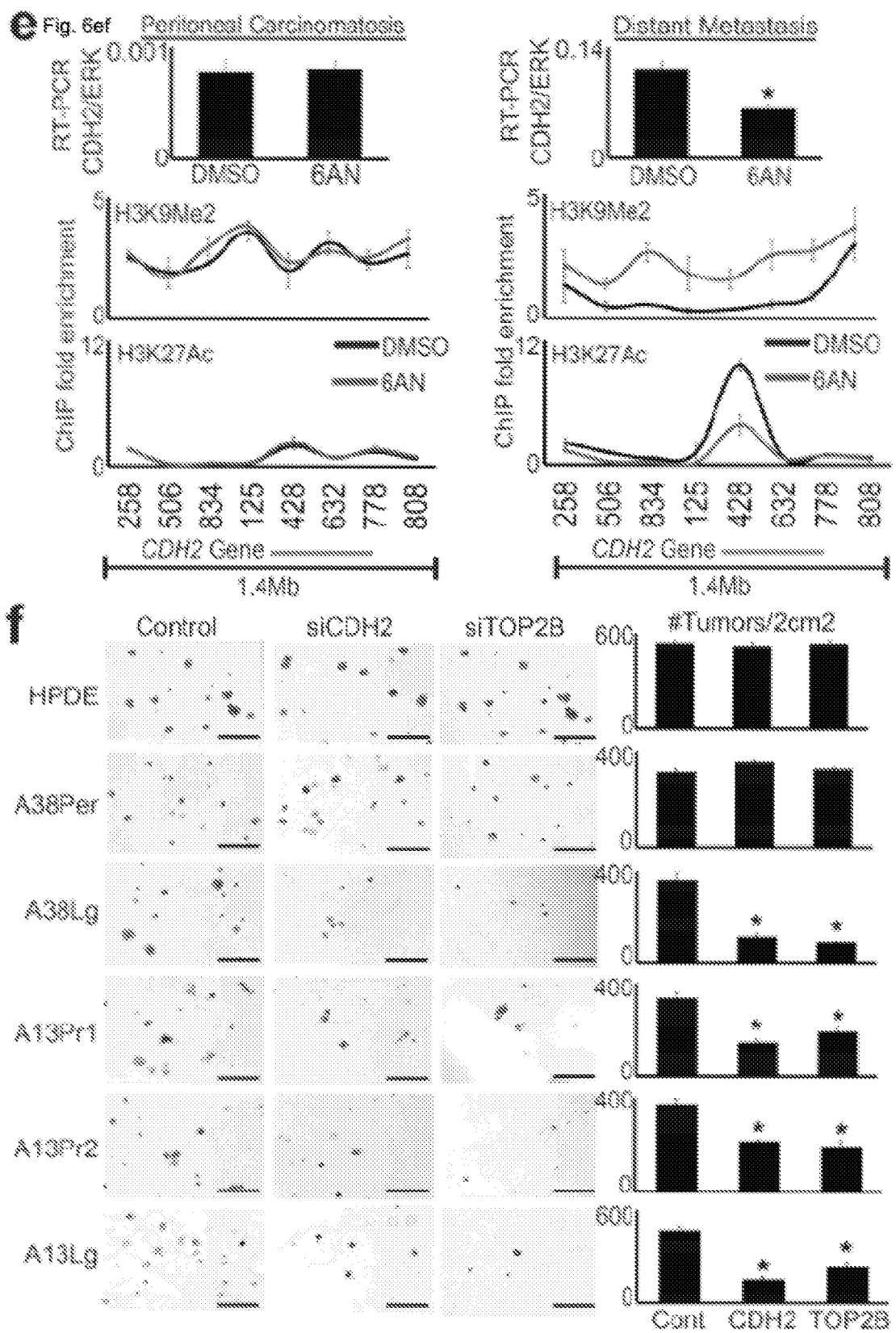
Figures 21A, 21B, 21C:
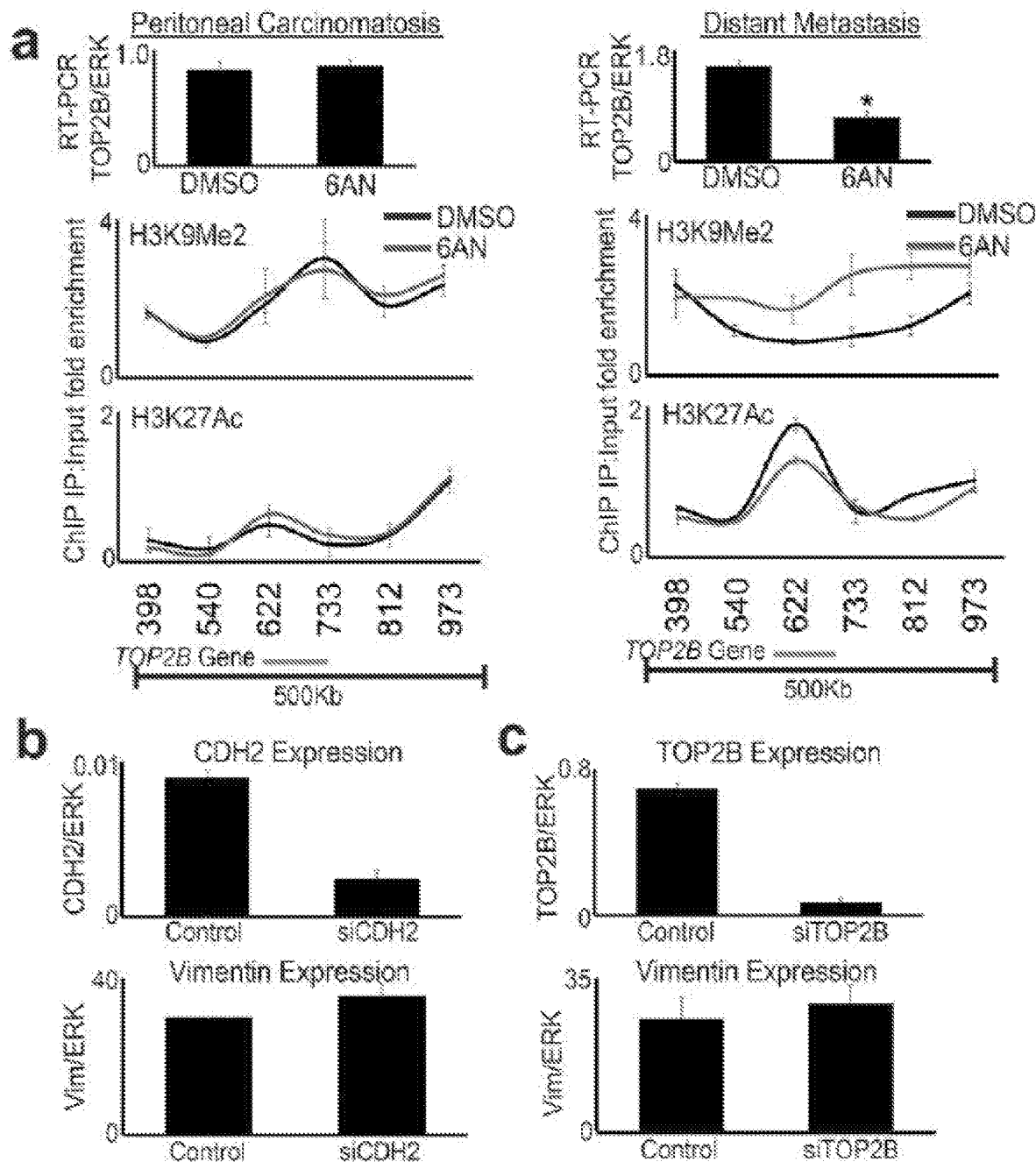
FIGS. 21A-21C relates to reprogramming of the TOP2B locus in response to 6AN.
Figure 22:
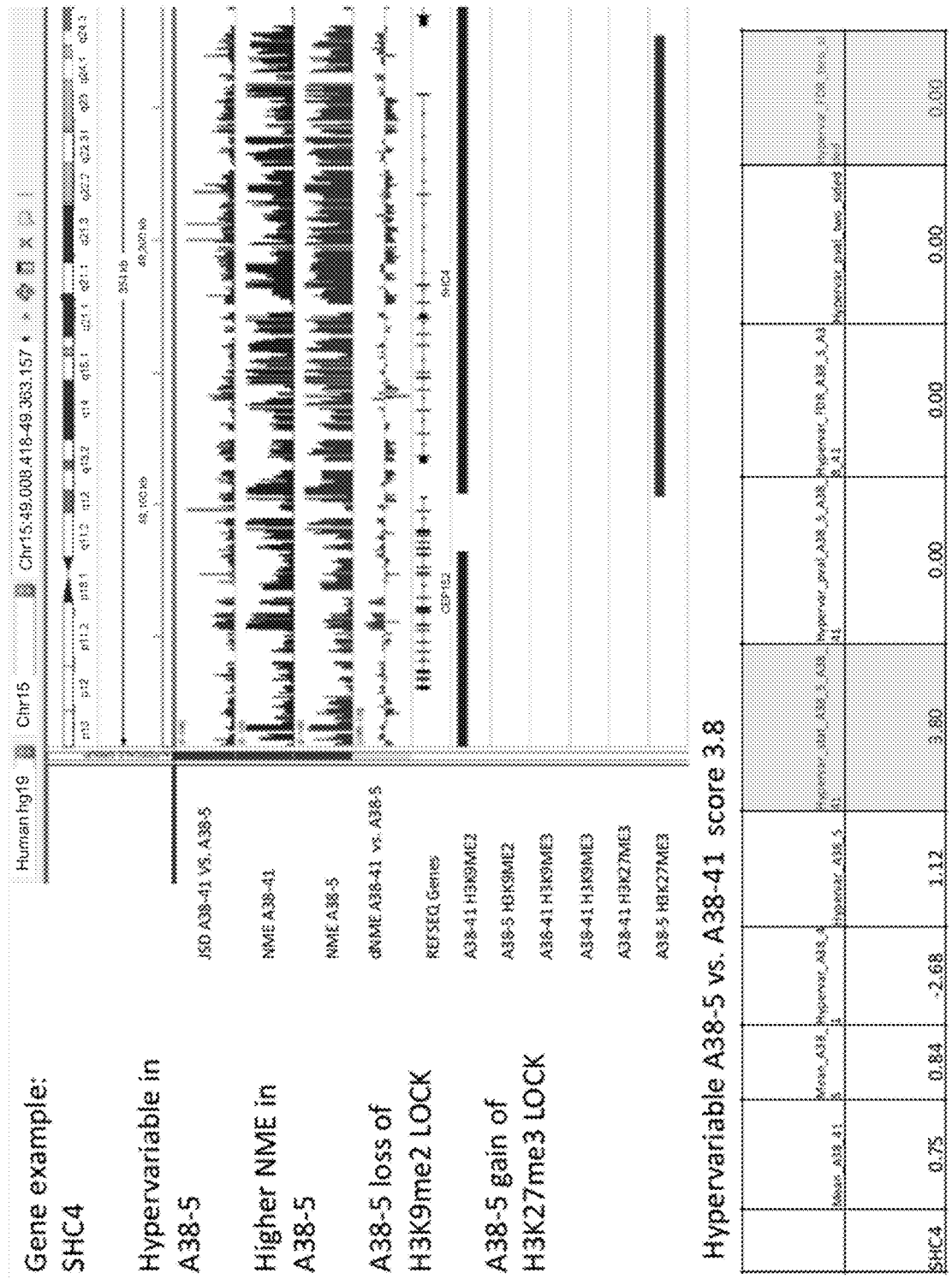
FIG. 22 is a screen shot illustrating data directly linking loss of large-scale heterochromatic regions as described herein to increased variability of gene expression, allowing for increased phenotypic plasticity. An example is a gene SHC4 that is involved in ERK signaling and tumor invasion and metastasis. Its expression variability statistical index measured by single cell RNA experiments is +1.12 in the A38-5 (epigenomically altered, distant metastatic) line in the paper, and −2.68 in the corresponding A38-41 (epigenomically stable, locally invasive) line, with a FDR p value of 0.00.

The above findings led us to hypothesize that 6AN-ablation of tumorigenicity in distant metastatic subclones might be mediated through epigenetic control of cancer-related genes important to maintain tumorigenic capacity. To validate this, we selected two candidate genes for in-depth experiments: N-cadherin (CDH2) and topoisomerase 2β (TOP2B). CDH2 and TOP2B are both thought to be important for cancer progression, are not known to be mutated in PDAC, can be therapeutically targeted, were recurrently over-expressed across distant metastatic and primary tumor precursor subclones by RNA-seq (Supplementary Data 3), and were selectively repressed by 6AN which we confirmed with RT-PCR (FIG. 6e top panels). Furthermore, CDH2 was located within a reprogrammed LOCK targeted by 6AN, and TOP2B was located immediately adjacent to a LOCK boundary. ChIP-qPCR assays performed on control and 6AN treated cells showed nearly identical enrichments for H3K9Me2 and H3K27Ac across these gene loci in the peritoneal subclone (FIG. 6e left panels and FIG. 21a). In contrast, 6AN treatments on the matched lung metastasis from the same patient resulted in enrichment of H3K9Me2 across both loci with concordant reductions of H3K27Ac over the CDH2 genic region (FIG. 6e right panels, FIG. 21a). This strongly suggested that a major downstream effect of 6AN treatments was epigenetic repression of over-expressed cancer genes. We therefore performed RNAi experiments to test whether knockdown of these genes might be important to selectively maintain tumorigenicity. Indeed, RNAi selectively blocked 3D tumor formation in distant metastatic and precursor subclones that over-expressed CDH2 and TOP2B, with no effect on HPDE cells or peritoneal carcinomatosis (FIG. 6f). Collectively, these targeted validation studies strongly supported conclusions inferred from the sequencing data, in that inhibition of PGD/oxPPP by 6AN selectively targeted gene expression, epigenetic state, and downstream tumorigenic functions of over-expressed cancer genes (CDH2/TOP2B).

As detailed in FIG. 1, a global epigenetic reprogramming occurred during the evolution of distant metastasis. The immunohistochemical (IHC) stains against H3K9Me2/3 performed on tumor sections from 6 subclones collected from two patients who presented with widespread peritoneal carcinomatosis (a: patient A124, b: patient A141) showed similar strong nuclear staining across all primary tumor and peritoneal subclones. Similar stains on 6 subclones from two patients who presented with widespread distant metastases (c: patient A125, d: patient A132) showed progressive loss of nuclear staining that initiated in primary tumor subclones that seeded metastases (middle panel) and was further lost (c) or stably inherited (d) in the liver metastases. Scale bars=100 μm for IHC, 20 μm for IF. IHC against the indicated modifications performed on tumor sections representing 4 paired subclones from a patient (patient A38) that presented with both peritoneal carcinomatosis and distant metastases shows that the peritoneal precursor subclone in the primary tumor that seeded carcinomatosis inherited strong nuclear staining of heterochromatin modifications as seen in the parental clone that founded the neoplasm. In contrast, the primary tumor precursor subclone that seeded distant metastases showed cell-to-cell variation in staining, with complete loss of staining in the paired lung metastasis. Staining for the euchromatin modification H3K36Me3 remained stable across all subclones. Similar to IHC on tissues (e), western blots on cells lines collected from the peritoneal subclone (Per), liver metastasis, and lung metastasis from patient A38 also showed loss of heterochromatin modifications in distant metastatic subclones, with corresponding increased acetylation. Levels of H3K27Me3 and H3K36Me3 did not differ between subclones. Densitometry summary of western blot findings for the indicated histone modifications across cell lines from distant metastatic subclones compared to peritoneal carcinomatosis (n=8 biological replicates, error bars=s.e.m., *p<0.01).

As detailed in FIG. 2, an epigenomic reprogramming of chromatin domains during PDAC subclonal evolution was observed. Representative (left panels) and total summarized (right panels) ChIP-seq experiments revealed loss of H3K9Me2 from LOCKs between peritoneal (A38Per) and distant metastatic and primary tumor precursor subclones (others). H3K27Me3 remained strong in all subclones. Bisulfite-seq data on cell lines (A38, A13, top panel) and frozen tissue samples (A124, A125 panels) showed that samples from local regional spread and parental clones (A38Per, A124PrF, A124Per, A125PrF) possessed hypermethylated LOCKs. In contrast, distant metastatic subclones (A125Lv1/2, A13Lg, A38Lv, A38Lg) and their primary tumor subclones (A125PrS, A13Pr1, A13Pr2) showed hypomethylation of DNA across the same LOCK regions. Global levels of H3K36Me3, H3K27Ac, and DNA methylation within ECDs did not show any clear differences between subclones. In contrast, distant metastatic subclones and primary tumor subclones displayed local reprogramming of H3K36Me3 and H3K27Ac specifically over DE genes within ECDs, compared to the same DE genic ECD regions from A38Per.

As detailed in FIG. 3, reprogrammed chromatin domains encode divergent malignant properties. A38Lg was remarkably resistant to $H_2O_2$ treatments compared to A38Per. MTT signals reflect cell viability normalized to untreated controls. n=4 technical replicates, *p<0.03. Western blots for proteins involved in epithelial and EMT differentiation were differentially expressed between A38Per and A38Lg, as predicted by GO analyses of reprogrammed DE genes from LOCKs. A38Lg was completely resistant to gemcitabine compared to A38Per, as predicted by GO analyses of reprogrammed DE genes from ECDs. MTT signals reflect cell viability normalized to untreated controls. n=4 technical replicates, *p<0.01. A38Lg possessed elevated levels of γH2AX by western blot, consistent with activation of DNA repair pathways. Western blots showed that A38Lg lost hyperphosphorylated ERK and was resistant to ERK targeted therapy, compared to A38Per. MTT signals reflect cell viability, normalized to untreated controls. n=4 technical replicates, *p<0.03. A38Lg also lost sensitivity to KRAS knockdown by matrigel®3D tumor forming assays, compared to A38Per. n=4 technical replicates, *p<0.01.

As detailed in FIG. 4, hyperactive glucose metabolism and 6PG depletion were observed in distant metastatic subclones. MTT assays performed on equal numbers (20K) of viable, growth-arrested cells from the indicated subclones showed greatly elevated signal (oxidoreductase activity) across distant metastatic subclones. compared to HPDE and local-regional PDAC samples (n=4 technical replicates for each, error bars=s.d.m., *p<$10^{-5}$). Normalized cell counts for the indicated samples incubated with (+) or without (−) 10 mM glucose and treated with 1 mM $H_2O_2$ as indicated (+, −) for 24h showed that normal HPDE cells were sensitive to $H_2O_2$ under either glucose condition (as expected), whereas local-regional PDAC samples were resistant to $H_2O_2$ irrespective of glucose availability (n=3 technical replicates for each, error bars=s.d.m). In contrast, distant metastatic subclones were sensitive to $H_2O_2$ when glucose was not present in the media (n=3 technical replicates for each, error bars=s.d.m, *p<0.001). Simplified schematic of $^{13}C$-(1,2)-labeled glucose flow through glycolysis and the PPP. Glucose that enters the oxidative branch of the PPP has one labeled carbon cleaved during conversion of 6PG to Ru5P (m+1), whereas glucose that travels through glycolysis or the non-oxidative PPP retains both labeled carbons (m+2). Note that cross-talk allows glucose with either labeling pattern to re-enter the other pathway and incorporate. LC-MS for nucleotides and lactate showed that these downstream metabolites acquired greatly elevated $^{13}C$-1,2 labels from glucose in the lung metastasis from patient A38 (A38Lg), compared to its paired peritoneal subclone (A38Per, n=3 biological replicates, error bars=s.d.m., *p<0.01). Steady state LC-HRMS measurements for 6PG showed either complete (ND: not detected) or near complete loss of metabolite across distant metastases and their precursors compared to peritoneal carcinomatosis and HPDE cells.

As detailed in FIG. 5, A PGD-dependence in distant metastatic subclones was observed. Western blots against indicated histone modifications performed on paired peritoneal (A38Per) and distant metastatic (A38Lg) subclones from the same patient showed that global levels of reprogrammed H3K9Me2/3 and acetylation in A38Lg were reversed by removal of glucose from the media (left panel), PGD RNAi (middle panel), and 6AN treatments (right panel). Western blots on A38Lg indicated that PGD knockdown by RNAi did not perturb expression of other PPP components or KRAS. PGD RNAi did not affect the ability of normal HPDE cells or local-regional PDAC samples to form tumors in 3D matrigel® assays (representative photomicrographs shown with quantified numbers of tumors/well, n=4 technical replicates for each, error bars=s.d.m.). In contrast, PGD RNAi significantly reduced tumor formation across all distant metastatic subclones that were available for testing from the rapid autopsy cohort (n=4 technical replicates for each, error bars=s.d.m., *p<0.01). Scale bars: 200 μm.

as illustrated in FIG. 6, A reversal of reprogrammed chromatin, tumorigenicity, and malignant gene expression programs by 6AN was observed. Densitometry summary of western blots performed on 8 biological replicates, error bars=s.e.m., *p<0.01. 6AN selectively reversed reprogrammed H3K9Me2 and acetylation across most distant metastatic subclones, with minimal or non-recurrent effects on H3K27Me3 or H4K20Me3. Densitometry summary of western blots performed on 6 biological replicates, error bars=s.e.m.. 6AN had minimal effects on histone modifications across normal (HPDE, fibroblast) or local-regional PDAC samples. 6AN ablated tumor formation in 3D matrigel® assays (n=4 technical replicates for each, error bars=s.d.m., *p<0.01, scale bars: 200 μm) and 3D tumorsphere assays across distant metastastic subclones. 6AN had minimal effects on local-regional PDAC samples by either assay 6AN also blocked the ability of distant metastatic subclones to form tumors when injected into 3D organotypic stromal cultures (n=3 technical replicates for each, error bars=s.d.m., *p<0.05; scale bars: 200 μm). Real-time RT-PCR (top panels) showed that the distant metastatic subclone (A38Lg) over-expressed CDH2 relative to the peritoneal subclone (A38Per) from the same patient, and that expression was repressed by 6AN (n=4 technical PCR replicates from two biological replicate experiments, error bars: s.d.m., *p=0.002). ChIP assays for H3K9Me2 and H3K27Ac with PCR primers (location indicated by numbers) spaced across the 1.4 Mb chromatin domain showed that 6AN induced spreading of H3K9Me2 across the locus with corresponding loss of H3K27Ac in A38Lg, with no effect on A38Per (n=2 biological replicates, error bars=s.e.m.). RNAi against both CDH2 and TOP2B selectively blocked tumor formation in distant metastatic and precursor subclones that over-expressed these genes by RNA-seq, with no effect on A38Per or HPDE cells (n=4 technical replicates for each, error bars=s.d.m., *p<0.01; scale bars: 200 μm). Specific RNAi knockdown of gene expression is shown.

As illustrated in FIG. 7, reprogrammed chromatin across distant metastatic subclones was detected. Western blots showed minimal or inconsistent changes for the indicated histone modifications between local-regional PDAC samples, including A38Per (Per). In contrast, a panel of distant metastatic subclones showed recurrent changes in specific modifications, compared to A38Per. Reprogramming was also observed between primary tumor subclones (Pr1, Pr2) and the lung met. from the same patient.

As illustrated in FIG. 8, the specificity of reprogrammed histone modifications was established. Ki67 stains showed similar cell cycle rates for peritoneal and the matched lung met grown in serum, and serum-free media (SFM) arrested growth. Serial cell counts for the indicated times confirmed equal growth rates and growth arrest in SFM. GO analysis on RNA-seq data from cells cultured in serum vs. SFM further confirmed growth arrest in SFM (lung data, peritoneal gave identical results). Western blots showed persistence of reprogrammed chromatin modifications in serum/proliferative (−) and SFM/growth arrested (+) cells. Treatment of the peritoneal sub clone with PDAC chemotherapies (Gem: Gemcitabine, G+FU: Gemcitabine+5–Fluorouracil) did not induce loss of methylation or gain of acetylation as seen between peritoneal and distant metastases, confirming that reprogramming was unrelated to treatment effects.

As illustrated in FIG. 9, an enrichment of heterochromatin modifications within LOCKs was identified. Plots of ChIP-seq read densities normalized to inputs for histone modifications (left labels) showed that heterochromatin modifications (H3K9Me2/3, H3K27Me3) were enriched in regions that were called LOCKs (0% to 100%, bottom panel labels) for each subclone (indicated above graphs). In contrast, euchromatin modifications (H3K36Me3, H3K27Ac) were depleted from LOCKs.

As illustrated in FIG. 10, the reprogramming of H3K9Me3 in LOCKs during PDAC subclonal evolution was observed. ChIP-seq data from paired peritoneal (A38Per) and lung (A38Lg) metastatic subclones detected dramatic reduction of H3K9Me3 in A38Lg, that overlapped with H3K9Me2 (which marks LOCK domains). Similar data for patient A13, which also showed loss of H3K9Me3 from LOCK regions in A13Pr2/A13Lg subclones, compared to the A13Pr1 primary tumor subclone.

As illustrated in Figure FIG. 11, the local reprogramming of DE gene loci within LOCKs was observed. Mapping DE genes from RNA-seq (distant mets and precursors vs. A38Per) to LOCKs revealed reciprocal changes in H3K27Me3 and H3K27Ac/H3K36Me3/DNA methylation around genes downregulated in LOCKs. The opposite changes in H3K27Me3 and H3K27Ac/H3K36Me3 were detected from genes upregulated in LOCKs. DNA methylation remained high in these regions. P-values for each comparison are listed in Supplementary Data 3.

As illustrated in FIG. 12, an enrichment of euchromatin modifications within ECDs was observed. Plots of ChIP-seq read densities normalized to inputs for histone modifications (left labels) showed that euchromatin modifications (H3K36Me3,H3K4Me3, H3K27Ac) were enriched in regions that were called ECDs (0% to 100%, bottom panel labels) for each subclone (indicated above the graphs). In contrast, heterochromatin modifications (H3K9Me2/3, H3K27Me3) were depleted from ECDs.

As illustrated in FIG. 13, the reprogramming of large LOCKs during PDAC evolution was observed. H3K9Me3 was enriched and DNA hypomethylated in large LOCK domains. Striking reprogramming of H3K9Me3/2 and DNA methylation was detected in a subset of A38 large LOCKs. d, H3K9Me3 was also enriched across large HPDE LOCKs. Several examples of reprogrammed domains between samples were obtained.

As illustrated in FIG. 14, malignant heterogeneity between A38 subclones was discovered. Oxidoreductase capacity was measured with MTT assays performed on equal numbers of growth-arrested cells in the absence of serum, and MTT signals normalized to total cell numbers per well. Consistent with GO results, A38Lg possessed higher oxidoreductase activity. n=4 technical replicates.

NADPH/NADP levels were measured with enzyme cycling assays on equal numbers of growth arrested cells. More NADPH/million cells was detected in A38Lg. n=2 biological replicates. A38Per and A38Lg maintained well/poorly differentiated morphology in patient tissues and across three separate in vitro culture conditions as indicated. IF performed on fixed tissues from the primary tumor showed loss of E-cadherin with gain of vimentin in the precursor subclone that seeded A38Lg, consistent with EMT. RNAi knockdown of KRAS blocked 3-D tumor formation in suspension assays more efficiently in A38Per than A38Lg. n=4 technical reps.

As illustrated in FIG. 15, it was found that rearrangements were targeted to Large LOCKs and ECDs. Total breakpoints were not significantly enriched within Large LOCKs or ECDs. Unlike typical LOCKs, Large LOCK/ECD breakpoints were significantly joined to breakpoints from homologous domains to form rearrangements. Examples of Large LOCK rearrangements that generated translocations and amplifications were observed.

As illustrated in FIG. 16, an enhanced glucose metabolism with depleted 6PG levels across distant metastases was observed. Extra-cellular glucose consumption and lactate secretion were elevated in distant mets relative to per. (n=3). Schematic of glycolytic (outside) and PPP (boxed) metabolites with intra-cellular metabolite levels plotted for each sample. Data represent LC-MS signals normalized to protein (n=3-5).

As illustrated in FIG. 17, it was found that 6AN targets glucose metabolism and the PGD step of the PPP. 6AN selectively slowed rates of extra-cellular glucose consumption and lactate secretion in metastatic subclones with no effect on glutamine/glutamate. 6AN reduced incorporation of intracellular 013-labeled glucose into metabolites downstream of the PPP. c, 6AN greatly increased metabolite levels of PGD substrate (6PG) and upstream metabolites (G1,5L) with corresponding reductions in downstream products.

As illustrated in FIG. 18, it was found that 6AN selectively modulated the reprogrammed chromatin state of distant metastatic subclones. 6AN treatments generally increased global H3K9Me2 with corresponding decreased acetylation in distant metastatic subclones. Normal cells and local-regional PDACs did not show such changes. 6AN changes persisted after 3d treatment (+) followed by removal of 6AN from the media (+−) for an additional 3d.

As illustrated in FIG. 19, it was found that 6AN targeted reprogrammed LOCK regions. Mapping 6AN repressed DE genes to A38Lg LOCKs revealed that these were located in reprogrammed LOCK-E1 regions. ChIP-seq on DMSO vs. 6AN treated A38Lg detected a quantitative increase in LOCK-wide H3K9Me2 from reprogrammed regions (as aligned to A38Per LOCKs). ChIP-seq also detected 6AN-reduced H3K27Ac specifically from genes repressed in LOCKs with unchanged H3K27Me3.

Figures 20A, 20B, 20C:
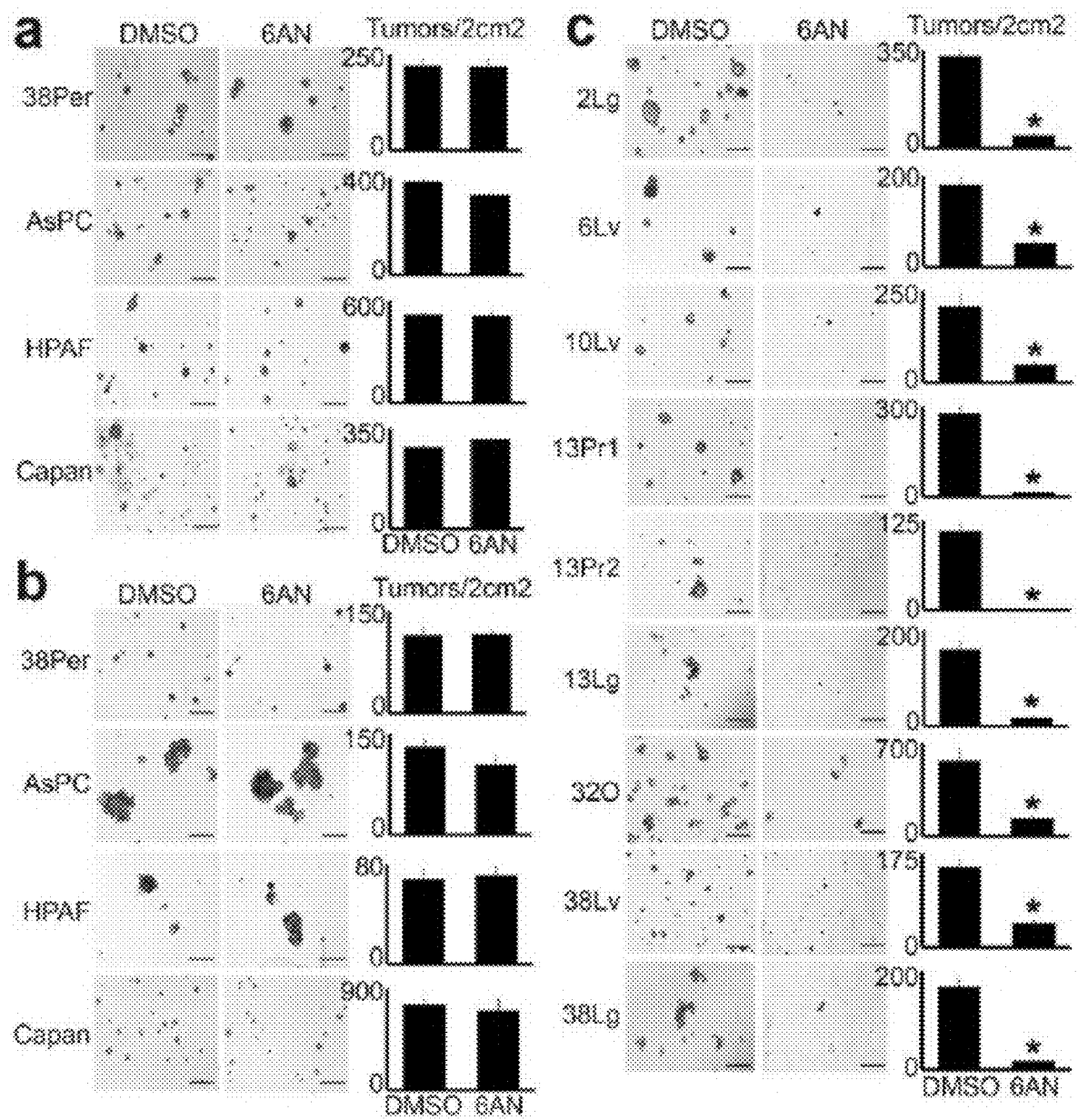
FIGS. 20A-20C relate to 6AN selectively blocked tumor formation in distant metastatic subclones.

As illustrated in FIG. 20, 6AN selectively blocked tumor formation in distant metastatic subclones. a, 6AN did not interfere with the ability of local-regional PDAC samples to form tumors in 3-D matrigel® assays or b, in 3-D suspension tumorsphere assays. n=2-4. c, In contrast, 6AN strongly blocked the ability of distant metastatic subclones to form tumors in 3-D suspension tumorsphere assays (shown) and 3-D matrigel® assays (FIG. 5b). n=4, p<0.003. Scalebars: 200 uM.

As illustrated in FIG. 21, the reprogramming of the TOP2B locus in response to 6AN was observed. RT-qPCR (top panels) showed that 6AN selectively repressed TOP2B the lung metastatic subclone. Similarly, ChIP assays showed that 6AN induced spreading of H3K9Me2 across the locus in the lung metastasis, with no effect on the paired peritoneal subclone. Representative RT-qPCR verified RNAi knockdown of CDH2 and TOP2B with minimal effect on vimentin (normalized to ERK, which was equally expressed across all conditions).

DISCUSSION

The first major result of this study was widespread epigenetic reprogramming during the evolution of distant metastasis in the absence of metastasis-specific driver mutations, i.e. those not already present in the founder clone of the primary tumor. These involved large-scale reprogramming of histone H3K9 and DNA methylation within large heterochromatin domains (LOCKs and hypomethylated blocks), as well as regional changes in gene regulatory modifications (H3K27Ac, H3K36Me3). Second, these changes specified heterogeneous malignant properties that emerged during subclonal evolution. In particular, evolutionarily divergent subclones from the same patient showed changes in gene expression from reprogrammed regions consistent with their individual malignant properties, including oxidoreductase capacity, differentiation state, chemoresistance, oncogene addiction, and patterns of genome instability. Third, it was the PGD step of the oxPPP that controlled aspects of reprogrammed chromatin and tumorigenicity in distant metastatic subclones, as shown by metabolomics, genetic knockdown of PGD, chemical inhibition of PGD, and knockdown of downstream target genes. This strongly suggests that this anabolic glucose pathway was selected during the evolution of distant metastasis to maintain malignant epigenetic state and tumorigenic properties.

These findings also raise several important but complex questions, which we are pursuing in other studies. Perhaps the most complicated pertains to the extent of epigenetic and malignant heterogeneity between subclones across patients. Just to answer this in a single patient, a combination of whole-genome mapping, RNA-seq, bioinformatics, and several downstream experimental approaches were required. We hypothesize that such heterogeneity is a function of evolutionary time: patients who present with late-stage, widely metastatic disease may possess more epigenetic and malignant divergence between subclones in their tumors than patients who present with early-stage disease. This possibility underscores the pressing need to detect cancers early, before such malignant heterogeneity arises.

Also unclear are the precise mechanisms whereby PGD/oxPPP activity controls global epigenetic state, which are likely to be complex. This could be mediated through any of the known oxPPP-dependent changes in cellular metabolism, including redox balance, fatty acid biosynthesis, and/or ribose biosynthesis, any of which can affect global epigenetic state through control of metabolite cofactors that activate or inhibit entire classes of chromatin modifying enzymes. PGD activity itself is also complex and subject to several modes of regulation, including transcriptional overexpression, post-transcriptional repression, post-translational modification, protein:protein interactions, substrate availability, feedback inhibition, cross-talk with other pathways, and subcellular localization including a highly conserved yet uncharacterized nuclear fraction (C. Lyssiotis, personal communication). PGD-dependence may be selected for by any of these mechanisms during the evolution of distant metastasis in different patients.

A final question is how global epigenetic changes are targeted to specific chromatin domains that encode gene expression changes during subclonal evolution. We hypothesize that transcription factors and chromatin modifying enzymes that directly bind these regions play major roles in targeting the reprogramming events, and several candidates were recurrently over-expressed in our RNA-seq datasets. This includes the histone demethylase KDMJA (LSD1), which could be particularly important since we previously showed that this enzyme controls LOCK reprogramming and other studies have shown that it regulates breast cancer metastasis.

In summary, our findings in conjunction with deep sequencing studies on many of the same samples reported here suggest a model whereby driver mutations arise early to initiate PDAC tumorigenesis, followed by a period of subclonal evolution that generates heterogeneous metabolic, epigenetic, and malignant properties. Like driver mutations, those properties that confer increased fitness to cells that acquire them may be selected for and clonally expanded during invasive tumor growth and metastatic spread. The strong oxPPP-PGD dependence we observe in distant metastatic subclones could reflect such selection: distant metastatic sites provide ample glucose to fuel the pathway, pathway products (glucose-dependent NADPH) reduce oxygen species encountered within the sites, and the pathway itself is coupled to epigenetic programs that promote tumorigenesis. As such, reversal of malignant epigenetic programs by targeting the oxPPP could represent an effective therapeutic strategy for metastatic PDAC, one of the most lethal of all human malignancies.

Data Deposits

All ChIP-seq, RNA-seq, and bisulfite-seq sequencing data has been deposited online (GEO Number: GSE63126) at the following URL: ncbi.nlm.nih.gov/geo/query/acc.cgi?token=sxyjkaqsvfalheh&acc=GSE63126

Methods Summary

Tissue samples and cell lines were previously collected from PDAC patients by rapid autopsy, sequenced-validated, and monitored for mycoplasma as previously described. Low passage (2-17) rapid autopsy cell lines were cultured at 37° C. in DMEM with 10% fetal bovine serum (FBS, Gibco). For MTT assays, 15,000 cells/well were plated into 96 well plates in triplicate, treated 12 hours later, and assayed after 24 hr (glucose responses) or 6 days (chemotherapy) with CellTiter96 (Promega). For glucose response assays, nutrient-deplete DMEM (no glucose, glutamine, pyruvate, or serum) was used with addition of glucose as indicated. For glucose-dependent oxidative stress analysis, cells plated in triplicate and grown to 80% confluence followed by incubation in nutrient-deplete DMEM containing 10% dialyzed FBS with or without 10 mM glucose and 1 mM $H_2O_2$ for 24 hours. Cells were then washed with PBS, trypsinized, and viable cells counted with a hemocytometer. Glucose uptake and lactate secretion were measured with a YSI 7100 Bioanalyzer as described in the supplementary methods. For $^{13}C$-1,2 glucose tracing and steady state metabolite profiling, the Q Exactive MS (QE-MS; Thermo Scientific) coupled to liquid chromatography (LC Ultimate 3000 UHPLC) was used for metabolite separation and detection as previously described. Detailed conditions are provided in the supplementary methods.

Histones were acid extracted as described and western blots performed on 3.5 ug histones, which were checked by Ponceau stains prior to western blot to ensure equal loading. Densitometry was performed with ImageJ software. RNA was extracted with Trizol reagent (Life Technologies) and isopropanol precipitated. Genomic DNA was purified with MasterPure DNA extraction reagents (Epicenter). Immunohistochemistry, H&E staining, and immunofluorescence on formalin-fixed, paraffin-embedded (FFPE) tissue microarray sections (TMAs) were performed according to standard procedures. Antibodies used for western blot, IHC, and ChIP are listed in Table 11.

TABLE 11

Antibodies and conditions used for western blots, immunostain, and ChIP experiments

| Antibody | Source | Catalogue # | Western dilution | Immuno dilution |
|---|---|---|---|---|
| CDH1 | Cell Signaling | 4065 | 1/500 | 1/100, IF |
| Vimentin | NeoMarkers | Ms-129-P | 1/500 | 1/100, IF |
| G6PD | Cell Signaling | 8866S | 1/500 | N/A |
| PGD | Cell Signaling | 13389S | 1/500 | N/A |
| TKT | Cell Signaling | 8616S | 1/500 | N/A |
| TALDO1 | Santa Cruz | Sc-134795 | 2 ug/ml | N/A |
| ERK1/2 | Cell Signaling | 4696S | 1/500 | N/A |
| p-ERK1/2 | Cell Signaling | 4370S | 1/500 | N/A |
| KRAS | Santa Cruz | Sc-30 | 2 ug/ml | N/A |
| RPE | Santa Cruz | Sc-162124 | 2 ug/ml | N/A |
| RPIA | Abcam | Ab181235 | 1/500 | N/A |
| CD44 | Cell Signaling | 5640S | 1/500 | N/A |
| Epcam | Millipore | CBL251 | 1/500 | N/A |
| CDH2 | Cell Signaling | 4061S | 1/250 | N/A |
| H3K9Me2 | Abcam | ab1220 | 1/10,000 | 1/5000 IHC, IF |
| H3K9Me3 | Abcam | ab8898 | 1/10,000 | 1/5000 IHC |
| H3K27Me3 | Millipore | 07-449 | 1/7500 | N/A |
| H3K9Ac | Millipore | 07-352 | 1/10,000 | N/A |
| H3K36Me3 | Abcam | ab9050 | 1/10,000 | 1/5000 IHC |
| H3K27Ac | Abcam | ab4729 | 1/5000 | N/A |
| H4K20Me3 | Millipore | 07-463 | 1/1000 | 1/5000 IHC |
| H4K16Ac | Millipore, Abcam | 07-329, ab109463 | 1/10,000 | N/A |
| total H3 | Abcam | ab1791 | 1/30,000 | N/A |
| total H4 | Abcam | ab10158 | 1/30,000 | N/A |
| γH2AX | Abcam | ab11174 | 1/5,000 | N/A |

RNAi experiments were performed with siRNA transfections (Oligofectamine, Life Technologies) using negative control siRNA (Sigma, SIC001) and pre-designed siRNA oligonucleotides against indicated genes in parallel (Sigma, PGD: SASI_Hs02_00334150, CDH2: SASI_Hs01_00153995, TOP2B: SASI_Hs02_00311874). siRNAs against mutant KRAS$^{G12V}$ (CUACGCCAACAG-CUCCAAC) (SEQ ID NO:1) were custom designed. Cells were incubated with siRNAs for 4 days after transfection and harvested. For drug treatments in 2-D, cells were grown to 70-80% confluency and treated for 3 days with 250 uM 6AN or DMSO negative control.

3-D matrigel assays were adapted from Cheung et al. (Control of alveolar differentiation by the lineage transcription factors GATA6 and HOPX inhibits lung adenocarcinoma metastasis. Cancer Cell 23, 725-38 (2013)). Briefly, 2-D cultures were trypsinized into single cells, 4,000cells/mL were suspended and thoroughly mixed in ice-cold DMEM containing 5% matrigel (BD systems) and 2% FBS (+/−DMSO/6AN as needed), 500 ul plated in quadruplicate into 24 well ultra-low attachment plates, and incubated for at least 7 days to allow tumor growth. Well-formed tumors were then counted and representative photographs taken with an EVOS instrument. 3-D suspension tumorsphere assays were performed with 20,000 starting cells/well in ultra-low attachment 6 well plates as described, and tumors counted/photographed after at least 7 days of tumor growth.

Organotypic tumor forming assays were adapted from Ridky et al. (P.A. Invasive three-dimensional organotypic neoplasia from multiple normal human epithelia. Nat Med 16, 1450-5 (2010)) and Andl et al. (Epidermal growth factor receptor mediates increased cell proliferation, migration, and aggregation in esophageal keratinocytes in vitro and in vivo. J Biol Chem 278, 1824-30 (2003)). Briefly, 6 well permeable transwell plates (Costar 3414) were overlayed with 1 mL type 1 collagen containing 10×DMEM (acellular layer). Human dermal fibroblasts (ATCC) were suspended (12×10$^6$ cells/mL) in a mixture of ice cold 10×DMEM, 10% FBS, 52.5% collagen, and 17.5% matrigel (cellular layer), thoroughly mixed, and 2 mL/well plated over the acellular layer. The mixture was allowed to partially solidify for approximately 15 minutes at 37° C., followed by triplicate injection of 1×10$^6$ PDAC (suspended in 20 ul DMEM) cells into the cellular layer. Cells were incubated for 24 hours in fibroblast growth media above and below the inserts to initiate contraction of the discs. Fresh media with DMSO or 6AN was then added and replenished every 2 days for 6 additional days, followed by addition of DMEM with DMSO or 6AN underneath the inserts (no media on the top) for an additional 7 days. Discs were harvested, fixed overnight in 10% formalin, thinly sectioned, paraffin embedded, and stained with H&E. Tumors were photographed and measured with an Olympus BX53 microscope using cellSens Standard software.

Tests for statistical significance (two-tailed students t-test) were performed on data collected from technical replicate (performed in parallel at the same time) or biological replicate (performed at different times) experiments as indicated in the figure legends using excel software for western blot densitometry, MTT assays, and tumor measurements. Whole genome bisulfite sequencing and RNA-seq were performed with HiSeq instruments (Illumina) as described in Hansen et al. (Increased methylation variation in epigenetic domains across cancer types. Nat Genet 43, 768-75 (2011)). ChIP assays were performed as previously described for fixed cells with sonication. For ChIP-qPCR, equal amounts of paired input/IP DNA were amplified by real-time PCR (Roche LightCycler96) and fold enrichments calculated. Primer sequences are listed in Supplementary Table 11. For ChIP-seq, immunoprecipitated and input DNA was further sheared to 200-300 bp fragments, size-selected on agarose gels, and sequenced on either HiSeq (Illumina) or SOLiD (Applied Biosystems) formats with comparable results. IP sequencing reads were normalized to their corresponding inputs. Sequencing procedures, bioinformatics methods including domain calls, and statistical analyses are described in detail within the supplementary methods section.

TABLE 12

Real-time PCR primer sequences used for ChIP-qPCR and RT-PCR experiments

| Locus/ Assay | Primer Name: Sequence (5'-3') | SEQ ID NO: |
|---|---|---|
| CDH2 ChIP | Chr18_24.258F: GCTCAGCCCTGTATCAGCCAGC | 2 |
| CDH2 ChIP | Chr18_24.258R: GGGTTACAGGTATGAGCCACTGC | 3 |
| CDH2 ChIP | Chr18_24.506F: AATGGAGAAGTCAGGAATGTAGTCC | 4 |
| CDH2 ChIP | Chr18_24.506R: GTATTTCATTTATCAAGTTGCAGCTCC | 5 |

TABLE 12-continued

Real-time PCR primer sequences
used for ChIP-qPCR and RT-PCR experiments

| Locus/Assay | Primer Name: Sequence (5'-3') | SEQ ID NO: |
|---|---|---|
| CDH2 ChIP | Chr18_24.834F: TTTGCTTCTCACTCCAAGTTCATCC | 6 |
| CDH2 ChIP | Chr18_24.834R: CAACCTCAGGAACAATGCATCAGC | 7 |
| CDH2 ChIP | Chr18_25.125.6F: CGAAACAGTCCAGCTGCTATGG | 8 |
| CDH2 ChIP | Chr18_25.125.6R: CTTGGCTATTGTGACTGGTACTGC | 9 |
| CDH2 ChIP | Chr18_25.428.000F: CCAATGCACTAATTTAATGTCATGC | 10 |
| CDH2 ChIP | Chr18_25.428.000R: CGTGCTAATTTCTATGGTACACTGG | 11 |
| CDH2 ChIP | Chr18_25.632F: CCTAATCCAATATGCCTGGTGTCC | 12 |
| CDH2 ChIP | Chr18_25.632R: CTGGAAGTCTGAGATCAAGGTGC | 13 |
| CDH2 ChIP | Chr18_25.778F: AATAATCACGAAGCACTTCTGTATTGC | 14 |
| CDH2 ChIP | Chr18_25.778R: TCACCAGCAGACATAGTCATACTTCC | 15 |
| CDH2 ChIP | Chr18_25.808F: CCTTGGAGGTGGAGTCTACAGAGG | 16 |
| CDH2 ChIP | Chr18_25.808R: CTGCTAGCGTAGCCATCTGAGATCG | 17 |
| TOP2B ChIP | Chr3_25.398F: GCCCTGTCTTCCCAGAATCATTGC | 18 |
| TOP2B ChIP | Chr3_25.398R: CATGAAGCCTATGAAGATCATTATGG | 19 |
| TOP2B ChIP | Chr3_25.540F: TTTAGCCAGCAAGTATTCTAGCATGG | 20 |
| TOP2B ChIP | Chr3_25.540R: GTCAGTGTGATTCAGTAACAATGATGG | 21 |
| TOP2B ChIP | Chr3_25.622F: CCTGCTCAAGGCTGACATGTCACC | 22 |
| TOP2B ChIP | Chr3_25.622R: GTCGGACTCGATGGTCAGCACTGG | 23 |
| TOP2B ChIP | Chr3_25.733F: AACCCGAAACTTTCAATGCACTTGG | 24 |
| TOP2B ChIP | Chr3_25.733R: CTTCCTCTATAGTGAAGACCCTAGG | 25 |
| TOP2B ChIP | Chr3_25.812F: TATGGCCATTCTTGCAGCAGTAAGG | 26 |
| TOP2B ChIP | Chr3_25.812R: AAAGTTGGCTAAGGACATGAATAGGC | 27 |
| TOP2B ChIP | Chr3_25.973F: GGAGATTCCCTCAGGTGCCTATACC | 28 |
| TOP2B ChIP | Chr3_25.973R: CTGGTGTTCCAGGCACCACTGAGG | 29 |
| CDH2 RT-PCR | CDH2F: TTATTACTCCTGGTGCGAGT | 30 |
| CDH2 RT-PCR | CDH2R: GAGCTGATGACAAATAGCGG | 31 |
| TOP2B RT- | TOP2BF: GTTACAGGTGGTCGTAATGGTT | 32 |
| TOP2B RT- | TOP2BR: TTGGCTTCAGAAGTCTTCATCA | 33 |

Supplementary Methods

YSI metabolite analysis. Metabolite consumption (glucose and glutamine) and production (lactate and glutamate) were measured using a YSI 7100 Bioanalyzer. Indicated cell lines were plated at day-1 in a 6-well plate. At day 0 cells were counted (3 wells) or cultured in either regular medium or medium supplemented with the indicated compound. Tissue culture supernatants (1 mL, n=3, each condition) were harvested 72 hours after cell plating. Tissue culture conditions were optimized to ensure nutrient availability and exponential cell growth. Metabolite consumption/production data were normalized to cell number area under the curve, as previously described (Lee et al 2014: PMID: 24998913). The area under the curve (AUC) was calculated as $N(T)d/\ln2(1-2^{T/d})$, where $N(T)$ is the final cell count, d is doubling time, and T is time of experiment. Doubling time was calculated as $d=(T)[\log(2)/\log(Q2/Q1)]$, where Q1 is starting cell number and Q2 is final cell number, as determined by manual counting using a hemocytometer.

LC-HRMS Metabolite Profiling. LC-HRMS samples were prepared and analyzed as described in Liu et al. (Development and quantitative evaluation of a high-resolution metabolomics technology. Anal Chem 86, 2175-84 (2014)). For glucose tracing experiments, cells were plated into 6 well plates in triplicate, grown in DMEM with 10% FBS until 70-80% confluent, washed 2× with nutrient deplete DMEM, and incubated in nutrient deplete DMEM containing 10 mM $^{13}C$-1,2 labeled glucose (Cayman) and 10% dialyzed FBS (Invitrogen) for an additional 36 hours. Additional replicates were also included and counted at the end of the experiment for normalization. Metabolism was quenched by quickly removing media and adding 1 mL pre-chilled (−80° C.) LC-MS grade 80% methanol (Sigma), incubated at −80° C. for at least 20 minutes, followed by scraping into the methanol and pelleting of metabolites by centrifugation. For drug treatments, cells were incubated in standard DMEM+/−DMSO/6AN for 36 hours, followed by incubation in labeled glucose media+/−DMSO/6AN for an additional 36 hours, quenched and pelleted as above. Pellets were reconstituted in equal volumes of 1:1 LC-MS grade acetonitrile:methanol and water and 5 ul were injected to the LC-QE-MS for analysis. For steady state measurements cells were incubated in growth media (DMEM with 10% FBS for PDACs, keratinocyte serum-free media for HPDE) until they reached 80-90% confluence, followed by 48 hours in DMEM without serum (for PDACs, since the standard growth media for comparison HPDE cells also did not contain serum). Metabolism was then quenched with methanol and metabolites pelleted as above. Pellets were reconstituted into a volume normalized to protein content (15 uL of 1:1 acetonitrile:methanol and 15 uL of water was used per 1 mg protein) and analyzed by LC-QE-MS. Raw data collected from the LC-QE-MS was processed on Sieve 2.0 (Thermo Scientific) using a targeted frame-seed that included glycolytic/PPP metabolites as required for the analysis. The output file including detected m/z and relative intensity in different samples is obtained after data processing, and replicates of selected metabolites from each sample were graphed and presented as shown in the figures.

Preparation of sequencing libraries. Libraries were prepared from 2-10 ng of IP ChIP DNA and 100 ng of input DNA and sequenced on Illumina HiSeq (APF laboratory). Briefly, samples were checked for quality and concentration from 150-250 bp on a bioanalyzer. DNA was end-repaired using Klenow polymerase in 58 ul of reaction buffer. For IP DNA, Klenow was diluted 1:5. Samples were incubated at 20° C. for 30 minutes and subsequently purified on QIAquick PCR purification columns. A-tails were then added to the DNA with Klenow and dATP in NEB buffer 2 at 37° C. for 30 minutes and cleaned with Qiagen MiniElute PCR purification columns. Sequencing adapters were then ligated onto the DNA for 15 minutes at room temperature followed by cleaning with MiniElute columns. Samples were then run on 2% agarose gels and DNA from 216 bp-366 bp (DNA plus adapters) were cut from the gel and purified with Qiagen Gel extraction kits. Concentrations were then checked on a bioanalyzer and 8 ng were PCR amplified with Phusion polymerase (Fisher) for 15 cycles (10 sec 98° C., 30 sec 65° C., 30 sec 72° C.) followed by 5 minutes at 72° C. Samples were then cleaned with Ampure kits (Illumina) and washed with 80% ethanol. DNA samples were resuspended at the end of the cleanup into 17.5 ul buffer EB (Qiagen) and subjected to next generation sequencing on Illumina HiSeq platform according to manufacturer's instructions. For SOLID sequencing, ChIP DNA was prepared and samples were processed according to manufacturer's protocols in the Johns Hopkins CRBII core facility.

BS-Seq data processing. 100 bp paired-end HiSeq2000 sequencing reads were aligned by BSmooth bisulfate alignment pipeline (version 0.7.1) as previously described in Hansen et al. (Increased methylation variation in epigenetic domains across cancer types. Nat Genet 43, 768-75 (2011)). Briefly, reads were aligned by Bowtie2 (version 2.0.1) against human genome (hg19) as well as the lambda phage genome. After alignment, methylation measurements for each CpG were extracted from aligned reads. We filtered out measurements with mapping quality <20 or nucleotide base quality on cytosine position <10 and we also removed measurements from the 5' most 10 nucleotides of both mates. Then, bsseq package in BSmooth was used to identify small and large differentially methylated regions (DMRs). Only CpGs with at least coverage of 3 in all samples were included in our analysis. For small DMRs, smooth window of 20 CpGs or 1 kb was used, and t-statistic cutoff of −4.6, 4.6 and methylation difference greater than 20% were used for identifying small DMRs. While for large DMRs, smooth window of 200 CpGs or 10,000 bps was used, and t-statistic cutoff of −2, 2, methylation difference greater than 10% and length of DMRs >5 kb were used for identifying large DMRs.

RNA-Seq data processing. 100 bp paired-end HiSeq2000 sequencing reads were aligned against human genome (hg19) by OSA (version 2.0.1) with default parameters. After alignment, only uniquely aligned reads were kept for further analysis. Gene annotation information was downloaded from ENSEMBL (ensembl.com, release 66). Reads count for each gene of all samples were estimated using HTSeq (huber.embl.de/users/anders/HTSeq/doc/overview.html) and then were used to identify differentially expressed (DE) genes using DESeq package. Genes with FDR<0.01 and fold-change>1.5 were considered DE genes.

Chip-seq data processing. For 46 bp paired-end Illumina HiSeq2000 sequencing data, reads were aligned against human genome (hg19) using BWA with default parameters as described in Li et al. (Fast and accurate short read alignment with Burrows-Wheeler transform. Bioinformatics 25, 1754-60 (2009)). After alignment, duplicate reads were removed and only uniquely aligned reads were kept for further analysis. For 48 bp single-end Solid sequencing data, reads were aligned using Bowtie[7] with default parameters and only uniquely aligned reads were kept for further analysis. For narrow histone modification peaks (H3K4Me3 and H3K27Ac), MACS2 were used for peak calling with default parameters[8]. For broad histone modification enrichments (H3K36Me3, H3K27me3, and H3K9Me2/3), peak calling were performed using RSEG which is based on hidden Markov model (HMM) and specifically designed for identifying broad histone peaks (see Song et al. (Identifying dispersed epigenomic domains from ChIP-Seq data. Bioinformatics 27, 870-1 (2011))).

Identifying large chromatin domains. We define LOCK domains for heterochromatin modifications (H3K9Me2/H3K27Me3) based on the peak calling results from RSEG. Briefly, peaks shorter than 5 kb were first removed to prevent regions with many nearby, short peaks being called as LOCKs. Then, neighboring peaks with distance less than 20 kb were merged to into one domain. Merged regions greater than 100 Kb identified in both biological replicates were called LOCKs. We noticed another unique subset of LOCKs that were invariably larger than 500 kb, strongly enriched with H3K9Me3, depleted of H3K9Me2 and H3K27Me3, and flanked by strong peaks of H3K27Me3 at the boundaries. Because of this, we defined these LOCKs by H3K9Me3 regions with length greater than 500 kb and less than 50% of their length overlapped with H3K27me3. Finally, the large regions (>50 kb) between heterochromatin domains that contained at least one gene with corresponding euchromatic H3K4Me3/H3K27Ac regulatory peaks were defined as ECDs. Because we found that H3K27Ac alone was sufficient for these calls, H3K4Me3 was also used for the initial test dataset with A38Per/Lg, but not required in subsequent datasets (A13Pr1/2, A13Lg). All codes used for domain calls are available upon request.

Defining different gene groups. Genes were classified as belonging within euchromatin (>50% of genic region located in ECDs) or heterochromatin (>50% of genic region located in those heterochromatin domains including LOCKs and G-LOCKs). A handful of other genes that did not fit these criteria and were classified as "other".

Quantifying and enrichment plotting of ChIP-seq and RNA-seq. To plot each histone modification on defined large chromatin domains and their flanking regions, we divided flanking sequences of chromatin domains into bins with fixed length (in bp) and domains themselves into bins with fixed percentage of each domain length. ChIP enrichment was measured and normalized as described in Hawkins et al. (Distinct epigenomic landscapes of pluripotent and lineage-committed human cells. Cell Stem Cell 6, 479-91 (2010)). In brief, the number of reads per kilobase of bin per million reads sequenced was calculated for each ChIP and its input control (denoted as $RPKM_{ChIP}$ and $RPKM_{input}$). ChIP enrichment is measured as $\Delta RPKM = RPKM_{ChIP} - RPKM_{input}$ and ChIP enrichment regions should have $\Delta RPKM > 0$. Then all $\Delta RPKM$ were normalized to a scale between 0 and 1 and the average normalized ChIP enrichment signals across all large chromatin domains were plotted for each histone mark. RNA-Seq data was also normalized by the number of reads per kilobase of bin per million reads sequenced and plotted similarly.

Supplementary Data

Supplementary Data 1. This lists numbers of sequencing reads (total reads and uniquely aligned reads) for all replicate samples for ChIP-seq, WGBS, and RNA-seq experiments and includes correlation coefficients between the replicate samples.

Supplementary Data 1A: Summary of ChIP-seq reads for all replicate samples

| Samples (Name_replicate#_IP antibody) | Total reads | Uniquely aligned reads | |
|---|---|---|---|
| 38Per_1_K27ac | 27,100,820 | 23,396,028 | |
| 38Per_2_K27ac | 20,750,076 | 17,913,278 | |
| 38Lg_1_K27ac | 22,821,996 | 19,946,514 | |
| 38Lg_2_K27ac | 25,996,970 | 22,475,058 | |
| 38Per_1_K9ac | 27,148,594 | 22,200,344 | |
| 38Per_2_K9ac | 25,585,898 | 18,706,456 | |
| 38Lg_1_K9ac | 26,607,612 | 21,750,232 | |
| 38Lg_2_K9ac | 28,316,524 | 23,222,230 | |
| 38Per_1_K4me3 | 28,059,734 | 23,718,542 | |
| 38Per_1_K4me3 | 43,068,697 | 20,704,383 | |
| 38Lg_2_K4me3 | 24,455,456 | 21,184,788 | |
| 38Lg_2_K4me3 | 44,715,633 | 17,458,603 | |
| 38Per_1_K36me3 | 44,738,783 | 23,961,134 | |
| 38Per_2_K36me3 | 25,140,434 | 19,239,814 | |
| 38Lg_1_K36me3 | 25,532,398 | 18,263,078 | |
| 38Lg_2_K36me3 | 48,929,336 | 24,747,992 | |
| 38Per_1_K27me3 | 26,546,612 | 21,523,318 | |
| 38Per_1_K27me3 | 47,076,156 | 21,613,912 | |
| 38Lg_2_K27me3 | 25,528,442 | 20,886,386 | |
| 38Lg_2_K27me3 | 44,444,667 | 16,568,247 | |
| 38Per_1_K9me2 | 69,629,048 | 55,830,176 | |
| 38Per_K9me2_2 | 64,949,506 | 51,281,848 | |
| 38Lg_K9me2_1 | 51,787,694 | 39,725,736 | |
| 38Lg_2_K9me2 | 71,421,136 | 55,643,850 | |
| 38Per_1_K9me3 | 28,530,078 | 18,843,038 | |
| 38Per_2_K9me3 | 30,869,994 | 19,860,544 | |
| 38Lg_1_K9me3 | 33,055,178 | 20,251,534 | |
| 38Lg_2_K9me3 | 36,205,418 | 22,568,940 | |
| 38Per_1_Input | 28,748,102 | 22,637,100 | for 38Per_1 K16ac, K27ac, K9ac, K4me3, K27me3, K9me2 and K9me3 |
| 38Per_1_Input | 43,698,893 | 20,955,594 | for 38Per_1 Solid K4me3, K36me3 and K27me3 |
| 38Per_1_Input | 78,376,368 | 61,062,024 | for 38Per_1 K9me2 |
| 38Per_2_Input | 26,162,800 | 20,358,392 | for 38Per_2 K16ac, K9ac, K36me3, K9me2 and K9me3 |
| 38Per_2_Input | 22,795,752 | 17,717,432 | for 38Per_2 K27ac |
| 38Per_2_Input | 73,425,982 | 57,237,686 | for 38Per_2 K9me2 |
| 38Lg_1_Input | 30,391,444 | 23,128,054 | for 38Lg_1 K16ac, K27ac, K9ac and K9me3 |
| 38Lg_1_Input | 26,527,468 | 20,878,592 | for 38Lg_1 K36me3 and K9me2 |
| 38Lg_1_Input | 56,918,912 | 44,006,646 | for 38Lg_1 K9me2 |
| 38Lg_2_Input | 24,372,670 | 21,204,480 | for 38Lg_2 K16ac, K27ac, K9ac, K4me3, K27me3 and K9me3 |
| 38Lg_2_Input | 43,698,893 | 19,884,219 | for 38Lg_2 Solid K4me3 and K27me3 |
| 38Lg_2_Input | 42,655,553 | 25,391,128 | for 38Lg_2 Solid K36me3 |
| 38Lg_2_Input | 82,576,576 | 65,151,312 | for 38Lg_2 K9me2 |
| 13Pr2_1_K27Me3 | 45,562,122 | 35,405,382 | |
| 13Pr2_2_K27Me3 | 48,647,198 | 37,601,820 | |
| 13Pr2_1_K36Me3 | 50,525,636 | 40,320,884 | |
| 13Pr2_2_K36Me3 | 43,172,826 | 34,777,556 | |
| 13Pr2_1_K9Me3 | 52,034,354 | 28,398,244 | |
| 13Pr2_2_K9Me3 | 47,846,284 | 27,025,984 | |
| 13Pr2_1_K27Ac | 39,057,664 | 32,754,504 | |
| 13Pr2_2_K27Ac | 45,988,666 | 38,419,042 | |
| 13Pr2_1_K9Me2 | 36,367,760 | 27,747,040 | |
| 13Pr2_2_K9Me2 | 49,421,058 | 36,685,524 | |
| 13Pr2_1_Input | 42,932,496 | 34,453,136 | for 13Pr2_1 K27Ac and K9Me2 |
| 13Pr2_2_input | 39,166,036 | 31,527,030 | for 13Pr2_2 K27Ac and K9me2 |
| 13Pr2_1_Input | 43,812,050 | 33,019,642 | for 13Pr2_1 K36Me3 |
| 13Pr2_2_Input | 42,483,790 | 32,000,834 | for 13Pr2_2 K36Me3 |
| 13Pr2_1_Input | 36,646,218 | 27,841,600 | for 13Pr2_1 K27Me3 and K9Me3 |
| 13Pr2_2_Input | 37,605,184 | 28,502,806 | for 13Pr2_2 K27Me3 and K9Me3 |
| 13Pr1_1_K27Me3 | 42,464,788 | 32,291,936 | |
| 13Pr1_2_K27Me3 | 42,717,990 | 32,886,274 | |
| 13Pr1_1_K36Me3 | 45,628,144 | 34,403,256 | |
| 13Pr1_2_K36Me3 | 47,010,260 | 35,169,858 | |

-continued

| Samples (Name_replicate#_IP antibody) | Total reads | Uniquely aligned reads | |
|---|---|---|---|
| 13Pr1_1_K27Ac | 42,969,352 | 36,362,084 | |
| 13Pr1_2_K27Ac | 52,912,056 | 43,709,782 | |
| 13Pr1_1_K9Me3 | 43,261,454 | 27,946,136 | |
| 13Pr1_2_K9Me3 | 48,134,638 | 30,111,834 | |
| 13Pr1_1_K9Me2 | 51,237,440 | 37,126,410 | |
| 13Pr1_2_K9Me2 | 44,260,552 | 34,079,972 | |
| 13Pr1_1_K4Me3 | 47,817,718 | 40,460,332 | |
| 13Pr1_2_K4Me3 | 39,916,242 | 34,219,430 | |
| 13Pr1_1_Input | 27,015,968 | 21,991,728 | for 13Pr1_1 K9Me3 and K9Me2 |
| 13Pr1_2_Input | 42,754,918 | 34,651,668 | for 13Pr1_2 K9Me3 and K9Me2 |
| 13Pr1_1_Input | 37,703,540 | 30,589,064 | for 13Pr1_1 K36Me3 and K27Ac |
| 13Pr1_2_Input | 37,251,906 | 30,188,840 | for 13Pr1_2 K36Me3 and K27Ac |
| 13Pr1_1_Input | 45,330,014 | 36,495,018 | for 13Pr1_1 K27Me3 and K4Me3 |
| 13Pr1_2_Input_ | 41,671,660 | 33,507,094 | for 13Pr1_2 K27Me3 and K4Me3 |
| 13Lg_1_K27Me3 | 46,174,838 | 35,837,518 | |
| 13Lg_2_K27Me3 | 47,763,132 | 36,963,900 | |
| 13Lg_1_K36Me3 | 48,735,296 | 39,047,890 | |
| 13Lg_2_K36Me3 | 44,439,570 | 35,973,060 | |
| 13Lg_1_K27Ac | 52,682,716 | 44,187,348 | |
| 13Lg_2_K27Ac | 38,043,964 | 32,298,344 | |
| 13Lg_1_K9Me3 | 44,449,474 | 25,717,050 | |
| 13Lg_2_K9Me3 | 49,020,848 | 28,456,692 | |
| 13Lg_1_K9Me2 | 40,580,872 | 31,979,380 | |
| 13Lg_2_K9Me2 | 42,760,754 | 33,395,094 | |
| 13Lg_1_input | 53,086,242 | 42,631,966 | for 13Lg_1 K27Ac and K9Me2 |
| 13Lg_2_input | 41,676,088 | 33,503,572 | for 13Lg_2 K27Ac and K9Me2 |
| 13Lg_1_Input | 40,822,392 | 31,354,916 | for 13Lg_1 K36Me3 |
| 13Lg_2_Input | 45,292,342 | 35,189,166 | for 13Lg_2 K36Me3 |
| 13Lg_1_Input | 49,243,126 | 37,741,490 | for 13Lg_1 K27Me3 and K9Me3 |
| 13Lg_2_Input | 47,226,322 | 36,317,110 | for 13Lg_2 K27Me3 and K9Me3 |
| HPDE_1_K27Me3 | 41,619,730 | 1,644,221,182 | |
| HPDE_2_K27Me3 | 45,844,562 | 1,870,133,582 | |
| HPDE_1_K36Me3 | 38,327,244 | 28,084,826 | |
| HPDE_2_K36Me3 | 35,519,752 | 27,012,400 | |
| HPDE_1_K27Ac | 52,294,724 | 43,428,888 | |
| HPDE_2_K27Ac | 35,271,886 | 30,001,598 | |
| HPDE_1_K9Me3 | 49,006,354 | 31,150,780 | |
| HPDE_2_K9Me3 | 49,995,186 | 31,313,578 | |
| HPDE_1_K9Me2 | 47,415,884 | 36,297,824 | |
| HPDE_2_K9Me2 | 47,621,364 | 36,772,334 | |
| HPDE_1_K4Me3 | 45,262,500 | 39,528,934 | |
| HPDE_2_K4Me3 | 34,511,978 | 30,181,046 | |
| HPDE_1_Input | 50,286,666 | 40,743,792 | for HPDE_1 K9Me3 and K9Me2 |
| HPDE_2_Input | 45,780,736 | 37,154,676 | for HPDE_2 K9Me3 and K9Me2 |
| HPDE_1_Input | 36,424,754 | 29,600,008 | for HPDE_1 K36Me3 and K27Ac |
| HPDE_2_Input | 48,330,362 | 39,054,926 | for HPDE_2 K36Me3 and K27Ac |
| HPDE_1_Input | 38,269,792 | 30,829,930 | for HPDE_1 K27Me3 and K4Me3 |
| HPDE_2_Input | 37,635,368 | 30,421,766 | for HPDE_2 K27Me3 and K4Me3 |
| 38Lg_DMSO_1_K27Me3 | 45,364,340 | 33,889,440 | |
| 38Lg_DMSO_2_K27Me3 | 37,628,254 | 29,077,804 | |
| 38-5_DMSO_1_K9Me2 | 57,024,354 | 42,891,924 | |
| 38Lg_DMSO_1_K27Ac | 44,665,878 | 37,664,038 | |
| 38-5_DMSO_1_Input_batch4 | 69,705,942 | 56,571,128 | for 38-5_DMSO_1 K9Me2 |
| 38Lg_DMSO_1_Input | 37,296,752 | 30,470,440 | for 38Lg_DMSO_1 K27Ac |
| 38Lg_DMSO_1_Input | 49,727,864 | 40,284,668 | for 38Lg_DMSO_1 K27Me3 |
| 38Lg_DMSO_2_Input | 40,505,458 | 32,886,902 | for 38Lg_DMSO_2 K27Me3 |
| 38Lg_6AN_1_K27Me3 | 50,310,568 | 39,528,064 | |
| 38Lg_6AN_2_K27Me3 | 38,884,546 | 32,325,978 | |
| 38-5_6AN_1_K9Me2 | 33,324,396 | 24,956,330 | |
| 38Lg_6AN_1_K27Ac | 40,895,998 | 34,565,998 | |
| 38-5_6AN_1_Input_batch4 | 42,480,878 | 34,537,520 | for 38-5_6AN_1 K9Me2 |
| 38Lg_6AN_1_Input_batch3 | 40,615,920 | 33,033,908 | for 38Lg_6AN_1 K27Ac |
| 38Lg_6AN_1_Input_batch5 | 45,637,332 | 37,039,730 | for 38Lg_6AN_1 K27Me3 |
| 38Lg_6AN_2_Input_batch5 | 36,771,474 | 29,835,218 | for 38Lg_6AN_2 K27Me3 |
| Total | | 7,441,856,062 | |

Supplementary Data 1B: Summary of WGBS reads for all replicate samples

| Samples | Total reads | Aligned reads | Total CpGs | Aligned CpGs | Coverage per replicate |
|---|---|---|---|---|---|
| 38Per rep1 | 281,674,084 | 234,515,645 | 28,217,448 | 24,736,894 | 5.74 |
| 38Per rep2 | 279,677,926 | 233,819,498 | 28,217,448 | 24,668,800 | 5.65 |
| 38Lg rep1 | 246,354,388 | 242,041,867 | 28,217,448 | 24,079,382 | 4.96 |
| 38Lg rep2 | 293,066,340 | 203,060,037 | 28,217,448 | 24,568,234 | 5.87 |
| 38-Lv rep1 | 481,671,728 | 394,675,778 | 28,217,448 | 25,699,745 | 12.06 |
| 38-Lv rep2 | 550,721,820 | 443,244,002 | 28,217,448 | 25,797,654 | 13.57 |
| 13Pr2 rep1 | 470,251,572 | 378,466,223 | 28,217,448 | 25,763,514 | 11.83 |
| 13Pr2 rep2 | 515,334,056 | 421,725,378 | 28,217,448 | 25,287,251 | 12.01 |
| 13Pr1 rep1 | 421,949,244 | 340,966,300 | 28,217,448 | 25,733,843 | 10.58 |
| 13Pr1 rep2 | 383,229,986 | 308,746,570 | 28,217,448 | 25,613,462 | 9.58 |
| 13Lg rep1 | 489,959,480 | 400,936,046 | 28,217,448 | 25,342,333 | 11.59 |
| 13Lg rep2 | 505,568,682 | 415,435,288 | 28,217,448 | 25,358,384 | 11.74 |
| HPDE rep1 | 319,334,144 | 259,838,538 | 28,217,448 | 25,498,338 | 8.14 |
| HPDE rep2 | 409,472,974 | 329,823,993 | 28,217,448 | 25,755,008 | 10.07 |
| 38Lg DMSO rep1 | 381,562,458 | 313,237,618 | 28,217,448 | 25,509,209 | 9.67 |
| 38Lg DMSO rep2 | 462,809,566 | 378,726,614 | 28,217,448 | 25,716,790 | 11.67 |
| 38Lg 6AN rep1 | 668,822,798 | 546,162,307 | 28,217,448 | 25,987,966 | 16.62 |
| 38Lg 6AN rep2 | 408,683,276 | 329,596,955 | 28,217,448 | 25,586,266 | 10.20 |
| A124PerMet | 388,402,336 | 313,722,746 | 28,217,448 | 25,551,642 | 7.39 |
| A124Pr | 348,071,524 | 281,407,466 | 28,217,448 | 25,424,592 | 6.73 |
| Normal | 335,262,856 | 264,003,665 | 28,217,448 | 25,423,437 | 6.37 |
| A125LvMet2 | 299,092,468 | 241,196,683 | 28,217,448 | 24,124,822 | 5.55 |
| A125LvMet1 | 256,878,816 | 210,595,185 | 28,217,448 | 24,190,459 | 5.09 |
| A125Pr2 | 274,964,060 | 226,288,821 | 28,217,448 | 24,326,375 | 5.39 |
| A125Pr1 | 338,097,576 | 277,039,476 | 28,217,448 | 25,344,423 | 6.55 |
| Total | | 7,989,272,699 | | | |

Supplementary Data 1C: Summary of RNA-seq reads for all replicate samples

| Samples | Total reads | Uniquely aligned reads | Genes with at least one read |
|---|---|---|---|
| 38Per rep1 | 136,981,522 | 126,989,515 | 24,629 |
| 38Per rep2 | 209,196,426 | 194,285,575 | 25,767 |
| 38Per SFM rep1 | 131,806,836 | 120,661,977 | 23,750 |
| 38Per SFM rep2 | 170,418,406 | 157,947,694 | 25,204 |
| 38Lg rep1 | 157,009,238 | 146,313,205 | 22,347 |
| 38Lg rep2 | 126,740,896 | 118,431,884 | 21,849 |
| 38Lg SFM rep1 | 157,587,660 | 144,483,739 | 23,085 |
| 38Lg SFM rep2 | 136,421,728 | 124,124,770 | 22,387 |
| 38-Lv rep1 | 121,404,350 | 99,124,421 | 23,033 |
| 38-Lv rep2 | 201,919,638 | 160,412,909 | 24,203 |
| 13Pr2 rep1 | 189,720,644 | 163,161,693 | 25,011 |
| 13Pr2 rep2 | 154,397,366 | 132,746,732 | 24,122 |
| 13Pr1 rep1 | 194,020,194 | 152,395,660 | 25,013 |
| 13Pr1 rep2 | 159,731,916 | 124,045,393 | 24,300 |
| 13Lg rep1 | 258,937,646 | 222,764,245 | 25,530 |
| 13Lg rep2 | 104,375,982 | 89,301,099 | 24,908 |
| HPDE rep1 | 142,777,652 | 115,147,712 | 23,274 |
| HPDE rep2 | 148,752,028 | 119,731,612 | 23,348 |
| 38Per DMSO rep1 | 103,160,056 | 90,683,198 | 23,718 |
| 38Per DMSO rep2 | 205,086,938 | 175,208,405 | 25,285 |
| 38Per 6AN rep1 | 163,145,386 | 144,907,391 | 24,514 |
| 38Per 6AN rep2 | 163,346,616 | 145,684,561 | 24,049 |
| 38Lg DMSO rep1 | 183,580,116 | 158,065,524 | 23,609 |
| 38Lg DMSO rep2 | 177,808,970 | 156,924,338 | 23,334 |
| 38Lg 6AN rep1 | 231,471,388 | 201,726,950 | 24,544 |
| 38Lg 6AN rep2 | 181,401,400 | 157,469,565 | 23,376 |
| Total | | 3,742,739,767 | |

Supplementary Data 1D: Summary of sequencing correlation coefficients for each replicate

| Samples | Modification | Correlation coefficients between replicates |
|---|---|---|
| 38Per | K4Me3 | 0.8487501 |
| 38Per | K36Me3 | 0.7908561 |
| 38Per | K27Me3 | 0.8087827 |
| 38Per | K9Me2 | 0.9533903 |
| 38Per | K9Me3 | 0.973981 |
| 38Per | K9Ac | 0.8405352 |
| 38Per | K27Ac | 0.9662306 |
| 38Per | K16Ac | 0.8958976 |
| 38Lg | K4Me3 | 0.8977917 |
| 38Lg | K36Me3 | 0.7457856 |
| 38Lg | K27Me3 | 0.8283084 |
| 38Lg | K9Me2 | 0.9345982 |
| 38Lg | K9Me3 | 0.9870598 |
| 38Lg | K9Ac | 0.8557192 |
| 38Lg | K27Ac | 0.9749662 |
| 38Lg | K16Ac | 0.8634484 |
| 13Pr2 | K27Ac | 0.9795735 |
| 13Pr2 | K27Me3 | 0.957889 |
| 13Pr2 | K36Me3 | 0.970403 |
| 13Pr2 | K9Me2 | 0.9710885 |
| 13Pr2 | K9Me3 | 0.9918936 |

| Samples | Modification | Correlation coefficients between replicates |
|---|---|---|
| 13Pr1 | K27Ac | 0.9797524 |
| 13Pr1 | K27Me3 | 0.9481441 |
| 13Pr1 | K36Me3 | 0.9697859 |
| 13Pr1 | K9Me2 | 0.9238059 |
| 13Pr1 | K9Me3 | 0.9841044 |
| 13Pr1 | K4Me3 | 0.9969566 |
| 13Lg | K27Ac | 0.9824737 |
| 13Lg | K27Me3 | 0.9518218 |
| 13Lg | K36Me3 | 0.9647369 |
| 13Lg | K9Me2 | 0.9505661 |
| 13Lg | K9Me3 | 0.9927826 |
| HPDE | K27Ac | 0.9969341 |
| HPDE | K27Me3 | 0.9694532 |
| HPDE | K36Me3 | 0.9582686 |
| HPDE | K9Me2 | 0.9820727 |
| HPDE | K9Me3 | 0.9655677 |
| HPDE | K4Me3 | 0.991134 |
| 38Lg_DMSO | K27Ac | 0.9523149 |
| 38Lg_DMSO | K27Me3 | 0.9190836 |
| 38Lg_DMSO | K36Me3 | 0.8830686 |
| 38Lg_6AN | K27Ac | 0.9515394 |
| 38Lg_6AN | K27Me3 | 0.9328865 |
| 38Lg_6AN | K36Me3 | 0.8750725 |
|  | Average | 0.9331653 |
|  | Median | 0.9556397 |

Supplementary Data 2. This provides summaries of chromatin domain calls for LOCKs, large LOCKs, and ECDs for each sample including median lengths, ranges, % genome coverage, and levels of individual histone modifications in each type of domain. Median lengths, ranges, and % genome coverage for each individual heterochromatin modification individually (irrespective of domain location) is also included.

Supplementary Data 2A: Summary of large chromatin domains detected by ChIP-seq

| Samples (name, source) | Domains | Nos. | Ranges (bp) | Median lengths (bp) | Total length (bp) | % of genome | K9Me2 enrichment (ΔRPKM) | K9Me3 enrichment (ΔRPKM) | K27Me3 enrichment (ΔRPKM) |
|---|---|---|---|---|---|---|---|---|---|
| A38Per, Peritoneal | LOCKs | 2,648 | 100,001~24,067,001 | 311,251 | 1,547,508,645 | 54.11% | 0.082 | 0.003 | 0.102 |
|  | ECDs | 2,021 | 50,499~8,760,499 | 271,999 | 895,772,411 | 31.32% | −0.116 | −0.225 | −0.139 |
|  | Large LOCKs | 344 | 500,501~10,773,501 | 1,287,251 | 589,313.343 | 20.61% | 0.012 | 0.458 | −0.020 |
| A38Lg, Lung Met | LOCKs | 3,166 | 100,001~14,074,501 | 298,251 | 1,627,719,164 | 56.91% | 0.069 | −0.101 | 0.118 |
|  | ECDs | 2,318 | 50,499~12,388,255 | 241,499 | 838,469,352 | 29.32% | −0.112 | −0.243 | −0.159 |
|  | Large LOCKs | 226 | 505,501~10,428,001 | 1,340,751 | 416,070,225 | 14.55% | 0.004 | 1.040 | −0.152 |
| A13Pr1, Primary 1 | LOCKs | 2,446 | 100,001~30,694,501 | 279,501 | 1,745,065,095 | 61.02% | 0.038 | 0.063 | 0.124 |
|  | ECDs | 2,008 | 50,499~5,944,499 | 255,167 | 914,964,363 | 31.99% | −0.062 | −0.176 | −0.221 |
|  | Large LOCKs | 77 | 504,001~5,223,501 | 994,501 | 97,292,576 | 3.40% | −0.045 | 0.640 | 0.043 |
| A13Pr2, Primary 2 | LOCKs | 2,862 | 100,001~24,749,001 | 298,251 | 1,845,941,860 | 64.54% | 0.065 | 0.051 | 0.107 |
|  | ECDs | 1,968 | 50,499~10,621,499 | 277,249 | 914,565,095 | 31.98% | −0.122 | −0.141 | −0.199 |
|  | GHDs | 50 | 501,501~1,742,001 | 711,001 | 40,355,550 | 1.41% | 0.015 | 0.990 | −0.112 |
| A13Lg, Lung Met | LOCKs | 3,140 | 100,001~31,395,001 | 293,501 | 2,052,192,139 | 71.75% | 0.048 | 0.027 | 0.089 |
|  | ECDs | 1,935 | 50,499~3,447,581 | 207,499 | 672,028,952 | 23.50% | −0.125 | −0.155 | −0.231 |
|  | Large LOCKs | 111 | 500,501~2,878,501 | 735,501 | 100,336,111 | 3.51% | −0.034 | 0.558 | −0.180 |

Supplementary Data 2B: Summary of broad heterochromatin modifications detected by ChIP-seq

| Samples (name, source) | Large histone modifications | Numbers | Ranges (bp) | Median lengths (bp) | Total length (bp) | % of genome |
|---|---|---|---|---|---|---|
| A38Per, Peritoneal | K9Me2 | 2,331 | 100,001~24,067,001 | 335,001 | 1,449,305,831 | 50.68% |
|  | K9Me3 (large LOCKs) | 344 | 500,501~10,773,501 | 1,287,251 | 589,313,343 | 20.61% |
|  | K9me3 (LOCKs) | 711 | 102,001~1,690,501 | 219,501 | 207,546,709 | 7.26% |
|  | K27Me3 | 1,523 | 100,001~1,127,001 | 186,001 | 360,026,522 | 12.59% |

-continued

| Samples (name, source) | Large histone modifications | Numbers | Ranges (bp) | Median lengths (bp) | Total length (bp) | % of genome |
|---|---|---|---|---|---|---|
| A38Lg, Lung Met | K9Me2 | 2,010 | 100,001~14,074,501 | 255,501 | 979,113,009 | 34.23% |
| | K9Me3 (large LOCKs) | 226 | 505,501~10,428,001 | 1,340,751 | 416,070,225 | 14.55% |
| | K9me3 (LOCKs) | 189 | 101,501~1,027,001 | 215,000 | 49,777,688 | 1.74% |
| | K27Me3 | 2,649 | 100,001~2,197,001 | 244,501 | 882,095,148 | 30.84% |
| A13Pr1, Primary 1 | K9Me2 | 1,696 | 100,001~1,428,501 | 176,501 | 407,098,196 | 14.23% |
| | K9Me3 (large LOCKs) | 77 | 504,001~5,223,501 | 994,501 | 97,292,576 | 3.40% |
| | K9me3 (LOCKs) | 1,181 | 100,501~11,051,001 | 322,501 | 573,396,678 | 20.05% |
| | K27Me3 | 2,211 | 100,001~30,694,501 | 232,001 | 803,104,711 | 28.08% |
| A13Pr2, Primary 2 | K9Me2 | 2,693 | 100,001~24,749,001 | 295,501 | 1,738,982,692 | 60.80% |
| | K9Me3 (large LOCKs) | 50 | 501,501~1,742,001 | 711,001 | 40,355,550 | 1.41% |
| | K9me3 (LOCKs) | 505 | 101,001~1,203,001 | 187,501 | 117,705,503 | 4.12% |
| | K27Me3 | 1,828 | 100,001~2,887,501 | 220,001 | 589,055,827 | 20.60% |
| A13Lg, Lung Met | K9Me2 | 3,091 | 100,001~24,749,001 | 283,501 | 1,898,353,591 | 66.38% |
| | K9Me3 (large LOCKs) | 111 | 500,501~2,878,501 | 735,501 | 100,336,111 | 3.51% |
| | K9me3 (LOCKs) | 711 | 101,501~1,748,001 | 194,501 | 168,847,710 | 5.90% |
| | K27Me3 | 2,553 | 100,001~31,395,001 | 237,001 | 1,003,794,552 | 35.10% |

Supplementary Data 3. This provides all p-values calculated for sequencing experiments, as designated by the figure labels. Sensitivity analyses for LOCK domain calls are also included.

Supplementary File 3A: p-values for H3K9Me2 reprogramming across LOCKs

| FIG. 2a: H3K9Me2 Reduction Across LOCKS (vs A38Per) | | | | |
|---|---|---|---|---|
| Samples | K9Me2 Enrichment (ΔRPKM) | p-value (RPKM < A38Per Wilcox Test) | Mb K9Me2 Reduction (vs A38Per) | p-value (Reduced Mb vs A38Per, Chi-square Test) |
| A38Per, Peritoneal | 0.082 | NA (reference) | NA (reference) | N/A (reference) |
| A38Lg, Lung Metastasis | 0.069 | $p < 2.2e-16$ | 763 Mb (52.7%) | $p < 2.2e-16$ |
| A13Pr1, Primary Tumor 1 | 0.038 | $p < 2.2e-16$ | 1110 Mb (76.6%) | $p < 2.2e-16$ |
| A13Pr2, Primary Tumor 2 | 0.065 | $p < 2.2e-16$ | 286 Mb (19.7%) | $p < 2.2e-16$ |
| A13Lg, Lung Metastasis | 0.048 | $p < 2.2e-16$ | 204 (14.1%) | $p < 2.2e-16$ |

Supplementary Data 3B: p-values for reprogrammed euchromatin modifications from DE genes

| FIG. 2e Genes Up-regulated from Euchromatin (vs Peritoneal: A38Per) | | |
|---|---|---|
| Sample | pvalue K27Ac (>A38Per Wilcox) | pvalue K36Me3 (>A38Per Wilcox) |
| A38Lg, Lung Metastasis | p < 2.2e-16 | p < 2.2e-16 |
| A13Pr1, Primary Tumor 1 | p < 2.2e-16 | p < 2.2e-16 |
| A13Pr2, Primary Tumor 2 | p < 2.2e-16 | p < 2.2e-16 |
| A13Lg, Lung Metastasis | p < 2.2e-16 | p < 2.2e-16 |

| FIG. 2e Genes Down-regulated from Euchromatin (vs Peritoneal: A38Per) | | |
|---|---|---|
| Sample | pvalue K27Ac (<A38Per Wilcox) | pvalue K36Me3 (<A38Per Wilcox) |
| A38Lg, Lung Metastasis | p = 0.0000007224 | p = 6.411e-09 |
| A13Pr1 | p < 2.2e-16 | p < 2.2e-16 |
| A13Pr2 | p = 0.0000001401 | p < 2.2e-16 |
| A13Lg | p < 2.2e-16 | p < 2.2e-16 |

Supplementary Data 3C: p-values for reprogramming of H3K9Me3 across LOCKs

| FIG. 10: H3K9Me3 Enrichment over LOCKs | | |
|---|---|---|
| Comparison | H3K9Me2 (Wilcox Test) | H3K9Me3 (Wilcox Test) |
| A38Per vs A38Lg | p < 2.2e-16 | p < 2.2e-16 |
| A13Pr1 vs A13Pr2 | p = 0.1086 | p < 2.2e-16 |
| A13Pr1 vs A13Lg | p = 0.2364 | p < 2.2e-16 |

Supplementary Data 3D: p-values for reprogramming of modifications from LOCK DE genes

Figures 11A, 11B:
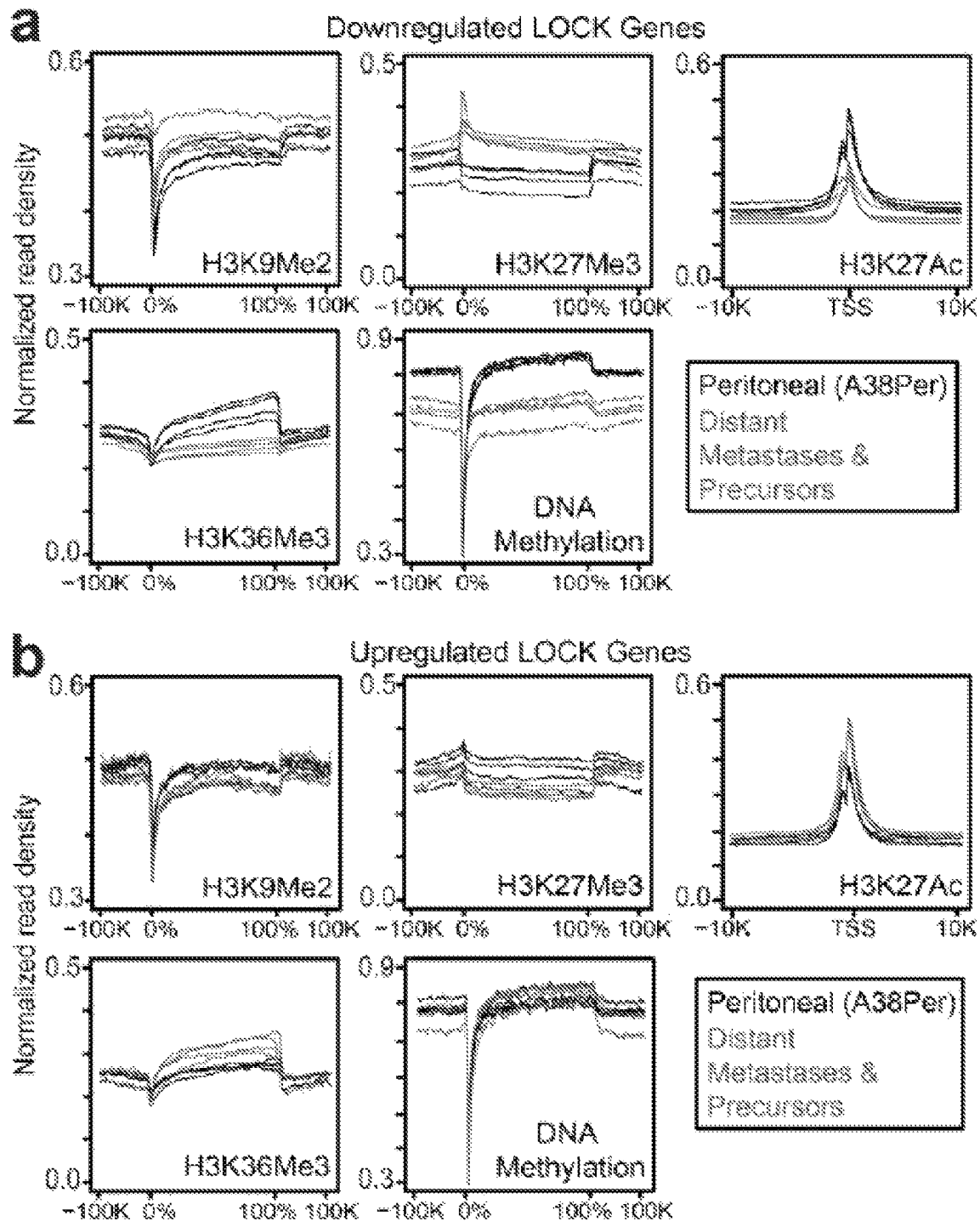
FIGS. 11A-11B relate to local reprogramming of DE gene loci within LOCKs.

| FIG. 11a: DE genes Downregulated from LOCKS (vs A38Per) | | | | | |
|---|---|---|---|---|---|
| Sample | K9Me2 (>A38Per Wilcox) | K27me3 (>A38Per Wilcox) | K27ac (<A38Per Wilcox) | K36me3 (<A38Per Wilcox) | DNA Methylation (<A38Per Wilcox) |
| A38Lg | p = 0.99 | p < 2.2e-16 | p < 2.2e-16 | p < 2.2e-16 | p < 2.2e-16 |
| A13Pr2 | p < 2.2e-16 | p < 2.2e-16 | p < 2.2e-16 | p < 2.2e-16 | p < 2.2e-16 |
| A13Pr1 | p < 2.2e-16 | p < 2.2e-16 | p < 2.2e-16 | p < 2.2e-16 | p < 2.2e-16 |
| A13Lg | p < 2.2e-16 | p < 2.2e-16 | p < 2.2e-16 | p < 2.2e-16 | p < 2.2e-16 |

| FIG. 11b: DE genes Upregulated from LOCKs (vs A38Per) | | | | | |
|---|---|---|---|---|---|
| Sample | K9Me2 (<A38Per Wilcox) | K27me3 (<A38Per Wilcox) | K27ac (>A38Per Wilcox) | K36me3 (>A38PerWilcox) | DNA Methylation (>A38Per Wilcox) |
| A38Lg | p = 0.99 | p < 2.2e-16 | p = 1.163e-06 | p = 0.000000007195 | p = 0.01699 |
| A13Pr2 | p < 2.2e-16 | p < 2.2e-16 | p < 2.2e-16 | p < 2.2e-16 | p = 3.312e-08 |
| A13Pr1 | p = 0.51 | p = 2.738e-06 | p = 1.362e-06 | p = 0.0004268 | p = 0.99 |
| A13Lg | p < 2.2e-16 | p < 2.2e-16 | p = 2.362e-13 | p < 2.2e-16 | p < 2.2e-16 |

Supplementary Data 3E: p-values for reprogramming across Large LOCK domains

| FIG. 13: Reprogramming Across Large LOCK Domains | | | |
|---|---|---|---|
| FIG. 13b | H3K9Me2 (>A38Lg Wilcox) | H3K9Me3 (<A38Lg Wilcox) | DNA Methylation (>A38Lg Wilcox) |
| A38Per Large LOCKs | p = 0.0006861 | p < 2.2e-16 | p = 0.000007037 |
| FIG. 13c | H3K9Me2 (>A38Per Wilcox) | H3K9Me3 (<A38Per Wilcox) | DNA Methylation (>A38Per Wilcox) |
| A38Lg Large LOCKs | p = 0.00002502 | p < 2.2e-16 | p = 3.52e-16 |

Supplementary Data 3F: p-values for 6AN RNA/ChIP-seq experiments

FIG. 19a: 6AN Down-regulation of DE Genes from LOCKS with Pre-Existing Regulatory Modifications (6AN vs. other LOCK genes)

|  | K27Ac (6AN > Other) | K36me3 (6AN > Other) | K27Me3 (6AN < Other) | K9Me2 (6AN < Other) |
|---|---|---|---|---|
| Wilcox Test p-value | p < 2.2e−16 | p < 2.2e−16 | p < 2.2e−16 | p = 0.02238 |

FIG. 19b: 6AN Increase of H3K9Me2 Across Reprogrammed LOCKs (DMSO vs 6AN Over LOCKs Reprogrammed between A38Lg vs A38Per)

|  | K9Me2 (6AN > DMSO) | K27Me3 (6AN > DMSO) |
|---|---|---|
| Wilcox Test p-value | p = 2.291e−07 | p = 0.6333 |

FIG. 19c, d: 6AN Decrease of H3K27Ac Over DE Genes Repressed From LOCKs

| FIG. 19c | K27Ac LOCK Down Genes (6AN < DMSO) | K27Ac Other LOCK Genes (6AN < DMSO) | K27Ac ECD Down Genes (6AN < DMSO) |
|---|---|---|---|
| Wilcox Test p-value | p = 0.01549 | p = 0.94462 | p = 0.8944 |

| FIG. 19d | K27Me3 LOCK Down Genes (6AN < DMSO) | K27Me3 Other LOCK Genes (6AN < DMSO) | K27Me3 ECD Down Genes (6AN < DMSO) |
|---|---|---|---|
| Wilcox Test p-value | p = 0.9417 | p = 0.5139 | p = 0.7957 |

Supplementary Data 3G: LOCK sensitivity analyses

Sensitivity Testing of LOCK Domain Calls

| Sample | Original Parameters | Test Parameter 1 | Overlap Analysis | Test Parameter 2 | Overlap Analysis |
|---|---|---|---|---|---|
| Small Peaks Removed | 5 kb | 2 kb | 5 Kb vs 2 Kb | 10 kb | 5 Kb vs 10 Kb |
|  | Called Domain Lengths | Called Domain Lengths | Percent Overlap | Called Domain Lengths | Percent Overlap |
| 38Per K9me2 | 1449305831 | 1475751351 | 98.02% | 1389543312 | 95.65% |
| 38Lg K9me2 | 979113009 | 1042797151 | 93.44% | 870263273 | 88.44% |
| 38Per K27me3 | 360026522 | 383258588 | 92.44% | 321712391 | 88.43% |
| 38Lg K27me3 | 882095148 | 886275657 | 99.53% | 863791604 | 97.89% |
| Minimal Merge Distance | 20 Kb | 15 Kb | 20 Kb vs 15 Kb | 25 Kb | 20 Kb vs 25 Kb |
| 38Per K9me2 | 1449305831 | 1387108909 | 95.42% | 1504614743 | 96.11% |
| 38Lg K9me2 | 979113009 | 887961919 | 89.91% | 1053584044 | 91.69% |
| 38Per K27me3 | 360026522 | 314837912 | 86.64% | 396029094 | 89.89% |
| 38Lg K27me3 | 882095148 | 848539120 | 96.00% | 906322630 | 97.16% |

Supplementary Data 4. This file lists all differentially expressed (DE) genes detected in each sample by RNA-seq, including level of expression, p-values, directional changes, and chromatin domains that each DE gene mapped to. Analysis of recurrent DE genes detected across distant metastatic samples and between control (DMSO) and 6AN treated cells is also reported.

Supplementary Data 4A: Summary of DE genes between A38Per and A13Pr1 detected by RNA-seq and mapped to chromatin domains (data not shown—publically available on the World Wide Web at nature.com/ng/journal/v49/n3/full/ng.3753.html?foxtrotcallback=true#supplementary-information by clicking link "Supplementary Table 7").

Supplementary Data 4B: Summary of DE genes between A38Per and A13Pr2 detected by RNA-seq and mapped to chromatin domains (data not shown—publically available on the World Wide Web at nature.com/ng/journal/v49/n3/full/ng0.3753.html?foxtrotcallback=true#supplementary-information by clicking link "Supplementary Table 7").

Supplementary Data 4C: Summary of DE genes between A38Per and A13Lg detected by RNA-seq and mapped to chromatin domains (data not shown—publically available on the World Wide Web at nature.com/ng/journal/v49/n3/full/ng0.3753.html?foxtrotcallback=true#supplementary-information by clicking link "Supplementary Table 7").

Supplementary Data 4D: Summary of DE genes between A38Per and A38Lg detected by RNA-seq and mapped to chromatin domains (data not shown—publically available on the World Wide Web at nature.com/ng/journal/v49/n3/full/ng0.3753.html?foxtrotcallback=true#supplementary-information by clicking link "Supplementary Table 7").

Supplementary Data 4E: Summary of DE genes between A38Per and A38Lv detected by RNA-seq (ChIP-seq not performed for chromatin domains) (data not shown—publically available on the World Wide Web at nature.com/ng/journal/v49/n3/full/ng0.3753.html?foxtrotcallback=true#supplementary-information by clicking link "Supplementary Table 7").

Supplementary Data 4F: Summary of DE genes recurrently up/down-regulated across primary tumor precursor (A13Pr1/2) and distant metastatic subclones (A13Lg, A38Lg, A38Lg) vs. A38Per (data not shown—publically available on the World Wide Web at nature.com/ng/journal/v49/n3/full/ng.3753.html?foxtrotcallback=true#supplementary-information by clicking link "Supplementary Table 7").

Supplementary Data 4G: Summary of DE genes between control (DMSO) and 6AN treated A38Lg cells detected by RNA-seq and mapped to chromatin domains (data not shown—publically available on the World Wide Web at nature.com/ng/journal/v49/n3/full/ng0.3753.html?foxtrotcallback=true#supplementary-information by clicking link "Supplementary Table 7").

Supplementary Data 4H: Comparison of overlaps between DE genes between matched lung and peritoneal subclones (A38Lg vs. A38Per) and DE genes between control and 6AN treated A38Lg cells.

| 38Lg up/ 6AN down | Genes | 38Lg down/ 6AN up | Genes | 38Lg up/ 6AN up | Genes | 38Lg down/ 6AN down | Genes |
|---|---|---|---|---|---|---|---|
| Coregulated/ 6AN down: 1032/1968 (52%) | GDF5OS | Coregulated/ 6AN up: 915/2192 (42%) | CCT6B | Coregulated/ 6AN up: 379/2192 (17%) | WDR25 | Coregulated/ 6AN down 277/1968 (14%) | RP11-400K9.4.1 |
| Coregulated/ 38Lg up: 1032/4368 (24%) | EDN2 | Coregulated/ 38Lg down: 915/4402 (21%) | JAK2 | Coregulated/ 38Lg up 379/4368 (0.09%) | TOMM7 | Coregulated/ 38Lg down 277/4402 (0.06%) | C14orf105 |
|  | C1QTNF2 |  | TMEM63A |  | IGFBP1 |  | CCK |
|  | CLDN2 |  | FAM101A |  | SLC9A3R2 |  | RP11-255B23.3.1 |
| (Coregulated: genes present in both 38Lg and matched 6AN datasets) | FAT2 |  | KRCC1 |  | C7orf60 |  | CFTR |
|  | RBM24 |  | ERRFI1 |  | ZFYVE28 |  | CD22 |
|  | KMO |  | LRRC6 |  | CTSD |  | RGS7 |
|  | TPRG1-AS1 |  | TNFAIP2 |  | GATA6 |  | ERVMER34-1 |
|  | DOCK2 |  | MAST3 |  | RP11-480A16.1.1 |  | CCNI2 |
|  | FAM101B |  | ABCC10 |  | GXYLT2 |  | ADAMTS14 |
|  | KRT7 |  | RP11-65J3.1.1 |  | AC002472.8.1 |  | ANO1 |
|  | TCF7 |  | SLC12A7 |  | C3orf23 |  | PADI3 |
|  | RP11-845M18.3.1 |  | WASH7P |  | TMEM43 |  | CHST4 |
|  | C4orf49 |  | ANKRD13D |  | FUT11 |  | FER1L6 |
|  | SLC1A3 |  | ZBTB7A |  | IFFO1 |  | TNNT2 |
|  | DMC1 |  | WASH6P |  | SLC1A4 |  | RP11-597D13.9.1 |
|  | TMSB15A |  | IL32 |  | DDT |  | RP11-6F2.4.1 |
|  | LHX4 |  | RNF217 |  | IDI1 |  | MYO5B |
|  | KIAA1324 |  | EFNB1 |  | SARM1 |  | KRT23 |
|  | ITPRIPL1 |  | KHNYN |  | HOTAIR |  | MUC4 |
|  | PPAPDC1A |  | TMEM59 |  | TSC22D1 |  | RP11-346D6.6.1 |
|  | RGS5 |  | GAS8 |  | NBAS |  | ITGAM |
|  | RP11-618G20.2.1 |  | ABC7-42389800N19.1.1 |  | ENG |  | PTPRZ1 |
|  | RIPPLY1 |  | RASSF7 |  | SSTR5 |  | GPR116 |
|  | UHRF1 |  | MRPS6 |  | CRIP2 |  | CYP24A1 |
|  | SUSD5 |  | RP11-353B9.1.1 |  | NUDT18 |  | DHRS9 |
|  | KRT80 |  | GRAMD4 |  | RPL31 |  | GRPR |
|  | KRT32 |  | SERINC5 |  | KIAA1143 |  | AIF1L |
|  | SLC26A7 |  | TMEM102 |  | DNAJC3-AS1 |  | CGN |
|  | TFPI2 |  | TMPRSS5 |  | C1R |  | RP11-314P12.3.1 |
|  | RP11-314P12.2.1 |  | TMEM63B |  | GAB2 |  | CYFIP2 |
|  | MMP7 |  | FAM109A |  | FAM174B |  | ATP6V0A4 |
|  | KLHL23 |  | TLR4 |  | SYT11 |  | MPP7 |
|  | C1orf110 |  | C20orf96 |  | DET1 |  | KREMEN1 |
|  | GRIN2A |  | SMAD6 |  | TBC1D8B |  | TTN |

| | | | |
|---|---|---|---|
| PADI2 | VAMP4 | TAZ | LEF1 |
| AL162759.1.1 | MYO1E | UCP2 | SP140 |
| MYBL2 | DVL1 | RP4-647C14.2.1 | SP6 |
| GLYATL2 | AC069513.3.1 | AARS | ANXA10 |
| RRM2 | ITPKC | DALRD3 | NYAP2 |
| E2F2 | USP18 | SEMA3C | MCOLN3 |
| CPA4 | RAB33B | ATP2B1 | DENND2A |
| HHIP | RP11-325F22.3.1 | THTPA | HSH2D |
| MYPN | ADHFE1 | GPER | C1orf106 |
| RP11-150O12.6.1 | LENG8 | ITPK1 | EVL |
| CLSPN | RILPL2 | IL1RAP | C7orf58 |
| WDR69 | TSNARE1 | RPL29 | RP1-95L4.4.1 |
| RP11-150O12.1.1 | SPIRE2 | EFHC1 | IL11 |
| AKAP12 | MMAA | CRTAP | DDN |
| DOCK10 | SLC15A3 | B3GAT1 | snoU13 |
| PSG5 | PLEKHM1 | SEL1L | SLC27A2 |
| SPC25 | RP11-403I13.8.1 | ME1 | DGAT2 |
| TM4SF4 | STARD10 | TBC1D9B | SHANK2 |
| FAM71D | SNPH | EEF1A1P5 | HNRPCP |
| OLFML2A | EME2 | VKORC1 | AC005083.1.1 |
| OXCT1 | DHRS3 | SNX21 | S1PR3 |
| FAM111B | MX1 | KDELC1 | ARL14 |
| snoU13 | RRN3P1 | AIP | SAMD5 |
| AC073130.1.1 | FAM100A | RP1-34B21.6.1 | ARHGDIB |
| CCNE2 | DDO | OSBPL6 | GNG4 |
| CDC25A | TPRN | C4orf34 | CDC42BPG |
| RP3-324O17.4.1 | CD58 | FAM18B2 | SMO |
| MCM10 | PLCG2 | TXNDC15 | TIAM1 |
| RP11-424C20.2.1 | RP11-220I1.1.1 | LIN7A | NMU |
| MSRB3 | ZNF554 | CTD-2287O16.1.1 | SOX6 |
| HEATR7B1 | GLI4 | FLYWCH1 | PPFIBP2 |
| TP73 | TRAF1 | C11orf2 | LY6D |
| PRKDC | ANKRA2 | CHST12 | PLAC1 |
| DLEU2 | SYNGR2 | FTX | SYTL5 |
| CTB-164N12.1.1 | FAM113B | CCNO | SELL |
| SDPR | CROCC | AL844908.5.1 | MYO5C |
| POLE2 | HIVEP2 | RP11-996F15.2.1 | UNC5A |
| MEST | RHBDD2 | CPEB2 | SPNS2 |
| ASTN2 | GATS.1 | PDIA6 | BIK |
| LAMP5 | RALGPS1 | STON1 | PPYR1 |
| MKI67 | VWA1 | ARRDC3 | FAM46B |
| TMEFF2 | HEATR7A | C7orf23 | COL17A1 |
| CPA5 | HLA-K | TESK1 | MACC1 |
| ANKRD18DP | MAF1 | HEG1 | DNAH12 |
| ESCO2 | TMEM8A | RP11-85K15.2.1 | CYP2J2 |
| TUBA1B | DDX58 | MTHFD2 | LDLRAD3 |
| WNT7A | PYROXD1 | RWDD2A | RAB6B |
| MCM4 | CYP27C1 | RPL10 | BTBD11 |
| AKAP5 | RNF145 | PHACTR1 | PLA2G7 |
| TYMS | ZDHHC14 | NUDT22 | TBC1D30 |
| CDCA2 | KLF7 | TRIM4 | SNX25P1 |
| CAP2 | KYNU | RHOG | TESC |
| RP11-527N22.2.1 | LDLR | EIF1B | COL1A1 |
| RP11-297M9.2.1 | ZDHHC11B | SSR4 | FERMT1 |
| DEPDC1B | AC007383.3.1 | ARG2 | MED12L |
| DPF1 | SRCRB4D | TCEAL1 | RP11-582J16.5.1 |
| RP11-554I8.2.1 | LRP5L | ZFPL1 | BRI3BP |
| RP11-33N16.1.1 | FOXC1 | RGS10 | LAD1 |

-continued

| | | | |
|---|---|---|---|
| MAP3K14 | AACS | MEIS3 | C16orf74 |
| EXO1 | SLC44A2 | LLGL1 | CD163L1 |
| RP11-253E3.3.1 | SEPP1 | C9orf37 | ANXA8L1 |
| FABP6 | ARHGAP25 | USE1 | AEN |
| RP11-184I16.2.1 | STAT6 | YPEL1 | C8orf46 |
| FOSL1 | RP11-27I1.2.1 | PLA2G15 | CDH1 |
| CCDC99 | VPS28 | RPS27 | XDH |
| AC016831.7.1 | R3HDM2 | VEGFB | XK |
| FJX1 | C11orf35 | CELSR3 | ANXA8L2 |
| SCN5A | ARHGEF10L | EPHX1 | COL12A1 |
| RP11-687M24.3.1 | PSMD9 | TINF2 | PPARGC1B |
| ILDR2 | METTL7A | ZNF70 | C6orf132 |
| MUC5AC | TMTC2 | C3orf18 | TTC3P1 |
| AC092614.2.1 | NFE2L1 | PITPNC1 | GALNT6 |
| APOBEC3B | C5orf13 | ISL1 | SEMA7A |
| RP11-54A9.1.1 | ZNF768 | CORO6 | F2RL1 |
| NCAPG | SIK1 | NEK3 | ALDH1A1 |
| ATAD2 | OSCP1 | RP11-313D6.4.1 | CRABP2 |
| SMC4 | ACADS | RPL27A | CA2 |
| FUT9 | HERC6 | RP11-216F19.1.1 | FGFBP1 |
| ZNF488 | CLDN9 | ABCA3 | SNAI2 |
| TK1 | RHEBL1 | PITPNM2 | PLS1 |
| CTD-2023N9.1.1 | CHST6 | LGR5 | KLHL13 |
| HELLS | VMAC | AGA | RP5-862P8.2.1 |
| MMP24 | AQP3 | FAM113A | RAB38 |
| SLITRK3 | DNAL4 | GPR37 | SLC7A8 |
| ELOVL2 | HBP1 | VASH1 | WNT3 |
| SERINC2 | ZG16B | CAMKK1 | SARDH |
| AC002066.1.1 | FAM100B | MAST1 | TPM1 |
| DIAPH3 | EREG | RP11-574K11.20.1 | RASEF |
| RP11-291L15.2.1 | ZNF862 | RPL12 | SKAP1 |
| GINS1 | NARFL | NSUN5P2 | TRIM14 |
| RP5-968P14.2.1 | SWSAP1 | RP11-477I4.3.1 | CTSL2 |
| DHFR | YPEL5 | NSUN5P1 | GK |
| ROR1 | SLFN5 | HAUS4 | VEPH1 |
| MCM3 | CCNDBP1 | TMEM234 | RP11-800A3.4.1 |
| RP1-140K8.5.1 | PAQR8 | MRC2 | FGFR3 |
| GLYATL1 | SLC25A27 | PYCR1 | PADI1 |
| CDCA7 | GOLGA8B | SLC26A6 | CDS1 |
| CSMD2 | IKZF2 | C3orf78 | JPH1 |
| RBPMS2 | HSD17B11 | CD68 | FAM81A |
| RBL1 | LMBR1L | AP003068.23.1 | GALNT12 |
| RP11-677M14.3.1 | KCNJ14 | PAK3 | DPY19L2 |
| CCBE1 | DDR1 | GMPPA | ITGBL1 |
| CCND1 | C7orf53 | EEF1A1P6 | SYNPO2 |
| E2F8 | RELB | AC093673.5.1 | RP11-157P1.4.1 |
| CDC45 | WASH3P | CBS | ANKRD22 |
| LMNB1 | PDCD4 | MIF4GD | GRHL1 |
| C11orf41 | NR1D1 | CNPY4 | KRT15 |
| BEST3 | NCOA7 | GGT7 | RP11-93L9.1.1 |
| CTPS | GOLGA2 | LRP1B | C15orf62 |
| RASSF10 | CEBPG | FAIM2 | AADAC |
| POLA1 | C2orf15 | ZNF333 | AC112229.1.1 |
| TUBB6 | KLF13 | AGXT2L2 | TRIM59 |
| HOMER1 | GEMIN8 | B9D1 | DNAH10 |
| CD200 | ARRDC2 | EEF1A1 | CTD-2021J15.2.1 |
| CENPM | SLC39A11 | ATRNL1 | KRT19 |
| ERCC6L | SAT2 | PAOX | KIAA1199 |
| HMMR | ZER1 | CTSA | GPM6A |
| CENPW | KIAA1407 | SLC45A1 | AKAP6 |

| | | | |
|---|---|---|---|
| RP11-298I3.4.1 | OAS1 | RAB3IL1 | GPR110 |
| RP11-259P6.1.1 | AC004410.1 | C6orf1 | QPCT |
| THBS1 | DGAT1 | CTD-2314G24.2.1 | RP11-382A18.1.1 |
| GPR63 | RNF103 | CYP4X1 | METTL7B |
| DTL | EFHC2 | HCFC1R1 | PHACTR2 |
| RP11-101K10.8.1 | C17orf69 | FAM70B | PLEKHA7 |
| RP11-204J18.3.1 | LINC00493 | SHMT2 | PLAU |
| WDR4 | ST6GALNAC2 | SEC14L5 | SLC4A3 |
| BRIP1 | KLHL31 | CLK4 | KRT18 |
| LMNB2 | LGMN | UGDH-AS1 | C3orf52 |
| C14orf49 | LLGL2 | ITGA11 | SYTL2 |
| EIF6 | ENDOV | CGREF1 | PKDCC |
| ARHGEF26 | CST1 | RPL22L1 | ASB9 |
| ETNK2 | RP13-516M14.1.1 | FKBP2 | SLC22A20 |
| POLQ | LIPA | OXA1L | IGSF3 |
| RP11-573I11.2.1 | FAM13A | C10orf102 | CLDN10 |
| APLN | ST3GAL1 | DNASE1L1 | MBOAT1 |
| RP11-304F15.3.1 | APOBEC3G | HIGD2A | TMEM169 |
| NDC80 | PLAUR | MLLT3 | SYK |
| MCM6 | ACYP2 | AP001496.1 | MAST4 |
| CAV1 | RTN2 | FAM156B | SDC1 |
| RP11-53M11.3.1 | HIF1A | TRPT1 | RP11-613M10.6.1 |
| MARK1 | DNASE2 | RP11-571M6.6.1 | PPM1H |
| CTA-445C9.15.1 | CA11 | RP11-243J18.3.1 | GCHFR |
| USP13 | SLC7A7 | SGSH | RHOD |
| RP5-1172A22.1.1 | ABCA10 | CTD-3074O7.5.1 | EZR |
| UCN2 | PTK6 | CNTNAP1 | RP11-303E16.2.1 |
| MCAM | RPS6KA2 | TNFRSF10C | RCC2 |
| ZWINT | WHAMMP3 | B3GNT1 | KDR |
| LINC00460 | ENGASE | LRP1 | RP11-416I2.1.1 |
| BIRC5 | LPCAT4 | P2RX6 | GPR65 |
| FLNC | EPS8L3 | SSBP2 | BCL7A |
| SYNE2 | TMEM198B | ZC3H6 | PPCDC |
| HMGN2 | PRICKLE3 | CCNG1 | NBPF10 |
| ADCY3 | PDE4DIP | TBC1D4 | AC108463.1 |
| PDSS1 | GPR108 | MAGED2 | CADM4 |
| CDCA3 | TMC4 | DNAJC1 | SPTBN5 |
| AXL | PTP4A3 | PCK2 | CUEDC1 |
| KIAA0101 | ITGAX | MANF | CMTM4 |
| NAV3 | TSSC4 | ZCWPW2 | CDK5R1 |
| KIF11 | ANO9 | C1orf213 | C19orf21 |
| LPCAT2 | PPP1R3B | CACNG6 | C1orf116 |
| KIF4A | ANTXR2 | AC004540.5.1 | UNC5C |
| CTD-2334D19.1.1 | ARHGEF3 | TSLP | ALDH5A1 |
| EML5 | C10orf32 | RP5-1103G7.4.1 | MB21D2 |
| NME1 | PGM2L1 | C1S | RP11-7K24.3.1 |
| ARHGAP11A | HLA-H | SPATA25 | DSG2 |
| MCM2 | TUBG2 | PPAP2A | PLD6 |
| SLC5A11 | SLC16A3 | RP11-390P2.4.1 | GALNT5 |
| CHN1 | CCNL2 | RP11-539L10.3.1 | ZNF185 |
| KIF23 | SGK1 | SH2B2 | P2RY2 |
| ARHGAP19 | MEF2C | NEURL2 | PLCXD1 |
| SLC8A1 | CAMTA2 | KLHDC2 | AIG1 |
| FBN2 | HLA-F-AS1 | SHISA2 | PALM |
| FKBP5 | PIWIL4 | PXK | PKP4 |
| IGSF9B | LSS | WBSCR27 | ZNF462 |
| KIF15 | PCMTD2 | DSEL | SAA1 |
| NUP210 | CFI | TRIM46 | SPATA13 |
| AS3MT | ARL4D | CTSF | LAMA3 |
| TNFAIP8L3 | MVK | KLHL35 | NID1 |

| | | | |
|---|---|---|---|
| PM20D2 | CDH17 | PDIA5 | PEAR1 |
| OPN3 | MAFF | PLK3 | PYGL |
| RRM1 | CACNB1 | ZNF815 | USP40 |
| DNA2 | C2orf63 | NICN1 | DIS3L |
| DEPDC1 | IL15 | SCAND1 | ID2 |
| PDE1A | ST3GAL6 | CALHM3 | FUT1 |
| ALYREF | C9orf7 | RP5-827C21.4.1 | PRSS3 |
| MORC4 | ENDOU | LETMD1 | NMNAT2 |
| FBXO5 | PIM3 | JAKMIP3 | DNAJA4 |
| DPY19L2P1 | CLDN7 | LZTFL1 | DOCK9 |
| CENPF | DAB2IP | CTNS | DDI2 |
| GPR19 | TARSL2 | RP11-280F2.2.1 | PLAC8 |
| SYCE2 | REC8 | PDK1 | FBP1 |
| GINS4 | FAM160A2 | MBL1P | RAG1 |
| XRCC2 | ZFP36 | LHPP | PRPF4 |
| DARS2 | RP11-73K9.2.1 | BLVRB | RPS6KA1 |
| HMGB3 | STARD4 | CALHM2 | DSP |
| KIAA1524 | SGK2 | RP11-277P12.20.1 | SLC22A5 |
| NUP188 | CIR1 | PTCHD2 | AADAT |
| DPF3 | MAPK8IP3 | UST | FARP2 |
| STMN1 | USP20 | IRF2BPL | MCC |
| WDHD1 | RP11-149I23.3.1 | PLK1S1 | ZNF658 |
| NCAPD3 | RP11-108M9.4.1 | TTC39B | B3GNT5 |
| CCNE1 | HIP1R | ABHD14B | NT5DC3 |
| TRPV2 | CYP4F3 | DLG4 | ABCC9 |
| CDKN3 | SH3YL1 | PCDHGA7 | PNPLA4 |
| PRR11 | TNFSF12 | MAGED1 | ZNF717 |
| CSRP2 | TMEM8B | LEPREL2 | RAVER2 |
| COTL1 | IGSF8 | LOXL2 | MREG |
| MSH2 | PTK2B | SLC43A2 | RBP1 |
| KIF18B | NR4A2 | ZEB1-AS1 | RAPGEF3 |
| SKP2 | SPIRE1 | LENG8-AS1 | CNKSR3 |
| ADORA2B | DLL1 | C17orf72 | RP11-757F18.5.1 |
| GFRA3 | TMED1 | C16orf93 | PRSS12 |
| ZNF724P | SQLE | ARHGAP4 | HOOK1 |
| RASGRF1 | ABCC6 | CNTD1 | COL16A1 |
| FAM83D | VSIG10L | PCDHGA3 | MST4.1 |
| BUB1 | FA2H | STK32A | CMIP |
| MTHFD1 | OSBPL7 | SLC29A4 | SMC5 |
| DHX9 | KCNIP3 | LEPRE1 | ANXA2P2 |
| NRG1 | LYNX1 | HOMER3 | STEAP2 |
| PCNA | ULK3 | MCEE | NUDT14 |
| UTP20 | HINT3 | XBP1 | MMD |
| MIR17HG | FDFT1 | ALDH1L2 | ANKRD56 |
| ANLN | TRIB1 | MAP2 | SURF2 |
| RUVBL1 | NPDC1 | NNMT | SH2D3A |
| MYO1B | VEGFC | NUCB1 | MAP3K1 |
| NCAPG2 | GPRC5C | KLRC2 | UACA |
| FH | SIGIRR | TMEM158 | TAF2 |
| GNG11 | TCEANC | SEPT7L | DCBLD2 |
| GS1-465N13.1.1 | MKNK2 | RP11-161M6.4.1 | RP11-295M3.1.1 |
| MT1L | N4BP2L1 | AC079922.3.1 | NAALADL2 |
| TNS1 | KCNMB4 | PCDHB7 | CNTRL |
| BARD1 | RP5-1182A14.3.1 | HSD17B7P2 | CD82 |
| THOP1 | GET4 | NAT6 | FBXL19-AS1 |
| SKA1 | FKBP10 | PTX3 | RHBDL2 |
| C1QL1 | RDH10 | ZNF836 | RP11-448G15.3.1 |
| C11orf82 | SLC22A15 | TMEM106A | RP11-357H14.19.1 |
| CCNA2 | CCDC57 | TFF2 | TUBGCP5 |
| SLC35F3 | SHB | CYP1A1 | INADL |
| C10orf140 | TMPRSS3 | PPP1R3E | C9orf64 |
| NEXN | NYNRIN | TMEM120A | ARAP2 |
| ASF1B | TNFRSF9 | POLN | KRT16 |
| PRTFDC1 | SESN3 | RAPGEF4 | ALS2CL |
| FAT3 | A2LD1 | RABAC1 | |
| H2AFX | RP11-475N22.4.1 | CACNA1G | |

-continued

| | | |
|---|---|---|
| PRIM1 | ZNF628 | LOX |
| SNX18P3 | JAG2 | FAM151B |
| RP11-973F15.1.1 | RP11-244H3.1.1 | PTPRM |
| ADRB2 | GOLGA8A | CLEC2B |
| FBXL13 | TP53INP2 | KDELR3 |
| CDC20 | WASH4P | ISYNA1 |
| CENPK | TNIP1 | RASL11A |
| CDCA4 | RP4-659J6.2.1 | CALR |
| ATAD5 | CCDC126 | RP11-108K14.4.1 |
| SMC1A | PTPRB | METTL12 |
| FAM196B | U6 | BNIP3 |
| UGT1A1 | SPRY3 | FAM175A |
| CTD-2574D22.2.1 | MMP15 | CRLF2 |
| MCM5 | SLC23A3 | TMEM231 |
| MELK | TBC1D3F | CRELD2 |
| LYPD1 | ABCA5 | PLXNA3 |
| DLGAP5 | RP4-798A10.2.1 | AC026202.3.1 |
| NUSAP1 | CLDN15 | ASNS |
| TUBBP1 | TMC7 | RASIP1 |
| MYH10 | TCTEX1D2 | SFRP5 |
| MIR155HG | NOS3 | RP11-66N24.3.1 |
| CCDC138 | ARHGEF16 | ABCC3 |
| ERCC2 | TPBG | RIBC1 |
| KIF20A | FAAH | HSP90B1 |
| TMEM14B | TMEM150A | HYOU1 |
| H2AFY2 | LRRC56 | BAMBI |
| OXTR | CEP85L | TPP1 |
| RDM1 | MIA | ZCCHC24 |
| PLEK2 | CDH6 | FAM161B |
| SHCBP1 | PON3 | AC004080.12.1 |
| GJC1 | CCDC92 | MAPT |
| SNRNP25 | PTPRH | AC018755.11.1 |
| KCNQ5 | FOXQ1 | PLOD2 |
| ODC1 | J01415.23 | MAN1A1 |
| EBNA1BP2 | PPFIA3 | NUCB2 |
| FABP3 | SMPDL3A | DERL3 |
| MCM7 | AC007283.5.1 | SCN1B |
| CHAC2 | ALPPL2 | FN1 |
| BORA | MTHFR | PLCD1 |
| ASRGL1 | WASH2P | CCDC85B |
| VIPR1 | RSAD2 | BTBD19 |
| PTTG1 | LIMA1 | AP000769.1 |
| ACTB | PPP1R16A | AC147651.3.1 |
| TOP2A | PIK3C2B | ATHL1 |
| NEIL3 | XAF1 | CYP2E1 |
| ALDH1B1 | KIAA0513 | FAM182B |
| CEP250 | GRAMD1C | PDIA4 |
| FAM131B | GLDN | ZFP2 |
| FAH | GPCPD1 | SLC25A29 |
| CIT | CABP4 | RAB24 |
| CDCA8 | NXNL2 | RP11-755F10.1.1 |
| CDK2 | SEMA4C | QPCTL |
| EZH2 | PHYHIP | ALDOC |
| PSMC3 | AC093734.11.1 | AKR1C1 |
| FGGY | IRF9 | LRRC29 |
| NXPH4 | ZNF517 | RP11-307O13.1.1 |
| FRMD4A | RP5-1187M17.10.1 | SEMA3F |
| CSPG4 | HIST1H1C | RUSC1-AS1 |
| CSE1L | ANKRD42 | EVI2B |
| KIF20B | ZC3H12A | TIE1 |
| C2CD3 | JUND | HSPA5 |
| PPIAP29 | SEMA4B | TSPYL2 |
| CTA-221G9.10.1 | CTAGE5 | HERPUD1 |
| TPX2 | NLRP1 | AQP2 |
| DKK1 | GNE | RP4-794H19.2.1 |
| PFAS | LTB4R2 | C2orf16 |
| PBK | BBS12 | AKR1C2 |
| TRIP13 | DICER1-AS | ANGPTL4 |

-continued

| | | |
|---|---|---|
| CCDC18 | CMPK2 | HCN2 |
| UBE2T | CALB2 | NOG |
| AL357673.1 | DHRS2 | AKR1B1 |
| PDE12 | LRFN3 | ST7-AS1 |
| NUP155 | PROC | EVI2A |
| ARNTL2 | PROS1 | AC022007.5.1 |
| POLD2 | TMEM80 | ZNF575 |
| NCAPD2 | RALGDS | RCN3 |
| VCL | SLC6A8 | PCDHB15 |
| CCDC85C | TMC6 | RP13-895J2.7.1 |
| FANCD2 | HMGCR | C9orf150 |
| RP11-117P22.1.1 | TBC1D17 | ANGPT1 |
| MYLK | TBC1D3 | ARSA |
| RP11-394B2.4.1 | GRN | RP11-49I11.1.1 |
| PRLR | ROM1 | PRPH |
| AP2B1 | MID1IP1 | AC004383.5.1 |
| RASSF2 | C15orf61 | P4HA1 |
| PRKAG2 | SPATA20 | ANGPTL2 |
| COL4A6 | FAM78A | AC002480.4.1 |
| PSMC3IP | STAT2 | MTMR9LP |
| ARRB2 | PYGM | CRELD1 |
| CAMK4 | RHBDF1 | UPB1 |
| TSPAN2 | LRCH4 | AC002480.3.1 |
| RFC2 | PODN | RP11-554A11.9.1 |
| PLK2 | SPRY4 | GALNT9 |
| SRRT | CITED4 | AL137145.2 |
| WNT7B | LIPG | VLDLR |
| ADORA1 | CAPS | IFITM10 |
| C22orf29 | EIF1 | LDHD |
| HTR1B | CYP4F12 | ERO1LB |
| ITGB8 | AKAP17A | NTNG2 |
| ZNF660 | ACTR1B | NPY1R |
| EPB41L2 | WDR66 | |
| COQ3 | AP001468.1 | |
| AASS | AP001372.2.1 | |
| PAICS | FAM214A | |
| CENPI | GSN | |
| CASC5 | FAM193B | |
| TUBA1C | TPRG1L | |
| NUDCD1 | ARHGEF2 | |
| L2HGDH | TNFAIP3 | |
| CHML | CDA | |
| CCNB1 | PLA2R1 | |
| RP11-799O21.1.1 | ZSWIM4 | |
| DNMT1 | IRAK2 | |
| CDK1 | LYZ | |
| RP11-673C5.1.1 | TJP3 | |
| NUP37 | C8orf55 | |
| TPMT | CTB-131B5.5.1 | |
| AURKA | AC103810.1 | |
| PEA15 | PCDHGB2 | |
| NRGN | KLC4 | |
| PLK1 | RP4-541C22.5.1 | |
| ZNF124 | SIX5 | |
| CGNL1 | SEL1L3 | |
| SNRPD1 | MIR29C | |
| PTPN14 | MZF1 | |
| CDC7 | ADAM8 | |
| DERA | WDR45 | |
| PYGO1 | ZNFX1-AS1 | |
| LRRCC1 | AC017099.3.1 | |
| FAM173B | ARSD | |
| AHCY | DLX4 | |
| UBAC2-AS1 | HK2 | |
| HIGD1A | HS3ST1 | |
| GMNN | ABCG1 | |
| NCAPH | CCDC146 | |
| CEP128 | EGLN3 | |
| SLC38A5 | CLK1 | |
| TUBB4B | UPK3B | |

-continued

| | |
|---|---|
| RP11-512F24.1.1 | SLC16A6 |
| BICC1 | HLA-F |
| HMGB1P5 | NT5M |
| NUF2 | BTG1 |
| VCAN | C7orf63 |
| FAM64A | RASSF9 |
| DNAJC9 | CTSL1 |
| RANBP1 | ENDOD1 |
| C4BPB | FAM116B |
| C9orf140 | KNDC1 |
| SKA2 | PPP1R3F |
| RP11-181C3.2.1 | LARP6 |
| PKMYT1 | FBXO6 |
| RFWD3 | CCDC69 |
| TCOF1 | PRRT1 |
| KNTC1 | CTD-2258A20.4.1 |
| DKC1 | TSPAN1 |
| MPP2 | RP11-362F19.1.1 |
| CCNF | SLC2A10 |
| C1orf112 | CTD-2341M24.1.1 |
| AC046143.7.1 | C2orf81 |
| STMN3 | FZD4 |
| OIP5 | RAB40C |
| DGKH | EXD3 |
| NRM | IFIT3 |
| RFC3 | PCDHGC5 |
| RBBP8 | RP11-285F7.2.1 |
| HTR7P1 | RHBDF2 |
| NMT2 | PRICKLE4 |
| ARHGAP11B | RABL2A |
| DPYSL3 | WBP1 |
| TCAM1.1 | LAMB3 |
| YBX1 | RP4-697K14.7.1 |
| HSP90AA1 | TMEM91 |
| ACTA2 | PCDHAC1 |
| MPP5 | TRIM2 |
| C8orf84 | C16orf7 |
| ASPM | RTP4 |
| LRRC8C | KIAA1875 |
| TBC1D7 | RP11-540D14.6.1 |
| RP11-462L8.1.1 | JUP |
| ZNF367 | NEU1 |
| RP11-956J14.1.1 | DDX60 |
| CCT5 | HOOK2 |
| C6orf52 | BCO2 |
| NEK6 | TBC1D8 |
| TSPY26P | PRRX1 |
| MRPL1 | KRTCAP3 |
| FARSB | PINK1 |
| PKP2 | NFIL3 |
| CAND2 | LCN2 |
| MRTO4 | TYMP |
| KIAA0586 | RP11-429J17.2.1 |
| DEK | WARS |
| FAM54A | COL6A1 |
| FEN1 | LZTS2 |
| RP3-510D11.2.1 | NPIPL2 |
| SMC2 | LCA5L |
| RELT | KB-1460A1.5.1 |
| SGOL1 | CYP4V2 |
| ANKRD1 | FAM59A |
| SUV39H2 | SEZ6L2 |
| KDELC2 | PTPRE |
| HMGB2 | NR2F6 |
| ATRIP | COL11A2 |

-continued

| | |
|---|---|
| SACS | RENBP |
| DEPDC7 | AQP6 |
| HMGB1 | ULBP1 |
| RP11-380J14.1.1 | CX3CL1 |
| POP1 | CCDC149 |
| GFAP | ASAH1 |
| NUP205 | TNFRSF14 |
| CENPA | C12orf63 |
| TPGS2 | C12orf57 |
| CD109 | PSPN |
| WDR3 | RP11-263K19.6.1 |
| NOP56 | MAPRE3 |
| PTRF | RP11-44N21.1.1 |
| PHIP | TNFSF13B |
| QSER1 | FMO5 |
| FAM86A | PRX |
| POC1A | GSDMB |
| CYB5RL | JUNB |
| H2AFZ | HMGCS1 |
| AC092329.1 | CSF2RA |
| RAD51AP1 | HEXDC |
| CCP110 | PLXND1 |
| CEP55 | NFAM1 |
| ZNF347 | PER1 |
| NCS1 | CALCOCO1 |
| RAD54L | DRAM1 |
| MDM2 | AOC2 |
| SMTN | GAS7 |
| CDC25C | IFIT2 |
| TFDP1 | MTRNR2L9 |
| NEURL1B | TSTD1 |
| TBCD | NR4A1 |
| KRBOX1 | TM6SF1 |
| SAE1 | CBLB |
| CHEK1 | CCDC24 |
| RP11-678B3.2.1 | FAM66C |
| REV3L | C9orf16 |
| SPC24 | KDM6B |
| TMPO | TBX6 |
| DHRS4L2 | MMP28 |
| MYOF | ACSL1 |
| TUBA4A | G0S2 |
| ADAT2 | CDC42EP2 |
| RP11-348A11.4.1 | SCD |
| BST1 | NFKBIA |
| FOXM1 | PLEKHF1 |
| AC027612.6.1 | AGFG2 |
| RP11-1334A24.4.1 | LEPREL4 |
| UBE2N | ULK1 |
| PRIM2 | ADAMTS13 |
| S100A2 | CAMK2N1 |
| NEGR1 | PDE7B |
| HNRNPAB | AC073343.1 |
| CCDC41 | AC002117.1.1 |
| CAMK1 | SPSB3 |
| GTSE1 | SLC5A12 |
| MMP2 | PLA2G6 |
| BOLA3 | HOXD4 |
| SYT15 | HS3ST3B1 |
| BCL2 | JAK3 |
| ECHDC3 | C10orf10 |
| KIFC1 | NFKBIZ |
| G3BP1 | DUSP8 |
| PFN1 | NEIL1 |
| RAET1K | ECEL1P2 |
| MNS1 | RP11-783K16.13.1 |
| SIRPA | KLHDC1 |
| RP11-152N13.12.1 | MST1 |
| PORCN | ROBO4 |
| NOC3L | SYT17 |
| RAD18 | NR1H3 |

-continued

| | |
|---|---|
| ESPL1 | GDPD3 |
| PTER | CEBPB |
| RP11-1277A3.2.1 | SDCBP2 |
| NUP107 | NOV |
| SGOL2 | DNAH7 |
| DIO2 | IER5L |
| ZNF726 | FANK1 |
| SFXN2 | ORAI3 |
| FRMD6 | SLC5A3 |
| CENPN | B3GALT4 |
| NT5DC2 | ZDHHC1 |
| RFC4 | KIF27 |
| NOP16 | GIMAP2 |
| TUBG1 | CDC42EP5 |
| DZIP1 | AC006028.9.1 |
| IPO5 | PRSS16 |
| LHFP | TGFBR3 |
| ARHGAP22 | FASN |
| TMEM48 | ATP1B1 |
| RPA3 | C17orf108 |
| TMCO7 | EPHB6 |
| THSD1 | BCL6 |
| AC013461.1.1 | RP4-811H24.6.1 |
| CCDC165 | RP11-496I9.1.1 |
| MAGOHB | CXCL2 |
| EFEMP1 | CACNA2D4 |
| EED | PPM1K |
| KIF14 | C17orf103 |
| NUP35 | MXD1 |
| DTYMK | MAGIX |
| SSX2IP | PTPRCAP |
| CELF2 | DPM3 |
| NETO2 | EVPL |
| PHLPP2 | SLC2A13 |
| PTBP1 | IL1B |
| FKBP3 | KCNE4 |
| URB2 | INPP5J |
| EEF1E1 | FRAT1 |
| BEGAIN | DUOX2 |
| CACYBP | FBXL15 |
| HMGN5 | C15orf48 |
| HJURP | FAM86FP |
| DBF4 | NR3C2 |
| XRCC3 | STX1B |
| TMCC3 | RP11-273G15.2.1 |
| SPAG5 | RASSF4 |
| AC108488.3.1 | P2RX4 |
| ATOX1 | TPD52L1 |
| SLC25A3 | RP11-420G6.4.1 |
| TUBB | P2RY11 |
| CCDC152 | ADCK3 |
| CENPL | PARP10 |
| GAS6 | AC103810.2 |
| RP11-540A21.2.1 | HERC5 |
| NXT2 | TFEB |
| LRR1 | FAM84B |
| E2F1 | AC093627.10.1 |
| RP11-122A3.2.1 | OAS2 |
| KCNH4 | ARHGAP9 |
| MYEOV | FBXO24 |
| TMEM194B | CD34 |
| RANGAP1 | CD14 |
| CNTF | OTUD1 |
| NASP | ICA1 |
| MAP7D3 | AC005152.2.1 |
| RP1-239B22.1.1 | WDFY3-AS2 |
| DUS2L | HIST1H2AC |
| FKBP1A | SELPLG |
| NOLC1 | PDGFRB |
| ZNF702P | RP11-566K11.1.1 |

| | |
|---|---|
| CDCA5 | SHC2 |
| IMMP2L | CES3 |
| SUPT16H | GBP5 |
| MIR621 | MYL5 |
| RP11-64D22.2.1 | JHDM1D |
| CEP97 | YPEL2 |
| ITGB3BP | DHX58 |
| ERCC8 | IFIT1 |
| WDR62 | RP3-395M20.8.1 |
| ZNF239 | DFNB31 |
| RP11-680F8.1.1 | LYG1 |
| GNL3L | FAM66D |
| MAPKAPK3 | RP5-882C2.2.1 |
| ADK | IL1R1 |
| CENPV | LTB4R |
| UTRN | PDXDC2P |
| PSMD1 | IL4I1 |
| GTF2H3 | FOXO4 |
| USP49 | AC127496.1 |
| C3orf26 | ANKZF1 |
| CYP26B1 | CSF2 |
| JAM3 | LENG9 |
| SPA17 | AC097500.2.1 |
| BTG3 | CCDC19 |
| MRPL15 | FURIN |
| KPNA2 | IFIH1 |
| RRP15 | GBP4 |
| HSPB11 | CCNG2 |
| C17orf89 | FZD1 |
| HAT1 | SNHG5 |
| UBE2S | PDZD7 |
| RBM12B | DAPK2 |
| MRPL47 | C20orf195 |
| MSI2 | C9orf163 |
| KIAA0020 | PCSK4 |
| PTPN1 | KIF26B |
| GLRX3 | SERPINE2 |
| CFL1 | MSMO1 |
| CDH24 | CTC-523E23.1.1 |
| HNRNPA3 | HIST1H3E |
| XYLB | PAQR6 |
| DRAP1 | P4HA2 |
| ACTR3B | AOC3 |
| CHCHD3 | IRS2 |
| H2AFV | MAFB |
| NSMCE1 | MXD4 |
| COLQ | DNER |
| CEP41 | MDGA1 |
| NUTF2 | CH25H |
| SMARCC1 | TST |
| KIF2C | RARRES3 |
| ATP5G1 | UNC13A |
| ISPD | MST1P9 |
| CHTF8 | DNAH2 |
| IPO9 | KCNK5 |
| AC026271.4.1 | PPIL6 |
| TTF2 | RP11-1391J7.1.1 |
| DHRS4 | RHPN1 |
| AC068282.3.1 | FOSB |
| SF3B3 | RP11-202P11.1.1 |
| GSG2 | MIR29B2 |
| AHCTF1 | CEACAM1 |
| LPHN3 | RNF24 |
| KIF22 | YPEL3 |
| IMMP1L | GPT |
| SNRPB | CALML6 |
| DCLRE1A | RP1-163M9.6.1 |
| ZNF681 | NPPA-AS1 |
| CDH2 | PELI2 |
| GPR125 | FAM71E1 |
| ANKRD18A | BPI |

-continued

| | |
|---|---|
| RP11-110I1.12.1 | RASSF5 |
| SCD5 | TMEM53 |
| ARMC10 | ABTB1 |
| AC009948.5.1 | UCN |
| KIF5C | IDUA |
| RP11-381E24.1.1 | GDPD1 |
| PACSIN3 | RP4-758J18.10.1 |
| GNB4 | BMF |
| RP11-58E21.3.1 | TRIB2 |
| PARP1 | DYRK1B |
| HSPA4L | SCNN1D |
| PRPS1 | CLIP2 |
| PPIL1 | INHA |
| XRCC6 | FAM47E |
| COQ2 | LRRC24 |
| CBX2 | GFI1 |
| LBH | EPB41L4A-AS1 |
| RNASEH1 | MVD |
| RFT1 | THBS3 |
| C1orf114 | CARNS1 |
| ITSN1 | C16orf79 |
| ATXN10 | SLC16A13 |
| WHSC1 | CTD-2292P10.4.1 |
| RP5-991G20.4.1 | PDE5A |
| SAAL1 | CTC-378H22.2.1 |
| FER | MUC1 |
| RP1-152L7.5.1 | AC008440.10.1 |
| MCM8 | PCSK9 |
| C4orf10 | CTD-2547L24.3.1 |
| CROT | ICAM5 |
| GTF2H2 | MUC20 |
| BAG2 | PPP1R3C |
| METTL8 | KLF4 |
| SEC14L2 | NINJ1 |
| C20orf94 | CLIP3 |
| HDAC8 | CTD-2517M22.14.1 |
| PRMT3 | AC022098.1 |
| HAUS1 | ABCA6 |
| POLR3G | BBC3 |
| CCT2 | RP13-15E13.1.1 |
| RP11-14N7.2.1 | CXCL3 |
| AC034193.5.1 | RP11-369J21.5.1 |
| CNTLN | PRR15 |
| CCDC34 | C14orf45 |
| DLX1 | TMEM198 |
| ABCC4 | ZNF425 |
| RFC5 | GAL3ST1 |
| PSMC5 | SLC1A7 |
| CSTF2 | ISG15 |
| LIG1 | ATF3 |
| SLC19A1 | ICOSLG |
| BRCC3 | ATP8A1 |
| ZW10 | LINC00324 |
| AFAP1L1 | FBXO32 |
| CDC123 | EXOC3L4 |
| RP11-521B24.3.1 | SRCIN1 |
| LRRC58 | HSF4 |
| ALMS1 | DBP |
| FAM111A | CDH3 |
| PUS7 | AC021593.1 |
| DYNC1H1 | RNF152 |
| EFNB2 | ISG20 |
| BCAS4 | KIAA1683 |
| MYH9 | RP5-885L7.10.1 |

-continued

| | |
|---|---|
| HSPA14 | CARD14 |
| TMEM56 | PIP5K1B |
| ZDHHC2 | NCF2 |
| KIF18A | PPP1R32 |
| CDK4 | RAB17 |
| CKAP2L | CHPF |
| MRE11A | KLHL24 |
| PSRC1 | PDGFRA |
| NUP88 | DNAH10OS |
| RCC1 | RP11-454H13.6.1 |
| GEMIN4 | ABCA7 |
| C1orf74 | TCP11L2 |
| VRK1 | S1PR1 |
| PSMC1 | HIST1H2BD |
| DOCK1 | NEURL3 |
| ALDH3A1 | SYT5 |
| GLT8D2 | GPR35 |
| KATNAL1 | CARD9 |
| SERBP1 | CTD-2313N18.5.1 |
| WDR77 | LIPH |
| PHTF2 | EFNA3 |
| PSMB2 | C3 |
| BCAT1 | MID2 |
| STRA13 | RP11-536G4.2.1 |
| UBE2C | PNPLA7 |
| PHEX | CYP7A1 |
| ADSL | TESK2 |
| HSDL2 | TNFSF15 |
| CEP192 | ZNF385C |
| GOT2 | RP11-757G1.6.1 |
| STIP1 | FBXO2 |
| VBP1 | LRRN1 |
| GNPNAT1 | ZSCAN4 |
| DLC1 | PRSS27 |
| FUBP1 | EFNA1 |
| HEATR1 | CNNM1 |
| TBC1D1 | DDIT4 |
| ECT2 | SCN9A |
| GALNT1 | C2 |
| EXOG | CCDC114 |
| CTD-2366F13.1.1 | RRM2P3 |
| POLA2 | AP000696.2.1 |
| SLC25A15 | PDE4C |
| NEU3 | CATSPERG |
| DOCK5 | ELF5 |
| CETN3 | HS3ST3A1 |
| BMP4 | AC073321.5.1 |
| CCDC72 | CFB |
| SORL1 | PARM1 |
| UCHL5 | C1orf145 |
| ARPC4 | C19orf51 |
| FAM198B | CTC-454M9.1.1 |
| KIAA1586 | CCPG1 |
| GSTO1 | CTH |
| AC097359.1 | MALAT1 |
| BMP2K | TRIB3 |
| SSBP1 | NYAP1 |
| C3orf67 | KLF9 |
| SMC3 | LINC00176 |
| AP1B1 | IER3 |
| ACAD9 | GBP2 |
| C2CD4C | VEGFA |
| SLIRP | SAT1 |
| SNAPC1 | BAIAP3 |
| RPL26L1 | RP11-93B14.5.1 |
| MGAT5B | ANKRD24 |
| FSTL1 | GAA |
| PARVB | CASP5 |
| TIMM23 | OASL |
| KLF12 | MLXIPL |
| C1QBP | RP11-115C10.1.1 |

| | |
|---|---|
| CCRL1 | TSC22D3 |
| SLC16A7 | OPRL1 |
| CDC6 | SERPINA5 |
| AC004381.6.1 | SLCO4A1 |
| CBFB | IGSF10 |
| APAF1 | S100P |
| PRKAR1B | EPAS1 |
| FAM72D | SCARF1 |
| FOXRED2 | TNFSF10 |
| TMEM209 | ECT2L |
| CEP76 | PSD |
| DLG5 | CHAC1 |
| AC003665.1.1 | ANG |
| ACTL6A | CA9 |
| PDP1 | PIK3IP1 |
| C11orf51 | FLRT3 |
| RPL39L | RP11-736K20.5.1 |
| NUBPL | CEACAM22P |
| SFPQ | MYO15B |
| EME1 | DPEP1 |
| FANCM | KLK10 |
| HMBS | ADM2 |
| HNRNPR | ACCN3 |
| HDAC9 | LDB3 |
| HECW1 | FER1L4 |
| GCSH | CEBPD |
| LAPTM4B | TMEM105 |
| GDF11 | CCDC40 |
| NAV2 | RP3-395C13.1.1 |
| NR2F2 | ADCY4 |
| INO80C | NKPD1 |
| PPAT | SLC6A9 |
| UMPS | C13orf33 |
| CACNB4 | SERPINA3 |
| PLCL2 | ACSS2 |
| PRMT5 | SLC2A6 |
| ACADSB | EGR1 |
| INCENP | TSPEAR-AS1 |
| LARS2 | MAPK15 |
| ZNF714 | RP11-178D12.1.1 |
| CCDC86 | FOS |
| PSMD2 | ANGPTL1 |
| LRRC20 | ZNF467 |
| ROCK2 | RP11-712B9.2.1 |
| C12orf48 | PRSS35 |
| TNPO1 | NHLRC4 |
| PPAP2B | SLC6A12 |
| C14orf126 | ICAM1 |
| CDC42BPA | C2CD4A |
| BCCIP | GPR132 |
| PSIP1 | STRC |
| LSM3 | C6orf223 |
| MALT1 | NFE2 |
| AAK1 | CTD-2319I12.1.1 |
| CABYR | FAM167B |
| RBM12 | PNCK |
| CYCS | TPPP3 |
| SFMBT1 | ITGA10 |
| MPHOSPH9 | ODF3B |
| SEH1L | WFDC10B |
| DCAF13 | GRIP2 |
| TIMM10 | TXNIP |
| LYRM1 | NUPR1 |
| FAM171A1 | ARRDC4 |
| CENPH | SSPO |
| RP11-117L6.1.1 | TBX4 |
| BRIX1 | LAMP3 |
| PEG10 | SLCO4C1 |
| THOC7 | HPN |
| CDCA7L | FAM132A |
| HPRT1 | GAL3ST2 |
| CEP170 | NGFR |
| SF3A3 | C2CD4B |

-continued

| | |
|---|---|
| PMVK | RANBP3L |
| HSPD1 | C17orf28 |
| TDP1 | C21orf90 |
| DNMT3B | MYO15A |
| CKAP2 | LRRC4C |
| C12orf24 | PLCH2 |
| ANKRD28 | HSPA6 |
| CKAP5 | IGFALS |
| POLR1E | KLB |
| DCUN1D5 | AC005013.5.1 |
| ORC1 | CSF3R |
| KCTD1 | RYR1 |
| PSMA7 | |
| CCDC134 | |
| PSMC2 | |
| PLS3 | |
| PIGN | |
| CTD-2224J9.2.1 | |
| NUP153 | |
| ME3 | |
| PITPNM3 | |
| ABCD3 | |
| IQCC | |
| DCLRE1B | |
| USP1 | |
| AC108463.2.1 | |
| UPF2 | |
| SSRP1 | |
| ALG8 | |
| STARD13 | |
| NEK2 | |
| FCF1 | |
| GNG12 | |
| MASTL | |
| TBC1D5 | |
| AP3B1 | |
| CBX3 | |
| PGRMC1 | |
| ATG3 | |
| POLH | |
| PDCD11 | |
| RP11-666A20.1.1 | |
| ZDHHC23 | |
| RGS17 | |
| FAM72A | |
| SEPHS1 | |
| FAM122B | |
| VOPP1 | |
| PSMA3 | |
| FLVCR2.1 | |
| LIN9 | |
| MANEA | |
| FAM208B | |
| GTPBP4 | |
| TTI1 | |
| CCDC88A | |
| FAM48A | |
| TMSB15B | |
| SELRC1 | |
| RIMKLB | |
| WDR17 | |
| ODZ3 | |
| CNOT1 | |
| SMCHD1 | |
| RDX | |
| POLD3 | |
| LAS1L | |
| CLTC | |
| PPP1R14B | |
| GEMIN5 | |
| AGK | |
| C10orf125 | |
| SMS | |
| PDAP1 | |
| LYPD6 | |

| | |
|---|---|
| | RP11-290F20.1.1 |
| | SLC36A1 |
| | TRAIP |
| | RP6-65G23.3.1 |
| | PPIA |
| | RP11-85G18.4.1 |
| | KCNC4 |
| | GDAP1 |
| | CABLES1 |
| | LGALS1 |
| | RPP30 |
| | PI4K2B |
| | DSN1 |
| | ZNF620 |
| | USP6NL |
| | C9orf100 |
| | CAV2 |
| | PTCD2 |
| | KIAA1147 |
| | TOP2B |
| | TXNRD1 |
| | MYL6 |
| | RNASEH2A |
| | RBFOX2 |
| | CCT6A |
| | AMMECR1 |
| | DLD |
| | BAI2 |
| | ORC5 |
| | TIMM8A |
| | BEND6 |
| | TSC22D2 |
| | NAP1L5 |
| | ATIC |
| | SIGLEC15 |
| | AP4S1 |
| | BAX |
| | TTK |
| | WDR12 |
| | TFAM |
| | GPRIN1 |
| | PRDX1 |
| | GEMIN6 |
| | MMACHC |
| | JUN |
| | ERC1 |
| | EPHB2 |
| | XPO6 |
| | KIF24 |
| | SRGAP1 |
| | AURKB |
| | TRRAP |
| | GPD2 |
| | SCFD2 |
| | SMAP2 |
| | GSS |

Supplementary Data 41: Comparison of overlaps between recurrent DE genes across all samples (vs. A38Per) and DMSO vs. 6AN treated A38Lg cells

| Recurrent Up/ 6AN Down | Genes | Recurrent Down/ 6AN Up | Genes | Recurrent Up/ 6AN Up | Genes | Recurrent Down/ 6AN Down | Genes |
|---|---|---|---|---|---|---|---|
| Coregulated/ 6AN down: 255/1968 (13%) | PPIA | Coregulated/ 6AN up: 332/2192 (15%) | SAT1 | Coregulated/ 6AN up: 82/2192 (0.04%) | EEF1A1 | Coregulated/ 6AN down: 111/1968 (0.06%) | KRT19 + M2:M52 |
| Coregulated/ Recurrent up: 255/891 (28.6%) | DYNC1H1 | Coregulated/ Recurrent down: 332/1842 (18%) | ATP1B1 | Coregulated/ Recurrent up: 82/891 (9%) | AKR1C2 | Coregulated/ Recurrent down: 111/1842 (0.06%) | DCBLD2 |
| | CCT5 | | GRN | | RPL12 | | PLAU |
| | YBX1 | | JUP | | RPL31 | | EZR |

| | | | |
|---|---|---|---|
| HNRNPA3 | LCN2 | RPL29 | GPR110 |
| XRCC6 | CST1 | IDI1 | COL17A1 |
| PRDX1 | TXNIP | XBP1 | ANO1 |
| SERBP1 | LAMB3 | ATP2B1 | PADI1 |
| DPYSL3 | DDR1 | HERPUD1 | SDC1 |
| ECT2 | DUOX2 | MTHFD2 | CD82 |
| CBX3 | SLCO4A1 | MAN1A1 | CGN |
| SLC25A3 | GSN | SHMT2 | LY6D |
| HMGN2 | LIMA1 | MAP2 | CRABP2 |
| TMPO | LYZ | ABCA3 | DOCK9 |
| CYCS | MUC1 | TOMM7 | SPNS2 |
| PAICS | GNE | ASNS | RAPGEF3 |
| MYL6 | DAB2IP | PYCR1 | FGFBP1 |
| NOP56 | TNIP1 | TBC1D4 | RBP1 |
| HNRNPR | LIPH | UCP2 | PRSS12 |
| FKBP1A | RHBDF2 | CELSR3 | C1orf106 |
| THBS1 | HS3ST1 | LETMD1 | QPCT |
| DEK | RDH10 | KLHDC2 | STEAP2 |
| ASPM | MUC20 | ARG2 | ARHGDIB |
| NUP210 | CLIP2 | LEPRE1 | ZNF185 |
| PCNA | KLK10 | SLC25A29 | DHRS9 |
| HNRNPAB | SLC44A2 | PCK2 | CDC42BPG |
| ATIC | EFNB1 | SLC26A6 | NBPF10 |
| NCAPD2 | NFKBIA | PTPRM | MUC4 |
| RANGAP1 | EVPL | SYT11 | PLEKHA7 |
| MYO1B | ENDOD1 | FAM113A | AIG1 |
| MTHFD1 | ICAM1 | GAB2 | RP11-800A3.4.1 |
| FAM208B | CDC42EP2 | CRELD2 | MMD |
| GPD2 | CTSL1 | SLC1A4 | SAA1 |
| GTPBP4 | DRAM1 | ABHD14B | ARAP2 |
| TUBA4A | TRIM2 | PDK1 | ANKRD22 |
| SMCHD1 | NFKBIZ | C9orf150 | CDS1 |
| FOXM1 | ADAM8 | MLLT3 | ALS2CL |
| SMARCC1 | TRIB2 | SSBP2 | GALNT6 |
| TFDP1 | GSDMB | C3orf23 | KRT15 |
| XPO6 | SGK1 | DDT | XDH |
| TOP2B | ARHGEF16 | SARM1 | DGAT2 |
| HEATR1 | LRCH4 | OSBPL6 | FBP1 |
| ODC1 | HERC5 | LEPREL2 | CLDN10 |
| ZWINT | PLEKHM1 | EEF1A1P5 | RHOD |
| ATXN10 | ASAH1 | HCN2 | PRSS3 |
| NUP155 | TMEM8A | VLDLR | CTSL2 |
| CDCA7L | PRICKLE4 | BAMBI | SNAI2 |
| SNRPB | NEU1 | USE1 | GALNT12 |
| GNPNAT1 | TNFSF15 | CGREF1 | P2RY2 |
| WDR3 | PLAUR | ATHL1 | RAG1 |
| HJURP | AC103810.2 | GPR37 | PADI3 |
| KNTC1 | RHBDF1 | DERL3 | TESC |
| REV3L | HSD17B11 | PLK3 | SELL |
| CDH2 | ROBO4 | SLC29A4 | GPR116 |
| FARSB | EREG | TMEM234 | GCHFR |
| CCDC88A | VWA1 | RP11-66N24.3.1 | RP11-314P12.3.1 |
| NETO2 | TJP3 | CORO6 | CHST4 |
| NUP153 | PDCD4 | C9orf37 | SHANK2 |
| USP1 | PTPRE | EEF1A1P6 | DNAH10 |
| MCM6 | C15orf48 | DNAJC3-AS1 | KRT23 |
| POLD2 | TPBG | C3orf78 | COL1A1 |
| SF3A3 | TNFAIP3 | MCEE | NMNAT2 |
| TYMS | PROS1 | RP11-480A16.1.1 | AKAP6 |
| KIAA1324 | GPR108 | ZNF70 | AADAC |
| TMEM48 | AGFG2 | NAT6 | VEPH1 |
| TCOF1 | RHBDD2 | SEMA3F | C7orf58 |
| PHIP | DGAT1 | VKORC1 | DNAH12 |
| BRIX1 | HBP1 | RP5-1103G7.4.1 | SLC22A20 |
| UTP20 | RNF103 | P2RX6 | MCC |
| CTPS | TSC22D3 | C10orf102 | RP11-7K24.3.1 |
| RANBP1 | CAPS | THTPA | ANKRD56 |
| SACS | SLC2A6 | FTX | CTD-2021J15.2.1 |
| DTL | ABCA7 | AC002472.8.1 | ARL14 |
| CDC20 | TMC4 | RP11-243J18.3.1 | C15orf62 |
| AP1B1 | FAM193B | CTD-307407.5.1 | METTL7B |

-continued

| | | | |
|---|---|---|---|
| CDC6 | VPS28 | RP11-574K11.20.1 | SLC4A3 |
| ABCD3 | ARSD | CES4A | KLHL13 |
| EBNA1BP2 | NCF2 | METTL12 | RP11-357H14.19.1 |
| PHTF2 | MMP28 | RP11-390P2.4.1 | FGFR3 |
| TRIP13 | PARP10 | RP11-216F19.1.1 | PKDCC |
| RUVBL1 | LZTS2 | RP11-85K15.2.1 | RP11-157P1.4.1 |
| RCC1 | ANKRD13D | SEPT7L | SMO |
| MYBL2 | DNASE2 | | CD22 |
| CHML | LYNX1 | | SYTL5 |
| CCDC165 | APOBEC3G | | TNNT2 |
| SEH1L | CDH3 | | ADAMTS14 |
| WDR12 | AQP3 | | ANXA10 |
| TMEM56 | NYNRIN | | TTC3P1 |
| ERC1 | ABCG1 | | NMU |
| RFC3 | SH3YL1 | | RP11-597D13.9.1 |
| DEPDC1 | FBXO2 | | UNC5C |
| RP1-239B22.1.1 | PPP1R16A | | AADAT |
| BMP2K | SESN3 | | GRHL1 |
| NT5DC2 | TMPRSS3 | | TMEM169 |
| MPHOSPH9 | HEATR7A | | CYP24A1 |
| HDAC9 | KYNU | | RP11-448G15.3.1 |
| STMN3 | METTL7A | | ASB9 |
| MRTO4 | FA2H | | NAALADL2 |
| CDCA8 | ZC3H12A | | FAM46B |
| S100A2 | CFI | | CFTR |
| PI4K2B | SLC15A3 | | C16orf74 |
| MCM8 | SIGIRR | | RP11-416I2.1.1 |
| GTF2H3 | FER1L4 | | PLAC1 |
| JUN | SLC39A11 | | ZNF658 |
| TTF2 | FOXQ1 | | SP6 |
| FAM171A1 | RASSF5 | | TTN |
| FKBP5 | DHRS3 | | C8orf46 |
| ADSL | ARHGEF3 | | GPR65 |
| DIAPH3 | S100P | | LEF1 |
| KIAA0586 | ZG16B | | RP11-6F2.4.1 |
| POLQ | PTK6 | | DENND2A |
| EXO1 | CDA | | |
| EEF1E1 | IL32 | | |
| ODZ3 | ZNF862 | | |
| SSX2IP | CD14 | | |
| CEP97 | TMED1 | | |
| ABCC4 | G0S2 | | |
| RAD51AP1 | ENDOV | | |
| MRPL47 | SMAD6 | | |
| C9orf140 | MIA | | |
| GEMIN5 | CACNB1 | | |
| FANCD2 | ARL4D | | |
| CCNE2 | JAK2 | | |
| UMPS | KCNMB4 | | |
| BARD1 | IRAK2 | | |
| USP13 | RELB | | |
| CENPV | CEBPB | | |
| SMTN | MAFF | | |
| PRPS1 | C9orf16 | | |
| CCNF | RALGPS1 | | |
| RFC5 | LTB4R | | |
| ATP5G1 | CSF2RA | | |
| POLR3G | C10orf32 | | |
| CBX2 | SAT2 | | |
| NOP16 | ALPPL2 | | |
| MCM10 | CCDC69 | | |
| SLC16A7 | NR1H3 | | |
| POP1 | GRAMD1C | | |
| CLSPN | FAM113B | | |
| PFAS | WASH7P | | |
| KLF12 | TGFBR3 | | |
| GEMIN4 | YPEL3 | | |
| C3orf26 | LRRN1 | | |
| GMNN | MAST3 | | |

| | |
|---|---|
| CENPN | ABC7-42389800N19.1.1 |
| KIF15 | ZNF467 |
| GDAP1 | XAF1 |
| THOC7 | C16orf7 |
| OPN3 | RP3-395M20.8.1 |
| C22orf29 | DNAH2 |
| BAG2 | ADCY4 |
| ERCC2 | CDC42EP5 |
| JAM3 | ITGAX |
| DERA | ANKRD42 |
| GPRIN1 | NLRP1 |
| E2F2 | AC021593.1 |
| CDC45 | N4BP2L1 |
| ARRB2 | CLDN15 |
| NCS1 | PIWIL4 |
| SFMBT1 | S1PR1 |
| RAD54L | HLA-H |
| C1orf112 | NEURL3 |
| PRKAR1B | P2RX4 |
| FANCM | AC007283.5.1 |
| CENPL | CA11 |
| SELRC1 | DPEP1 |
| DOCK10 | TBC1D3F |
| ORC1 | IER5L |
| ALDH1B1 | PER1 |
| BCL2 | ZSWIM4 |
| PSMC3IP | ITGA10 |
| SNRNP25 | IL15 |
| PRIM1 | SERPINA3 |
| HSPA4L | RTP4 |
| SUV39H2 | GLI4 |
| MAGOHB | C17orf103 |
| HMGB1P5 | SIX5 |
| RP11-14N7.2.1 | SNPH |
| WDR77 | PIP5K1B |
| CENPH | TFEB |
| NME1 | IDUA |
| LRRC8C | TMEM102 |
| AC027612.6.1 | SPRY3 |
| METTL8 | FMO5 |
| POLR1E | MTRNR2L9 |
| HOMER1 | VSIG10L |
| RGS17 | GIMAP2 |
| DCLRE1B | PLCH2 |
| POLE2 | LRRC6 |
| CENPW | LRFN3 |
| SKA1 | RILPL2 |
| ADAT2 | TNFSF12 |
| CCDC41 | CROCC |
| WDR4 | HLA-K |
| CCDC18 | PRICKLE3 |
| PDSS1 | CXCL3 |
| C12orf24 | NOS3 |
| PARVB | FBXO6 |
| MMP24 | CCDC146 |
| C14orf126 | CSF2 |
| SLC25A15 | CEP85L |
| NEGR1 | GEMIN8 |
| CAP2 | ZNF628 |
| OIP5 | CXCL2 |
| KIF5C | ZDHHC1 |
| ARHGAP11B | NR3C2 |
| FAM86A | RP11-285F7.2.1 |
| TBC1D7 | PLEKHF1 |
| CEP128 | RP11-403I13.8.1 |
| DLEU2 | B3GALT4 |
| BOLA3 | NEIL1 |
| COQ3 | KNDC1 |
| C17orf89 | PON3 |
| ARHGEF26 | CFB |
| GDF11 | ENDOU |
| ACTR3B | FOXO4 |
| ASRGL1 | DDO |
| XYLB | BBC3 |

-continued

| | |
|---|---|
| RP1-140K8.5.1 | KB-1460A1.5.1 |
| SFXN2 | SLC16A13 |
| TIMM8A | GAS7 |
| MNS1 | RNF152 |
| GTF2H2 | ABCA6 |
| AC009948.5.1 | SLC16A6 |
| ZNF239 | RENBP |
| RP11-253E3.3.1 | KIAA1683 |
| ASTN2 | BBS12 |
| CHAC2 | CACNA2D4 |
| CSMD3 | UPK3B |
| RASSF2 | AP001372.2.1 |
| CCDC138 | ZNF517 |
| C1orf74 | ACYP2 |
| CCDC134 | ARHGAP25 |
| CABYR | PRX |
| RP6-65G23.3.1 | CES3 |
| PPIAP29 | ACCN3 |
| CYB5RL | C19orf51 |
| RP11-521B24.3.1 | IL4I1 |
| RP1-152L7.5.1 | VMAC |
| C20orf94 | |
| AL357673.1 | TNFRSF9 |
| | RP11-757G1.6.1 |
| ISPD | NFAM1 |
| ELOVL2 | RP11-353B9.1.1 |
| RBM24 | PDZD7 |
| RP11-204J18.3.1 | CARD14 |
| DPF1 | NYAP1 |
| RP11-381E24.1.1 | CD34 |
| RP11-1334A24.4.1 | RP11-325F22.3.1 |
| MIR621 | EXOC3L4 |
| AC092329.1 | RP5-1182A14.3.1 |
| | JAK3 |
| RP3-324O17.4.1 | |
| CTD-2574D22.2.1 | WDFY3-AS2 |
| PDE1A | PDGFRA |
| RP11-33N16.1.1 | MLXIPL |
| RP11-618G20.2.1 | KLHDC1 |
| | MIR29C |
| | RP11-712B9.2.1 |
| | CTD-2292P10.4.1 |
| | PCSK4 |
| | CLDN9 |
| | PODN |
| | COL11A2 |
| | RP11-65J3.1.1 |
| | PPP1R32 |
| | EFHC2 |
| | TMEM105 |
| | AC005152.2.1 |
| | CASP5 |
| | TBX6 |
| | DNAH10OS |
| | SCARF1 |
| | RP11-420G6.4.1 |
| | ROM1 |
| | PYGM |
| | SLCO4C1 |
| | CCDC114 |
| | FAM71E1 |

-continued

RP11-263K19.6.1
CTD-2341M24.1.1
PCDHAC1
CLIP3
C7orf63
C17orf108
ECEL1P2
LRRC24
ZNF385C
TPPP3
RP11-108M9.4.1
ANKRD24
SRCRB4D
MIR29B2
DNAH7
RP11-454H13.6.1
RP11-369J21.5.1
TMPRSS5
PTPRCAP
BCO2
C2orf81
FAM66C
LINC00176
GPR132
SLC5A12
PDE4C
ICAM5
C20orf195
FBXO24
NGFR
TNFSF13B
MST1P9
CH25H
CTC-523E23.1.1
NFE2
CTC-378H22.2.1
FAM132A
GBP5
HOXD4
UCN
NKPD1
ELF5
LINC00324
RP11-115C10.1.1
ANGPTL1
RP11-536G4.2.1
FAM66D
RP4-541C22.5.1
HSPA6
CTD-2313N18.5.1
CTD-2547L24.3.1
CYP7A1
IGFALS
RRM2P3
U7

Although the invention has been described with reference to the above example, it will be understood that modifications and variations are encompassed within the spirit and scope of the invention. Accordingly, the invention is limited only by the following claims.

---

What is claimed is:

1. A method of identifying a gene or DNA region that is a target for epigenetic reprogramming in a subject comprising:
    (a) detecting large organized heterochromatin lysine (K)-9 modified domains (LOCKs) and large DNA hypomethylated blocks in a region of DNA in a cancer cell from the subject;
    (b) subsequently to (a), contacting the cancer cell with a reprogramming agent;
    (c) subsequently to (b), performing a gene expression analysis on the cancer cell, and
    (d) identifying in the cancer cell after contact with the reprogramming agent:
        one or more alterations in methylation patterns in the LOCKs and large DNA hypomethylated blocks of DNA in the region detected in (a) as compared to a reference DNA from a cancer cell not contacted with the reprogramming agent; and
        one or more changes in gene expression as compared to a cancer cell not contacted with the reprogramming agent,
    wherein alterations in methylation patterns and changes in gene expression indicate epigenetic reprogramming of the cancer cell and thereby identifying genes and DNA regions that are targets for epigenetic reprogramming.

2. The method of claim 1, wherein the cancer cell is from a solid tumor.

3. The method of claim 1, wherein the subject has pancreatic ductal adenocarcinoma (PDAC) and/or is at risk of having metastasis thereof.

4. The method of claim 1, wherein the detection comprises analysis of H3K9Me2/3 and/or H4K20Me3.

5. The method of claim 1, wherein the detection comprises analysis of H3K27Ac and/or H3K9Ac.

6. The method of claim 1, wherein detection comprises analysis by Western blotting.

7. The method of claim 1, wherein detection comprises analysis by ChIP with antibodies to H3K9Me2/3 and/or H4K20Me3, optionally followed by sequencing.

8. The method of claim 1, wherein detection comprises analysis by ChIP with antibodies to H3K27Ac and/or H3K9Ac, optionally followed by sequencing.

9. The method of claim 1, wherein detection comprises analysis by whole genome bisulfite sequencing.

10. The method of claim 1, wherein there is an absence of driver mutations for metastasis in the cancer cells.

11. The method of claim 1, further comprising analysis of euchromatin islands and/or euchromatin LOCKs.

* * * * *